(12) United States Patent
Bozik et al.

(10) Patent No.: US 9,849,116 B2
(45) Date of Patent: Dec. 26, 2017

(54) COMPOSITIONS AND METHODS OF USING (R)-PRAMIPEXOLE

(71) Applicant: KNOPP BIOSCIENCES LLC, Pittsburgh, PA (US)

(72) Inventors: Michael E. Bozik, Pittsburgh, PA (US); Valentin Gribkoff, Wallingford, CT (US); Thomas Petzinger, Jr., Pittsburgh, PA (US)

(73) Assignee: Knopp Biosciences LLC, Pittsburgh, PA (US)

( * ) Notice: Subject to any disclaimer, the term of this patent is extended or adjusted under 35 U.S.C. 154(b) by 0 days.

(21) Appl. No.: 14/878,581

(22) Filed: Oct. 8, 2015

(65) Prior Publication Data
US 2016/0030397 A1 Feb. 4, 2016

Related U.S. Application Data

(63) Continuation of application No. 13/059,713, filed as application No. PCT/US2009/054292 on Aug. 19, 2009, now abandoned.

(60) Provisional application No. 61/090,094, filed on Aug. 19, 2008, provisional application No. 61/113,680, filed on Nov. 12, 2008.

(51) Int. Cl.
| | | |
|---|---|---|
| *A61K 31/428* | (2006.01) |
| *A61K 31/197* | (2006.01) |
| *A61K 9/16* | (2006.01) |
| *A61K 9/20* | (2006.01) |
| *A61K 31/425* | (2006.01) |
| *A61K 45/06* | (2006.01) |
| *A61K 9/00* | (2006.01) |

(52) U.S. Cl.
CPC .......... *A61K 31/428* (2013.01); *A61K 9/0053* (2013.01); *A61K 9/1623* (2013.01); *A61K 9/1635* (2013.01); *A61K 9/1652* (2013.01); *A61K 9/2018* (2013.01); *A61K 9/2027* (2013.01); *A61K 9/2054* (2013.01); *A61K 31/197* (2013.01); *A61K 31/425* (2013.01); *A61K 45/06* (2013.01)

(58) Field of Classification Search
None
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran et al. |
| 4,314,557 A | 2/1982 | Chandrasekaran et al. |
| 4,327,725 A | 5/1982 | Cortese et al. |
| 4,379,454 A | 4/1983 | Campbell et al. |
| 4,395,859 A | 8/1983 | Rohrer |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,588,580 A | 5/1986 | Gale et al. |
| 4,612,008 A | 9/1986 | Wong et al. |
| 4,626,539 A | 12/1986 | Aungst et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,731,374 A | 3/1988 | Griss et al. |
| 4,781,924 A | 11/1988 | Lee et al. |
| 4,783,337 A | 11/1988 | Wong et al. |
| 4,788,062 A | 11/1988 | Gale et al. |

(Continued)

FOREIGN PATENT DOCUMENTS

| | | |
|---|---|---|
| AU | 2006279643 B2 | 8/2006 |
| AU | 2002360600 B2 | 3/2008 |

(Continued)

OTHER PUBLICATIONS

Abrahamson et al. "Structure and expression of the human cystatin C gene" 1990, Biochem J. 268(2):287-294.
Abramova et al. "Inhibition by R(+) or S(−) Pramipexole of Caspase Activation and Cell Death Induced by Methylpyridinium Ion or Beta Amyloid Peptide in SH-SY5Y Neuroblastoma" 2002, J. Neuroscience Res. 67(4):494-500.
Agardh et al. "Expression of antioxidant enzymes in rat retinal ischemia followed by reperfusion" Jul. 2006, Metabolism 55(7):892-898 (Abstract).
Aguila et al. "Prognosis in Amyotrophic Lateral Sclerosis: A population based study" 2003, Neurology 60:813-819.
Anonymous "Variant of Parkinson's Drug Tested in ALS" Jul. 19, 2006 (printed from www.als-mda.org/research/news/060719als_pramipexole.html on (Feb. 21, 2008) (Abstract).

(Continued)

*Primary Examiner* — Bong-Sook Baek
(74) *Attorney, Agent, or Firm* — Pepper Hamilton LLP

(57) ABSTRACT

Pharmaceutical compositions of (R)-pramipexole and one or more secondary therapeutic agents such as, for example, dopamine agonists, dopaminergic agonists, COMT inhibitors, MOA inhibitors, excitatory amino acid antagonists, growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and downregulators, monoamine oxidase type B (MOAB) inhibitors, multi-target agents, kinase inhibitors, Bcl inducers, histone deacetylase (HDAC) mediators, glial modulators, mitochondrial energy promoting agents, myostatin inhibitors, caspase inhibitors and combinations thereof or those related to mitochondrial dysfunction or increased oxidative stress are disclosed.

14 Claims, 5 Drawing Sheets

(56) References Cited

U.S. PATENT DOCUMENTS

| | | |
|---|---|---|
| 4,806,341 A | 2/1989 | Chien et al. |
| 4,816,258 A | 3/1989 | Nedberge et al. |
| 4,843,086 A | 6/1989 | Griss et al. |
| 4,849,226 A | 7/1989 | Gale |
| 4,886,812 A | 12/1989 | Griss et al. |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,024,843 A | 6/1991 | Kuczynski et al. |
| 5,069,909 A | 12/1991 | Sharma et al. |
| 5,071,656 A | 12/1991 | Lee et al. |
| 5,082,668 A | 1/1992 | Wong et al. |
| 5,091,190 A | 2/1992 | Kuczynski et al. |
| 5,112,842 A | 5/1992 | Zierenberg et al. |
| 5,122,382 A | 6/1992 | Gale et al. |
| 5,141,750 A | 8/1992 | Lee et al. |
| 5,284,660 A | 2/1994 | Lee et al. |
| 5,314,694 A | 5/1994 | Gale et al. |
| 5,342,623 A | 8/1994 | Enscore et al. |
| 5,411,740 A | 5/1995 | Lee et al. |
| 5,442,117 A | 8/1995 | Stahley et al. |
| 5,545,413 A | 8/1996 | Kuczynski et al. |
| 5,591,454 A | 1/1997 | Kuczynski et al. |
| 5,635,203 A | 6/1997 | Gale et al. |
| 5,650,420 A | 7/1997 | Hall et al. |
| 5,674,895 A | 10/1997 | Guittard et al. |
| 5,719,060 A | 2/1998 | Hutchens et al. |
| 5,792,664 A | 8/1998 | Chait et al. |
| 5,804,215 A | 9/1998 | Cubbage et al. |
| 5,830,497 A | 11/1998 | Yamanaka et al. |
| 5,840,754 A | 11/1998 | Guittard et al. |
| 5,912,268 A | 6/1999 | Guittard et al. |
| 6,043,251 A | 3/2000 | Douillet et al. |
| 6,156,777 A | 12/2000 | Hall et al. |
| 6,187,802 B1 | 2/2001 | Cheetham et al. |
| 6,197,339 B1 | 3/2001 | Ju |
| 6,228,398 B1 | 5/2001 | Devane et al. |
| 6,255,329 B1 | 7/2001 | Maj |
| 6,262,115 B1 | 7/2001 | Guittard et al. |
| 6,284,774 B1 | 9/2001 | Wright et al. |
| 6,294,790 B1 | 9/2001 | Weinberger |
| 6,443,976 B1 | 9/2002 | Flower et al. |
| 6,458,820 B1 | 10/2002 | Hall et al. |
| 6,480,820 B1 | 11/2002 | Clopton et al. |
| 6,541,486 B1 | 4/2003 | Bitler et al. |
| 6,618,138 B2 | 9/2003 | Khoury |
| 6,667,329 B1 | 12/2003 | Maj |
| 6,675,104 B2 | 1/2004 | Paulse et al. |
| 6,727,367 B2 | 4/2004 | Pospisilik |
| 6,730,325 B2 | 5/2004 | Devane et al. |
| 6,750,235 B2 | 6/2004 | Rosenbaum |
| 6,776,984 B1 | 8/2004 | Schwartz |
| 6,793,936 B2 | 9/2004 | Devane et al. |
| 6,902,742 B2 | 6/2005 | Devane et al. |
| 6,919,092 B2 | 7/2005 | Guittard et al. |
| 6,919,373 B1 | 7/2005 | Lam et al. |
| 6,927,036 B2 | 8/2005 | Gallop et al. |
| 6,929,801 B2 | 8/2005 | Klose et al. |
| 6,930,129 B2 | 8/2005 | Lam et al. |
| 7,005,255 B2 | 2/2006 | Kaddurah-Daouk et al. |
| 7,157,480 B2 | 1/2007 | Bennett, Jr. |
| 7,344,733 B2 | 3/2008 | Beier et al. |
| 7,572,596 B2 | 8/2009 | Bowser |
| 7,741,490 B2 | 6/2010 | Castaldi et al. |
| 8,017,598 B2 | 9/2011 | Bozik et al. |
| 8,186,890 B2 | 5/2012 | Lu |
| 8,192,091 B2 | 6/2012 | Hsu et al. |
| 8,408,815 B2 | 4/2013 | Lin et al. |
| 2002/0004058 A1 | 1/2002 | Yoshii et al. |
| 2002/0103240 A1 | 8/2002 | Pospisilik |
| 2002/0106731 A1 | 8/2002 | Ruben et al. |
| 2002/0151526 A1 | 10/2002 | Gallop et al. |
| 2002/0177626 A1 | 11/2002 | Cook et al. |
| 2003/0013120 A1 | 1/2003 | Patz et al. |
| 2003/0049318 A1 | 3/2003 | Davis et al. |
| 2003/0166696 A1 | 9/2003 | Warsinksy et al. |
| 2003/0203055 A1 | 10/2003 | Rao et al. |
| 2004/0031667 A1 | 2/2004 | Dinkel et al. |
| 2004/0033530 A1 | 2/2004 | Awrey et al. |
| 2004/0067991 A1 | 4/2004 | Greig et al. |
| 2004/0097540 A1 | 5/2004 | Peters et al. |
| 2004/0122104 A1 | 6/2004 | Hirsh et al. |
| 2004/0132788 A1 | 7/2004 | Chabrier De Lassauniere et al. |
| 2004/0132826 A1 | 7/2004 | Hirsh et al. |
| 2004/0219213 A1 | 11/2004 | Burnside et al. |
| 2004/0247656 A1 | 12/2004 | Beier et al. |
| 2004/0265370 A1 | 12/2004 | Odidi et al. |
| 2005/0031667 A1 | 2/2005 | Patel et al. |
| 2005/0032856 A1 | 2/2005 | Bennett, Jr. et al. |
| 2005/0053649 A1 | 3/2005 | Chalmers |
| 2005/0059717 A1 | 3/2005 | Van Eupen et al. |
| 2005/0070715 A1 | 3/2005 | Bhat et al. |
| 2005/0074865 A1 | 4/2005 | Afeyan et al. |
| 2005/0089575 A1 | 4/2005 | Friedl et al. |
| 2005/0148026 A1 | 7/2005 | Bowser et al. |
| 2005/0208156 A1 | 9/2005 | Ploch et al. |
| 2005/0220877 A1 | 10/2005 | Patel et al. |
| 2005/0226926 A1 | 10/2005 | Amidon et al. |
| 2005/0265379 A1 | 12/2005 | Rao |
| 2006/0009659 A1 | 1/2006 | Maywald et al. |
| 2006/0046967 A1 | 3/2006 | Satyam |
| 2006/0051419 A1 | 3/2006 | Friedl et al. |
| 2006/0069263 A1 | 3/2006 | Gribun et al. |
| 2006/0099257 A1 | 5/2006 | Langridge et al. |
| 2006/0106224 A1 | 5/2006 | Gupta et al. |
| 2006/0110450 A1 | 5/2006 | Eisenreich |
| 2006/0121619 A1 | 6/2006 | Bowser |
| 2006/0128643 A1* | 6/2006 | Kaddurah-Daouk .. A61K 45/06 514/43 |
| 2006/0141037 A1 | 6/2006 | Mehta et al. |
| 2006/0148866 A1 | 7/2006 | Xia et al. |
| 2006/0281797 A1 | 12/2006 | Bennett, Jr. |
| 2006/0286167 A1 | 12/2006 | Staunton et al. |
| 2007/0087410 A1 | 4/2007 | Lanahan et al. |
| 2007/0105918 A1 | 5/2007 | Bennett, Jr. |
| 2007/0203209 A1 | 8/2007 | Bartolini et al. |
| 2007/0259930 A1 | 11/2007 | Bozik et al. |
| 2008/0014259 A1 | 1/2008 | Bozik et al. |
| 2008/0020028 A1 | 1/2008 | Shevchuk et al. |
| 2008/0026043 A1 | 1/2008 | Mueller et al. |
| 2008/0081041 A1 | 4/2008 | Nemeth |
| 2008/0096939 A1 | 4/2008 | Keil et al. |
| 2008/0194832 A1 | 8/2008 | Silva Guisasola et al. |
| 2008/0227985 A1 | 9/2008 | Raje et al. |
| 2008/0234338 A1 | 9/2008 | Bennett, Jr. |
| 2009/0042956 A1 | 2/2009 | Bozik et al. |
| 2009/0054504 A1 | 2/2009 | Bozik et al. |
| 2009/0105483 A1 | 4/2009 | Balicki et al. |
| 2009/0149518 A1 | 6/2009 | Nishii et al. |
| 2010/0291073 A1 | 11/2010 | Koiki et al. |
| 2010/0292149 A1 | 11/2010 | Bowser |
| 2011/0009460 A1 | 1/2011 | Gribkoff et al. |
| 2011/0020339 A1 | 1/2011 | Hargreave et al. |
| 2011/0190356 A1 | 8/2011 | Bozik et al. |
| 2011/0218222 A1 | 9/2011 | Bennett, Jr. |
| 2011/0224268 A1 | 9/2011 | Bozik et al. |
| 2011/0293718 A1 | 12/2011 | Bozik et al. |
| 2011/0301210 A1 | 12/2011 | Bennett, Jr. |
| 2012/0134929 A1 | 5/2012 | McGrath et al. |
| 2012/0142715 A1 | 6/2012 | Kim |
| 2012/0148575 A1 | 6/2012 | Koike et al. |
| 2012/0225915 A1 | 9/2012 | Bozik et al. |
| 2012/0253047 A1 | 10/2012 | Allegrini et al. |
| 2012/0258994 A1 | 10/2012 | McKinney et al. |
| 2013/0059801 A1 | 3/2013 | Milne et al. |
| 2013/0079526 A1 | 3/2013 | Greenfield et al. |
| 2013/0116292 A1 | 5/2013 | Bennett, Jr. |
| 2013/0123312 A1 | 5/2013 | Bozik et al. |
| 2013/0172394 A1 | 7/2013 | Bennett, Jr. |
| 2013/0230569 A1 | 9/2013 | Bozik et al. |
| 2013/0245081 A1 | 9/2013 | Gribkoff et al. |

(56) References Cited

U.S. PATENT DOCUMENTS

| | | |
|---|---|---|
| 2013/0273557 A1 | 10/2013 | Gribkoff et al. |
| 2013/0310430 A1 | 11/2013 | Bozik et al. |
| 2014/0018343 A1 | 1/2014 | Romero et al. |
| 2014/0031401 A1 | 1/2014 | Bozik et al. |
| 2014/0100372 A1 | 4/2014 | Raje et al. |
| 2014/0329869 A1 | 11/2014 | Bozik et al. |
| 2015/0018397 A1 | 1/2015 | Bozik et al. |
| 2015/0126745 A1 | 5/2015 | Chen et al. |
| 2016/0158205 A1 | 6/2016 | Bozik et al. |
| 2016/0193186 A1 | 7/2016 | Bozik et al. |
| 2016/0193187 A1 | 7/2016 | Bozik et al. |

FOREIGN PATENT DOCUMENTS

| | | |
|---|---|---|
| AU | 2007333050 B2 | 12/2013 |
| CA | 2619217 A1 | 2/2007 |
| CA | 2605078 A1 | 1/2013 |
| CN | 1308533 A | 8/2001 |
| CN | 1617720 A | 5/2005 |
| CN | 1735604 A | 2/2006 |
| CN | 101677564 A | 3/2010 |
| CN | 102160865 A | 8/2011 |
| CN | 102772404 A | 11/2012 |
| CN | 102802418 A | 11/2012 |
| EP | 0186087 A1 | 7/1986 |
| EP | 2156833 A1 | 2/2010 |
| EP | 1453505 B1 | 9/2010 |
| EP | 2305252 A1 | 4/2011 |
| EP | 2465500 A | 6/2012 |
| EP | 2497472 A1 | 9/2012 |
| EP | 2497473 A1 | 9/2012 |
| EP | 2497474 A1 | 9/2012 |
| EP | 2542541 A | 1/2013 |
| EP | 2246053 B1 | 9/2013 |
| JP | 61-155377 | 7/1986 |
| JP | H07504655 A | 5/1995 |
| JP | 10-510809 A | 10/1998 |
| JP | 2006-143708 | 6/2006 |
| JP | 2010-031059 A | 2/2010 |
| JP | 2010-513316 A | 4/2010 |
| JP | 4500543 | 4/2010 |
| JP | 11-515012 A | 5/2011 |
| RU | 2009 126742 A | 1/2011 |
| WO | WO 1993/017683 A1 | 9/1993 |
| WO | WO 1993/024834 A1 | 12/1993 |
| WO | WO 1996/018395 A | 6/1996 |
| WO | WO 1997/015304 A1 | 5/1997 |
| WO | WO 1998/059360 A1 | 12/1998 |
| WO | WO 2001/013902 A2 | 3/2001 |
| WO | WO 2001/022820 A1 | 4/2001 |
| WO | WO 2001/062249 A1 | 8/2001 |
| WO | WO 2003/049705 A2 | 6/2003 |
| WO | WO 03/070188 A2 | 8/2003 |
| WO | WO 2004/002520 A1 | 1/2004 |
| WO | WO 2004/010999 A1 | 2/2004 |
| WO | WO 2004/026246 A2 | 4/2004 |
| WO | WO 2004/041797 A1 | 5/2004 |
| WO | WO 2004/050034 A2 | 6/2004 |
| WO | WO 2004/058163 A2 | 7/2004 |
| WO | WO 2005/011687 A1 | 2/2005 |
| WO | WO 2005/092871 A2 | 10/2005 |
| WO | WO 2005/123193 A2 | 12/2005 |
| WO | WO 2006/003471 A2 | 1/2006 |
| WO | WO 2006/012277 A | 2/2006 |
| WO | WO 2006/015943 A2 | 2/2006 |
| WO | WO 2006/015944 A2 | 2/2006 |
| WO | WO 2006/043532 A1 | 4/2006 |
| WO | WO 2006/076681 A2 | 7/2006 |
| WO | WO 2006/116369 A2 | 11/2006 |
| WO | WO 2007/022182 A1 | 2/2007 |
| WO | WO 2007/045620 A | 4/2007 |
| WO | WO 2007/075095 A1 | 7/2007 |
| WO | WO 2007/076062 A2 | 7/2007 |
| WO | WO 2007/090882 A2 | 8/2007 |
| WO | WO 2007/121188 A | 10/2007 |
| WO | WO 2007/137071 A2 | 11/2007 |
| WO | WO 2008/023027 A2 | 2/2008 |
| WO | WO 2008/041240 A1 | 4/2008 |
| WO | WO 2008/052953 A1 | 5/2008 |
| WO | WO 2008/074033 A1 | 6/2008 |
| WO | WO 2005/070188 A2 | 8/2008 |
| WO | WO 2008/104847 A2 | 9/2008 |
| WO | WO 2008/113003 A1 | 9/2008 |
| WO | WO 2008/113056 A2 | 9/2008 |
| WO | WO 2010/022140 A1 | 2/2010 |
| WO | WO 2010/148409 A1 | 12/2010 |
| WO | WO 2011/109596 A1 | 9/2011 |
| WO | WO 2011/150221 A2 | 12/2011 |
| WO | WO 2012/019015 A2 | 2/2012 |
| WO | 2013034550 A1 | 3/2013 |
| WO | WO 2013/096816 A1 | 6/2013 |
| WO | WO 2013/096870 A1 | 6/2013 |
| WO | WO 2014/134569 A1 | 9/2014 |
| WO | WO 2015/006708 A1 | 1/2015 |
| WO | WO 2015/0018397 A1 | 1/2015 |
| WO | WO 2015/023786 A1 | 2/2015 |
| WO | WO 2015/023790 A1 | 2/2015 |

OTHER PUBLICATIONS

Anosova et al. "Antigenecity and Immunogenicity of Allogeneic Retinal Transplants" Oct. 2001, J. Clin. Invest. 108(8):1175-1183.

Ansel et al. "Pharmaceutical Dosage Forms and Drug Delivery Systems, $6^{th}$ ed." 1995, Williams and Wilkins Media, Malvern, PA (TOC).

Anthony et al. "Protective Immune Mechanisms in Helminth Infection" Dec. 2007, Nat Rev Immunol. 7(12):975-987.

Asgeirsson et al. "Hereditary cystatin C amyloid angiopathy: monitoring the presence of the Leu-68→Gln cystatin C variant in cerebrospinal fluids and monocyte cultures by MS" 1998, Biochem. J, 329 (Pt 3):497-503 (1998).

Ashcroft et al. "An Efficient and Scalable Synthesis of the Endothelin Antagonists UK-350,926 and UK-349,862 Using a Dynamic Resolution Process" 2005, Organic Proc. Res. & Dev. 9:663-669.

Balicki et al. "A New, Efficient and Economic Method for Preparation of Pramipexole" May 16, 2006, Book of Abstracts: The Fifth Multidisciplinary conference on Drug Research, Pielaszek Research (Warszawa, Poland) Poster No. 1-19, p. 30 (English Abstract).

Balicki et al. "New method for preparing pramipexole dihydrochloride monohydrate" 2006, Przemysl Chemiczny 85(5):344-346.

Banker et al. "Modern Pharmaceutics" 1979, Marcel Dekker, Inc. (TOC).

Beal "Oxidative Metabolism" 2000, Ann. N.Y. Acad. Sci. 924:164-169.

Beatty et al. "The Role of Oxidative Stress in the Pathogenesis of Age-Related Macular Degeneration" 2000, Surv. Opthalmol 45(2):115-134.

Benson et al. "Identification of carriers of a variant plasma prealbumin (transthyretin) associated with familial amyloidotic polyneuropathy type J" 1985, J. Clin. Invest. 74:71-75.

Berge et al. "Pharmaceutical Salts" 1977, J. Pharm. Sciences 66(1):1-19.

Bergen et al. "Identification of transthyretin variants by sequential proteomic and genomic analysis" 2004, Clin. Chem. 50(9):1544-1552.

Bernstein et al. "Transythyretin: Its response to malnutrition and stress injury. Clinical usefulness and economic implications" Dec. 2002, Clin. Chem. Lab. Med. 40(12):1344-1348.

Biglan et al. "A Review of Pramipexole and its Clinical Utility in Parkinson's Disease" 2002, Expert Opinion Pharmacotherapy 3(2):197-210.

Borchelt et al. "Superoxide dismutase 1 with mutations linked to familial amyotrophic lateral sclerosis possesses significant activity" 1994, PNAS USA 91(17):8292-8296.

Bozik et al. "Safety, Tolerability, and Pharmacokinetics of KNS-760704 (Dexpramipexole) in Healthy Adult Subjects" 2011, J. Clin. Pharmacol. 51:1177-1185.

(56) References Cited

OTHER PUBLICATIONS

Bozik et al. "Phase 2 Study of the Safety, Tolerability and Clinical Effects of KNS 760704 in ALS Subjects" Dec. 2009, 20th International Symposium on ALS/MND Abstract C40.
Carvey, et al. "Attenuation of levodopa-induced toxicity in mesencephalic cultures by pramipexole" 1997, J. Neural. Transm. 209-228.
Cassarino et al. "An evaluation of the role of mitochondria in neurodegenerative diseases: mitochondrial mutations and oxidative pathology, protective nuclear responses, and cell death in neurodegeneration" 1999, Brain Res. Rev. 29:1-25.
Cassarino et al. "Cyclosporin A increases resting mitochondrial membrane potential in SY5Y cells and reverses the depressed mitochondrial membrane potential of Alzheimer's disease cybrids" May 13, 1998, Biochem. and Biophysical Research Comm. 248:168-173.
Cassarino et al. "Interaction among mitochondria, mitogen-activated protein kinases, and nuclear factor-kappaB in cellular models of Parkinson's disease" Apr. 2000, J Neurochem. 74(4):1384-92. PubMed PMID: 10737593.
Cassarino et al. "Pramipexole reduces reactive oxygen species production in vivo and in vitro and inhibits the mitochondrial permeability transition produced by the parkinsonian neurotoxin methylpyridinium ion" 1998, J. Neurochem. 71(1):295-301.
Cleveland et al. "From Charcot to Lou Gehrig: deciphering selective motor neuron death in ALS" Nov. 2001, Nature 2:806-819.
Corcoran et al. "Absence of retinoids can induce motoneuron disease in the adult rat and a retinoid defect is present in motoneuron disease patients" 2002, J. Cell. Sci. 115:4735-4741.
Corrigan et al. "Comparison of Pramipexole, Fluoxetine, and Placebo in Patients with Major Depression" 2000, Depression and Anxiety 11:58-65.
Cudkowicz et al. "Measures and Markers in Amyotrophic Lateral Sclerosis" Apr. 2004, NeuroRx: The Journal of the American Society for Experimental NeuroTherapeutics 1(2):273-283.
Danzeisen et al. "Targeted Antioxidative and Neuroprotective Properties of the Dopamine Agonist Pramipexole and Its Nondopaminergic Enantiomer SND919CL2x [(+)2-Amino-4, 5, 6, 7-tetrahydro-6-L-propylamino-benzathiazole Dihydrochloride]" 2006, J. Pharmacol. Exp. Ther. 316:189-199.
Davis et al. "Eosinophils and Cancer" Aug. 20, 2014, Cancer Immunol Res. 2(1):1-8-p. 5.
Declaration of James P. Bennett Under 37 C.F.R. 1.132 dated Dec. 15, 2009.
Deigner et al. "Apoptosis Modulators in the Therapy of Neurodegenerative Diseases" Apr. 2000, Ex. Opin. Investigational Drugs 9(4):747-764 XP001012423.
Deng et al. "Elevation of cystatin C in susceptible neurons in Alzheimer's disease" Sep. 2001, Am. J. Pathol. 159(3):1061-1068.
Dooley et al. "Pramipexole. A Review of its Use in the Managemetn of Early and Advanced Parkinson's Disease" Jun. 1998, Drugs Aging 12(6):495-514.
Drobny et al. "Possible Extrapyramidal System Degradation in Parkinson's Disease" 2000, Brain Research Bulletin 53(4):425-430.
Email correspondence from James P. Bennett to Michael Bozik dated May 11, 2006 with a presentation entitled "ALS: An Investigator's View of the Disease and its Treatment".
Email correspondence from James P. Bennett to Michael Bozik dated Oct. 9, 2006 with a draft grant application.
Email correspondence from James P. Bennett to Michael Bozik dated Apr. 6, 2007 with a draft manuscript entitled "R(+) Pramipexole as a Neuroprotectant I: Effects of R(+) Pramipexole Treatment of ALS on ALSFRSr, Forced Vital Capacity and Neurophysiological Index".
Email correspondence from James P. Bennett to Michael Bozik dated Apr. 6, 2007 with a draft manuscript entitled "R(+) Pramipexole as a Neuroprotectant II: Tolerability and Pharmacokinetics in ALS of Esclating Doses to 300mg/day".
European Seach Report and Opinion dated Aug. 1, 2012 for EP 12163888.
European Search Report and Opinion dated Aug. 2, 2012 for EP 12164060.
European Search Report and Opinion dated May 10, 2012 for EP 11186875.
European Search Report dated Feb. 18, 2011 for EP10009931.
European Search Report dated Mar. 2, 2011 for EP 10075571.9.
European Supplemental Search Report dated Apr. 8, 2010 for EP 08743922.
European Supplemental Search Report dated Apr. 9, 2010 for EP 08732306.9.
European Supplemental Search Report dated Nov. 23, 2006 for EP 02795869.
European Supplemental Search Report dated Oct. 4, 2010 for EP 10008579.4.
Extended European Search Report and Written Opinion dated Sep. 11, 2012 for EP 12164067.
Extended European Supplemental Search Report and Written Opinion dated Feb. 18, 2011 for EP10075571.
Feher et al. "Mitochondrial alternations of retinal pigment epithelium in age-related macular degenteration" Jun. 2006 (Printed from http://www.neurobiologyofaging.org/article/PIISO1974580005001545 on Dec. 11, 2009) Neurobiology of Aging 27(7) (Abstract, 2 pages).
Ferger et al. "The dopamine agonist pramipexole scavenges hydroxyl free radicals induced by striatal application of 6-hydroxydopamine in rats: an in vivo microdialysis study" Aug. 29, 2000, Brain Research 883:216-223.
Gennaro "Remington: The Science and Practice of Pharmacy, $20^{th}$ Ed." Lippincott Williams & Wilkins, Baltimore, MD, 2000, Ch. 38:704-720.
Golebiewski et al. "Application of GC/MS for Identyfication of the Sideproducts in a Process of Preparation of Pramipexole" May 16, 2006, Book of Abstracts: The Fifth Multidisciplinary conference on Drug Research, Pielaszek Research (Warszawa, Poland) Poster No. 1-57, p. 49.
Goodall et al. "Association of the H63D polymorphism in the hemochromatosis gene with sporadic ALS" 2005, Neurology 65(6):934-937.
Goodman et al. "The Pharmaceutical Basis of Therapeutics, $6^{th}$ Ed." 1980, MacMillan Publishing Co., New York (TOC).
Gu et al. "Pramipexole protects against apoptotic cell death by non-dopaminergic mechanisms" 2004, J. Neurochem. 91:1075-1081.
Gurney et al. "Benefit of Vitamin E, Riluzole, and Gabapentin in a Transgenic Model of Familial Amyotrophic Lateral Sclerosis" Feb. 1996, Ann. Neurol. 39(2):147-157.
Gurney et al. "Motor Neuron Degeneration in Mice That Express a Human Cu, Zn Superoxide Dismutase Mutation" Jun. 17, 1994, Science 264:1772-1775.
Haghikia et al. "Therapies for multiple sclerosis: translation achievements and outstanding needs" May 2013 Trends in Moleecular Medicine 19(5):309-319.
Halestrap "The Role of Mitochondria in Cell Death" Mar. 24, 2003, Endocrine Abstracts 5:513 (Abstract).
Hall et al. "Brain hydroxyl radical generation in acute experimental head injury" Feb. 1993, J. Neurochem. 60(2):588-594.
Hall et al. "Neuroprotective effects of the dopamine $D_2 / D_3$ agonist pramipexole against postischemic or methamphetamine-induced degeneration of nigrostriatal neurons" Aug. 6, 1996, Brain Research 742:80-88 (abstract).
Hansen et al. "First Generation Process for the Preparation of the DPP-IV Inhibitor Sitagliptin" 2005, Organic Proc. Res. & Dev. 9:634-639.
Hardy et al. "Genetic Classification of Primary Neurodegenerative Disease" Nov. 6, 1998, Science 282(5391):1075-1079.
Hasegawa et al. "A New Process for Synthesis of the Astrcyte Activation Suppressor, ONO-2506" 2005, Organic Proc. Res. & Dev. 9:774-781.
Hubble Pre-clinical Studies of Pramipexole: Clinical Relevance May 2000 Eur. J. Neurol. 7(Supp 1):15-20.

(56) References Cited

OTHER PUBLICATIONS

Initial Scientific Discussion for the Approval of Mirapex from the European Agency for the Evaluation of Medicinal Products (EMEA), 2005, www.emea.europa.eu/humandocs/PDFS/EPAR/Mirapexin/059097en6.pdf.
International Search Report and Written Opinion for PCT/US2008/057158 dated Jun. 29, 2009.
International Search Report and Written Opinion for PCT/US2010/39379 dated Aug. 25, 2010.
International Search Report and Written Opinion for PCT/US2013/054804 dated Mar. 21, 2014.
International Search Report and Written Opinion for PCT/US2014/019668 dated Jun. 9, 2014.
International Search Report and Written Opinion for PCT/US2014/050951 dated Oct. 22, 2014.
International Search Report and Written Opinion for PCT/US2014/050943 dated Nov. 6, 2014.
International Search Report for PCT/US2002/39970 dated Jul. 17, 2003.
International Search Report for PCT/US2006/031831 dated Dec. 12, 2006.
International Search Report for PCT/US2007/087639 dated Apr. 4, 2008.
International Search Report for PCT/US2008/057059 dated Jul. 11, 2008.
International Search Report for PCT/US2009/54292 dated Oct. 22, 2009.
International Search Report for PCT/US2011/38159 dated Dec. 12, 2011.
International Search Report for PCT/US2014/046380 dated Dec. 10, 2014.
Jacques et al. "Enantiomers, Racemates and Resolutions" 1981, John Wiley and Sons, Inc., New York (TOC).
Johnson et al. (Relationships between drug activity and NCI preclinical in vitro and in vivo models and early clinical trials; British Journal of Cancer; (2001) 84 (10), 1424-1431).
Kamel et al. "Lead exposure and amyotrophic lateral sclerosis" May 2002, Epidemiology 13(3):311-319.
Kato et al. "A neurosphere-derived factor, cystatin C, supports differentiation of ES cells into neural stem cells" Apr. 11, 2006, PNAS USA 103(15):6019-6024.
Khan et al. "Alzheimer's disease cybrids replicate beta-amyloid abnormalities through cell death pathways" Aug. 2000, Ann Neurol. 48(2):148-55. PubMed PMID: 10939564.
Kieburtz "Safety and Efficacy of Pramipexole in Early Parkinson Disease" 1997, JAMA 278(2):125-130.
Kitamura et al. "Protective Effects of the Antiparkinsonian Drugs Talipexole and Pramipexole against 1-Methyl-4-phenylpyridinium-Induced Apoptotic Death in Human Neuroblastoma SH-SY5Y Cells" 1998, Molecular Pharmacology 54:1046-1054.
Lahortiga et al. "Activity of imatinib in systemic mastocytosis with chronic basophilic leukemia and a PRKG2-PDGFRB fusion" 2008, Haematological/The Hematology Journal 93(1): 51-52, 55.
Le et al. "Antioxidant property of pramipexole independent of dopamine receptor activation in neuroprotection" 2000, J. Neural. Transm. 107(10):1165-73.
Lee et al. "Carcinogenicity Predictions for a Group of 30 Chemicals Undergoing Rodent Cancer Bioassays Based on Rules Derived from Subchronic Organ Toxicities" Oct. 1996, Environmental Health Perspectives 104(5):1059-1063.
Levy et al. "Stroke in Icelandic Patients With Hereditary Amyloid Angiopathy is Related to a Mutation in the Cystatin C Gene, An Inhibitor of Cysteine Proteases" May 1989, J. Exp. Med. 169(5):1771-1778.
Liang et al. "Oxidative stress-induced mitochondrial DNA damage in human retinal pigment epithelial cells: a possible mechanism for RPE aging and age-related macular degeneration" Apr. 1, 2003, Exp. Eye Res. 76(4):397-403.

Lieberman et al. "Clinical evaluation of pramipexole in advanced Parkinson's disease: Results of a double-blind, placebo-controlled, parallel-group study" 1997, Neurology 49:162-168.
Lieberman et al. "Pharmaceutical Dosage Forms: Disperse Systems" 1996, Marcel Dekker, Inc., New York vol. 2 (TOC).
Lieberman et al. "Pharmaceutical Dosage Forms: Tablets" 1989, Marcel Dekker, Inc., New York vol. 1 (TOC).
Lin et al. "Large-scale protein identification using mass spectrometry" 2003, Biochimica et Biophysica Acta 16460(2):1-10.
Lofberg, et al. "Immunohistochemical characterization of the amyloid deposits and quantitation of pertinent cerebrospinal fluid proteins in hereditary cerebral hemorrhage with amyloidosis" Mar.-Apr. 1987, Stroke 18(2):431-440.
Lomen-Hoerth "Amyotrophic lateral sclerosis from bench to bedside" 2008, Semin. Neurol. 28(2):205-211.
Love "Oxidative Stress in Brain Ischemia" Apr. 5, 1999, Brain Pathology 9(1)119-131 (Abstract).
Malaspina et al. "Differential expression of 14 genes in amyotrophic lateral sclerosis spinal cord detected using gridded eDNA arrays" 2001, J. Neurochemistry 77(1):132-145.
Martens "Cloning and Sequence Analysis of Human Pituitary eDNA Encoding the Novel Polypeptide 7B2" Jul. 1988, FEBS Letters 234(1):160-164.
Martens et al. "The novel pituitary polypeptide 7B2 is a highly-conserved protein coexpressed with proopiomelanocortin" Apr. 1989, Eur. J. Biochem. 181(1):75-79.
Matthews et al. "Assessment of the Health Effects of Chemicals in Humans: I. QSAR Estimation of the Maximum Recommended Therapeutic Dose (MRTD) and No Effect Level (NOEL) of Organic Chemicals Based on Clinical Trial Data" 2004, Current Drug Discovery Technologies 1:61-76.
Mbikay et al. "Neuroendocrine secretory protein 7B2: structure, expression and functions" Jul. 15, 2001, Biochem. J. 357(2):329-342.
Menzies et al. "Mitochondrial dysfunction in a cell culture model of familial amyotrophic lateral sclerosis" Jul. 2002, Brain 125(7):1522-1533.
Merck Manuals Online Medical Library, Age-Related Macular Degeneration (ARMD), 2005, printed Aug. 13, 2008 from http://www.merck.com/mmpe/print/sec09/ch106/ch106b.html, 2 pages.
Mey et al. "Retinoic acid signaling in the nervous system of adult vertebrates" 2004, Neuroscientist 10(5):409-421.
Mhatre et al. "Oxidative Stress and Neuroinflammation in Alzheimer's Disease and Amyotrophic Lateral Sclerosis; Common Links and Potential Therapeutic Targets" Apr. 2004, J. Alzheimers Dis. 6(2):147-157 (abstract only).
Mierau et al. "Pramipexole binding and activation of cloned and expressed dopamine $D_2$, $D_3$ and $D_4$ receptors" 1995, Eur. J. Pharmacol. 290:29-36.
Miklya et al. "A pharmacological analysis elucidating why, in contrast to (−)-deprenyl (selegiline), α-tocopherol was ineffective in the DATATOP study" 2003, Life Sciences 72:2641-2648.
Mirapex® Prescribing Information from Boehringer Ingelheim, 2006, http://www.biopsychiatry.com/pramipexole-mirapex.pdf (retrieved May 10, 2012).
Moore et al. "An Efficient and Operationally Convenient General Synthesis of Tertiary Amines by Direct Alkylation of Secondary Amines with Alkyl Halides in the Presence of Huenig's Base" 2005, ARKIVOC 6:287-292.
Nagai et al. "Rats expressing human cytosolic copper-zinc superoxide dismutase transgenes with amyotrophic lateral sclerosis: associated mutations develop motor neuron disease" Dec. 1, 2001, J. Neurosci. 21(23):9246-9254.
Nilsen et al. "Mitochondria as Therapeutic Targets of Estrogen Action in the Central Nervous System" Aug. 2004, Curr. Drug Targets—CNS Neurol. Disord. 3(4):297-313.
Ong et al. "An Evaluation of the Use of Two-Dimensional Gel Electrophoresis in Proteomics" 2001, Biomolecular Engineering 18(5):195-205.
Palliative (n.d.) The American Heritage® Stedman's Medical Dictionary, Retrieved Jun. 12, 2009, from Dictionary.com website: http://dictionary.reference.com/browse/palliative.

(56) References Cited

OTHER PUBLICATIONS

Paquet et al. "The neuroendocrine precursor 7B2 is a sulfated protein proteolytically processed by a ubiquitous furin-like convertase" Jul. 29, 1994, J. Biol. Chem. 269(30):19279-19285.
Pattee et al. "Reduction of oxidative stress in amyotrophic lateral sclerosis following pramipexole treatment" Jan. 2003, Amyotrophic Lateral Sclerosis and Other Motor Neuron Disorders 4(2):90-95 (abstract).
Paulson "Protein Fate in Neurodegenerative Proteinopathies: Polyglutamine Diseases Join the (Mis) Fold" 1999, Am. J. Hum. Genet. 64(2):339-345.
Petersen et al. "Impaired Mitochondrial Activity in the Insulin-Resistant Offspring of Patients with Type 2 Diabetes" 2004, New England Journal of Medicine 350:664-671.
Piercey et al. "Excitation of type II anterior caudate neurons by stimulation of dopamine $D_3$ receptors" 1997, Brain Research 762:19-28.
Piercey et al. "Inhibition of dopamine neuron firing by pramipexole, a dopamine $D_3$ receptor-prefering agonist: comparison to other dopamine receptor agonists" 1996, European J. of Pharmac. 312:35-44.
Public Statement on Mirapex, Sudden Onset of Sleep from the European Agency for the Evaluation of Medicinal Products (EMEA), Jul. 19, 1999, www.emea.europa.eu/pdfs/human/press/pus/2064299.pdf.
Ranganathan et al, "Proteomic profiling of cerebrospinal fluid identifies biomarkers for amyotrophic lateral sclerosis" Dec. 2005, J. Neurochem. 95(5):1461-1471.
Robberecht "Oxidative Stress in Amyotrophic Lateral Sclerosis" 2000, J. Neurol. 247(1):11-16 (abstract).
Roca-Santiago et al. "Alzheimer's Disease and Age-related Macular Degeneration" Feb. 2006, Arch. Soc. Esp. Oftalmol. 81(2):73-78.
Rothstein et al. "β-Lactam antibiotics offer neuroprotection by increasing glutamate transporter expression" Jan. 6, 2005, Nature 433(7021):73-77.
Rowland et al. "Amyotrophic Lateral Sclerosis" May 2001, N Eng Journal of Medicine, 344:1688-1700.
Ryberg et al. "Discovery and Verification of Amyotrophic Lateral Sclerosis Biomarkers by Proteomics" Jul. 2010, Muscle & Nerve 42(1):104-111.
Sanchez et al. "Cystatin C as a potential cerebrospinal fluid marker for the diagnosis of Creutzfeldt-Jakob disease" 2004, Proteomics 4(8):2229-2233.
Sayeed et al. "Patch Clamp Reveals Powerful Blockade of the Mitochondrial Permeability Transition Pore by the D2-Receptor Agonist Pramipexole" 2006, FASB Journal 20:556-558.
Schilling et al. "Neuroendocrine and side effect profile of pramipexole, a new dopamine receptor agonist, in humans" 1992, Clin. Pharmacol. Ther. 51:541-548.
Schmidt et al. "Neurodegenerative diseases of the retina and potential for protection and recovery" Jun. 2008 (printed from http://www.nncbi.nim.nih.gov/pubmed/19305795?dopt_Abstract) Curr. Neuropharmacol. 6(2) (Abstract, 1 page).
Schneider et al. "Dopamine Autoreceptor Agonists: Resolution and Pharmacological Activity of 2,6-Diaminotetrahydrobenzothiazole and an Aminothiazole Analogue of Apomorphine" 1987, *J. Med. Chem.* 30:494-498.
Schuelke et al. "Myostatin Mutation Associated With Gross Muscle Hypertrophy in a Child" 2004, N. Engl. J. Med. 350:2682-2688 (Para.1).
Shannon et al. "Efficacy of Pramipexole, a Novel Dopamine Agonist, as Monotherapy in Mild to Moderate Parkinson's Disease" 1997, Neurology 49(3)a;724-728.
Sousa et al. "Deposition of transthyretin in early stages of familial amyloidotic polyneuropathy: evidence for toxicity of nonfibrillar aggregates" Dec. 2001, Am. J. Pathol. 159(6):1993-2000.
Sousa et al. "Evidence for early cytotoxic aggregates in transgenic mice for human transthyretin Leu55Pro" Nov. 2002, Am. J. of Pathol. 161(5):1935-1948.
Stein et al. "Neutralization of transthyretin reverses the neuroprotective effects of secreted amyloid precursor protein (APP) in APPsw mice resulting in tau phosphorylation and loss of hippocampal neurons: Support for the amyloid hypothesis" Sep. 1, 2004, J. Neurosci. 24(35):7707-7717.
The Foundation Fighting Blindness "Animal Models for Studying Inherited Degenerative Retinal Disease" 2000 (printed from www.retina-international.org/sci-news/animmod.doc on Jan. 11, 2009) The Foundation Fighting Blindness (23 pages).
Tombran-Tink et al. "Neuroprotection in Macular Degeneration" 2005, Age-Related Macular Degeneration: A Comprehensive Textbook (Lippincott Williams & Wilkins), 29:335-336.
Tsuzuki et al. "Structure of the Human Prealbumin Gene" Oct. 5, 1984, J. Biol. Chem. 260(22):12224-12227.
Uemichi et al. "A New Mutant Transthyretin (Arg 10) Associated with Familial Amyloid Polyneuropathy" 1992, J. Med. Genet. 29:888-891.
U.S. Dept. of HHS FDA CDER (Guidance for Industry), Jul. 2005, 30 pp.
Voskoglou-Nomikos et al. (Clinical Predictive Value of the in Vitro Cell Line, Human Xenograft, and Mouse Allograft Preclinical Cancer Models; Clinical Cancer Research; vol. 9: 4227-4239; Sep. 15, 2003).
Wang et al. "R+ pramipexole as a mitochondrially focused neuroprotectant: initial early phase studies in ALS" Feb. 2008, Amyotroph Lateral Scler. 9(1):50-58. PubMed PMID: 18270879.
Wedi et al. "Chronic urticarial serum induces histamine release, leukotriene production, and basophil CD63 surface expression-inhibitory effects of anti-inflammatory drugs" Journal of allegery and clinical immunology, Mar. 2000, 105(3):552-560.
Winkler et al. "Oxidative damage and age-related macular degeneration" Nov. 3, 1999, Mol. Vis. 5:32 (Abstract).
Wong "A 384-well cell-based phosphor-ERK assay for dopamine D2 and D3 receptors" 2004, Analytical Biochem. 333:265-272.
Wong et al. "Activation of Extracellular Signal-Regulated Kinase by Dopamine D2 and D3 Receptors" 2003, Society for Neuroscience Abstracts (retrieved on line at sfn.scholarone.com/itin2003/main.html?new_page_id=126&abstract_id=3866&p_num=363.4&is_tech=0 on Jun. 23, 2008).
Worker "Novel Therapeutic Strategies" 1999, Idrugs, Current Drugs Ltd, GB 2(9):848-852 XP000972503.
Wright et al. "Influence of Probenecid (PR) and Cimetidine (C) on Pramipexole (PX) Pharmacokinetics" Feb. 1995, Clin. Pharmacol. & Ther. 59(2):PII-99 (abstract).
Written Opinion of International Search Authority dated Aug. 15, 2005 for PCT/US2006/031831.
Zheng et al. "Purification and identification of an estrogen binding protein from rat brain: oligomycin sensitivity-conferring protein (OSCP), a subunit of mitochondrial F0F1-ATP synthase/ATPase" Jan. 1999, J. Ster. Biochem. Mol. Biol. 68(1-2):65-75.
B.R. Brooks, "El Escorial World Federation of Neurology Criteria for the Diagnosis of Amyotrophic Lateral Sclerosis", 1994, Journal of the Neurological Sciences, vol. 124, Suppl., pp. 96-107.
Brooks, et al., "El Escorial revisited: Revised criteria for the diagnosis of amyotrophic lateral sclerosis", 2000, ALS and other motor neuron disorders, vol. 1, pp. 293-299.
Cudkowicz et al., "The effects of dexpramipexole (KNS-760704) in individuals with amyotrophic lateral sclerosis", Dec. 2011, Nature Medicine, vol. 17, No. 12, pp. 1652-1656; Supplemental Materials included with total of 27 pages.
Rudnicki et al., "Dexpramipexole effects on functional decline and survival in subjects with amyotrophic lateral sclerosis in a Phase II study: Subgroup analysis of demographic and clinical characteristics", Feb. 1, 2013, Amyotrophic Lateral Sclerosis and Frontotemporal Degeneration, vol. 14, pp. 44-51.
National Institutes of Health/ U.S. National Library of Medicine, "Creatine phosphokinase test", Updated Jan. 9, 2015, URL of this page: //www.nlm.nih.gov/medlineplus/ency/article/003503.htm, pp. 1-4.
Akintola-Ogunremi et al., "Chronic lymphocytic leukemia presenting with symptomatic central nervous system involvement," Ann. Hematol. (2002), (81) pp. 402-404.

(56) References Cited

OTHER PUBLICATIONS

Arico et al., Restless Legs Syndrome as the Presenting Symptom of Multiple Myeloma, Journal of Clinical Sleep Medicine (2013), 9(4) pp. 383-385.
Cudkowicz et al. "Dexpramipexole versus placebo for patients with amyotrophic lateral sclerosis (EMPOWER): a ramdomised double-blind, phase 3 trial" Lancet Neurol. (2013), (12) pp. 1059-1067.
Lucchinetti et al., "Inflammatory Cortical Demyelination in Early Multiple Sclerosis," The New England Journal of Medicine (2011), (365) pp. 2188-2197.
Meldrum "Glutamate as a Neurotransmitter in the Brain: Review of Physiology and Pathology" 2000, J. Nutr. 130:1007S-1015S.
Novelli et al. "Glutamate becomes neurotixic via the N-methyl-D-aspartate receptor when intracellular energy levels are reduced" 1988, Brain Research 451:205-212.
Rosenfeld et al. "Creatine monohydrate in ALS: Effects on strength, fatigue, respiratory status and ALSFRS" 2008, Amyotrophic Lateral Sclerosis 9:266-272.
Shefner et al. "A clinical trial of creatine in ALS" Nov. 2004, Neurology 63:1656-1661.
Vieira De Almeida et al. "Resveratrol Increases Glutamate Uptake, Glutathione Content, and S100B Secretion in Cortical Astrocyte Cultures" 2007, Cell Mol. Neurobiol. 27:661-668.
Graves, et al., "Inflammation in amyotrophic lateral sclerosis spinal cord and brain is mediated by activated macrophages, mast cells and T cells," Amyotrophic Lateral Sclerosis and Other Motor Neuron Disorders, Official Publication of the World Federation of Neurology, Research Group on Motor Neuron Diseases, Dec. 2004, 5(4):213-219.
Liou et al. ("Case Report Churg-Strauss syndrome presented as multiple intracerebral hemorrhage." Lupus [(1997);6:279-282).

* cited by examiner

COMPOSITIONS AND METHODS OF USING (R)-PRAMIPEXOLE

CROSS-REFERENCE TO RELATED APPLICATIONS

This application is a continuation of U.S. application Ser. No. 13/059,713 filed Apr. 19, 2011 entitled "Compositions and Methods of Using (R)-Pramipexole", which is a U.S. national stage filing under 35 U.S.C. §371 of International Application No. PCT/US2009/054292 filed Aug. 19, 2009 entitled "Compositions and Methods of Using (R)-Pramipexole", which claims the priority benefit of U.S. Provisional Application No. 61/090,094 filed Aug. 19, 2008 entitled "Compositions and Methods of Using (R)-Pramipexole", and U.S. Provisional Application No. 61/113,680 filed Nov. 12, 2008 entitled "Compositions and Methods of Using (R)-Pramipexole", each of which are herein incorporated by reference in their entireties.

GOVERNMENT INTERESTS

Not Applicable

PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

Not Applicable

BRIEF SUMMARY OF THE INVENTION

Various embodiments of the invention are directed to a multi-component therapeutic including a first component comprising a therapeutically effective amount of (6R)-4,5,6,7-tetrahydro-N6-propyl-2,6-benzothiazole-diamine and a second component comprising a therapeutically effective amount of one or more secondary therapeutic agents. In some embodiments, the second component may be dopamine agonists, dopaminergic agonists, COMT inhibitors, MOA inhibitors, excitatory amino acid antagonists, growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and down-regulators, monoamine oxidase type B (MOAB) inhibitors, multi-target agents, kinase inhibitors, Bcl protein inducers, histone deacetylase (HDAC) mediators, glial modulators, mitochondrial energy promoting agents, myostatin inhibitors, caspase inhibitors and combinations thereof.

Various other embodiments of the invention are directed to a method of treating a neurodegenerative disease in a patient including the steps of administering a first component comprising a therapeutically effective amount of (6R)-4,5,6,7-tetrahydro-N6-propyl-2,6-benzothiazole-diamine to the patient and administering adjunctively a second component comprising a therapeutically effective amount of one or more secondary therapeutic agents to the patient. In some embodiments, the second component may be selected from dopamine agonists, dopaminergic agonists, COMT inhibitors, MOA inhibitors, excitatory amino acid antagonists, growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and down-regulators, monoamine oxidase type B (MOAB) inhibitors, multi-target agents, kinase inhibitors, Bcl protein inducers, histone deacetylase (HDAC) mediators, glial modulators, mitochondrial energy promoting agents, myostatin inhibitors, caspase inhibitors and combinations thereof. In other embodiments, the neurodegenerative disease may be selected from Huntington's Chorea, metabolically induced neurological damage, senile dementia of Alzheimer's type, age associated cognitive dysfunction, vascular dementia, multi-infarct dementia, Lewy body dementia, neurodegenerative dementia, neurodegenerative movement disorder, ataxia, Friedreich's ataxia, multiple sclerosis, spinal muscular atrophy, primary lateral sclerosis, seizure disorders, motor neuron disorder or disease, inflammatory demyelinating disorder, Alzheimer's disease, Parkinson's disease, amyotrophic lateral sclerosis, hepatic encephalopathy, and chronic encephalitis.

BRIEF DESCRIPTION OF THE DRAWINGS

For a fuller understanding of the nature and advantages of the present invention, reference should be made to the following detailed description taken in connection with the accompanying drawings, in which.

DETAILED DESCRIPTION

Figure 1:
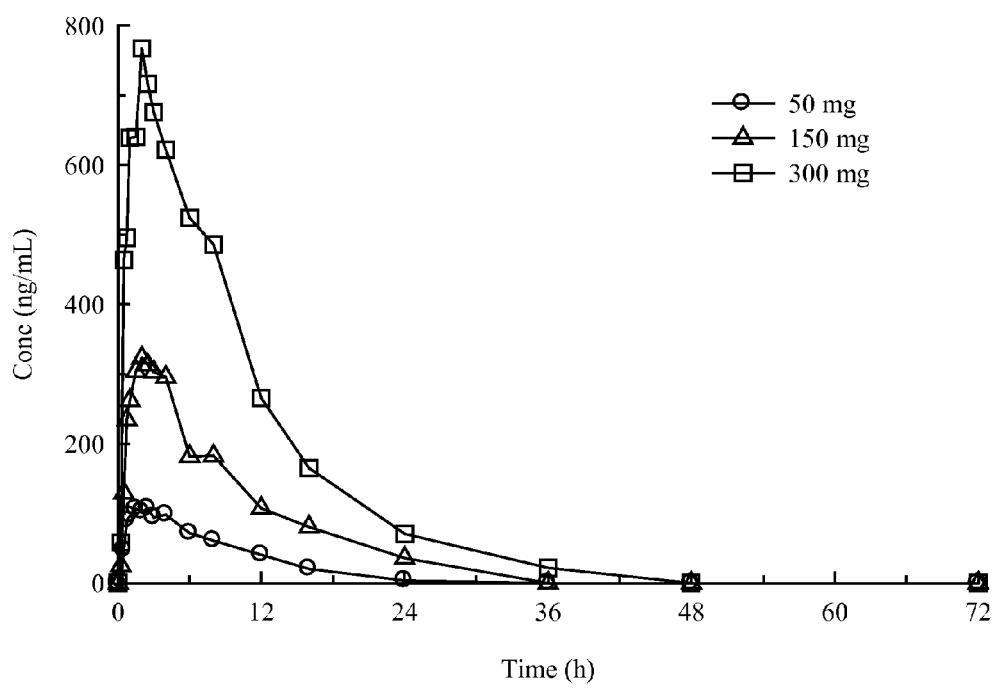
FIG. 1 depicts the mean plasma (R)-pramipexole concentrations after oral administration of single 50 mg, 150 mg, and 300 mg doses to healthy volunteers under fasted conditions.

Before the compositions and methods provided herein are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. All publications mentioned herein are incorporated by reference in their entirety to the extent to support the present invention.

It must be noted that, as used herein, and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes instances where the event occurs and instances where it does not.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by oral administration, injection, infusion, absorption or by any method in combination with other known techniques. Such combination techniques include heating, radiation and ultrasound.

The term "target", as used herein, refers to the material for which either deactivation, rupture, disruption or destruction or preservation, maintenance, restoration or improvement of function or state is desired. For example, diseased cells, pathogens, or infectious material may be considered undesirable material in a diseased subject and may be a target for therapy.

Generally speaking, the term "tissue" refers to any aggregation of similarly specialized cells which are united in the performance of a particular function.

The term "improves" is used to convey that the present invention changes either the appearance, form, characteristics and/or physical attributes of the tissue to which it is being provided, applied or administered. "Improves" may also refer to the overall physical state of an individual to whom an active agent has been administered. For example, the overall physical state of an individual may "improve" if one or more symptoms of a neurodegenerative disorder are alleviated by administration of an active agent.

As used herein, the term "therapeutic" means an agent utilized to treat, combat, ameliorate or prevent an unwanted condition or disease of a patient.

The terms "therapeutically effective amount" or "therapeutic dose" as used herein are interchangeable and may refer to the amount of an active agent or pharmaceutical compound or composition that elicits a biological or medicinal response in a tissue, system, animal, individual or human that is being sought by a researcher, veterinarian, medical doctor or other clinician. A biological or medicinal response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experienced or exhibited by the individual.

The term "unit dose" as used herein may be taken to indicate a discrete amount of the therapeutic composition which comprises a predetermined amount of the active compound. The amount of the active ingredient is generally equal to the dosage of the active ingredient which may be administered once per day, or may be administered several times a day (e.g. the unit dose is a fraction of the desired daily dose). The unit dose may also be taken to indicate the total daily dose, which may be administered once per day or may be administered as a convenient fraction of such a dose (e.g. the unit dose is the total daily dose which may be given in fractional increments, such as, for example, one-half or one-third the dosage).

As used herein, the term "neuroprotectant" refers to any agent that may prevent, ameliorate or slow the progression of neuronal degeneration and/or neuronal cell death.

The term "treating" may be taken to mean prophylaxis of a specific disorder, disease or condition, alleviation of the symptoms associated with a specific disorder, disease or condition and/or prevention of the symptoms associated with a specific disorder, disease or condition.

The term "patient" generally refers to any living organism to which to compounds described herein are administered and may include, but is not limited to, any non-human mammal, primate or human. Such "patients" may or my not be exhibiting the signs, symptoms or pathology of the particular diseased state.

As used herein, the terms "enantiomers", "stereoisomers" and "optical isomers" may be used interchangeably and refer to molecules which contain an asymmetric or chiral center and are mirror images of one another. Further, the terms "enantiomers", "stereoisomers" or "optical isomers" describe a molecule which, in a given configuration, cannot be superimposed on its mirror image.

As used herein, the terms "optically pure" or "entantiomerically pure" may be taken to indicate that a composition contains at least 99.95% of a single optical isomer of a compound. The term "entantiomerically enriched" may be taken to indicate that at least 51% of a composition is a single optical isomer or enantiomer. The term "entantiomeric enrichment" as used herein refers to an increase in the amount of one enantiomer as compared to the other. A "racemic" mixture is a mixture of equal amounts of (6R) and (6S) enantiomers of a chiral molecule.

Throughout this disclosure, the word "pramipexole" or "(S)-pramipexole" will refer to (6S) enantiomer of 2-amino-4,5,6,7-tetrahydro-6-(propylamino)benzothiazole unless otherwise specified, and (6R)-4,5,6,7-tetrahydro-N6-propyl-2,6-benzothiazole-diamine will be referred to as "(R)-pramipexole" or "RPPX."

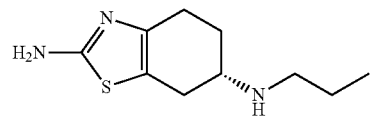

(S)-Pramipexole

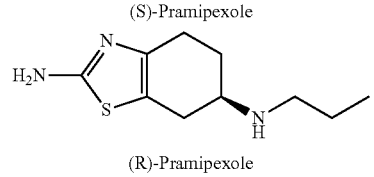

(R)-Pramipexole

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain pramipexole or a pharmaceutically acceptable salt of pramipexole as the active ingredient. Alternatively, a pharmaceutical composition may contain (R)-pramipexole or a pharmaceutically acceptable salt of (R)-pramipexole as the active ingredient.

For the purposes of this disclosure, a "salt" is any acid addition salt, preferably a pharmaceutically acceptable acid addition salt, including but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, describes pharmaceutically acceptable salts in detail.

As used herein, the term "comparative binding affinity ratio" refers to the binding affinity at the $D_2$ or $D_3$ dopamine receptors ($IC_{50}$ value) of (R)-pramipexole divided by the binding affinity at the $D_2$ or $D_3$ dopamine receptors ($IC_{50}$ value) of (S)-pramipexole. In some embodiments, the comparative binding affinity ratio refers to the ratio of the $IC_{50}$ values at the $D_2$ receptor. In some embodiments, the comparative binding affinity ratio refers to the ratio of the $IC_{50}$ values at the $D_3$ receptor.

As used herein, the term "comparative ratio" refers one of the following: 1) the ratio of the $IC_{50}$ values at the $D_2$ or $D_3$ receptors for (R)-pramipexole to (S)-pramipexole; 2); the ratio of MTD amounts for (R)-pramipexole to (S)-pramipexole; or 3) the ratio of NOAEL dose amounts for (R)-pramipexole to (S)-pramipexole.

As used herein, the term "daily dose amount" refers to the amount of pramipexole per day that is administered or prescribed to a patient. This amount can be administered in multiple unit doses or in a single unit dose, in a single time during the day or at multiple times during the day.

As used herein, the term "dopaminergic activity equivalent" (DAE) refers to the measure of activity at the dopamine receptors which is equivalent to the activity of 1 mg of (S)-pramipexole at the dopamine receptors.

A "dose amount" as used herein, is generally equal to the dosage of the active ingredient which may be administered once per day, or may be administered several times a day (e.g. the unit dose is a fraction of the desired daily dose). For example, a non-effective dose amount of 0.5 mg/day of (S)-pramipexole may be administered as 1 dose of 0.5 mg, 2 doses of 0.25 mg each or 4 doses of 0.125 mg. The term "unit dose" as used herein may be taken to indicate a discrete amount of the therapeutic composition which comprises a predetermined amount of the active compound. The amount of the active ingredient is generally equal to the dosage of the active ingredient which may be administered once per day, or may be administered several times a day (e.g. the unit dose is a fraction of the desired daily dose). The unit dose may also be taken to indicate the total daily dose, which may be administered once per day or may be administered as a convenient fraction of such a dose (e.g. the unit dose is the total daily dose which may be given in fractional increments, such as, for example, one-half or one-third the dosage).

As used herein, the terms "enantiomers", "stereoisomers" and "optical isomers" may be used interchangeably, and refer to molecules which contain an asymmetric or chiral center and are non-superimposable mirror images of one another. As used herein, the term "chirally pure" or "enantiomerically pure" may be taken to indicate that the compound contains at least 99.95% of a single optical isomer. The term "enantiomerically enriched", unless a number is mentioned, may be taken to indicate that at least 51% of the material is a single enantiomer. The term "enantiomeric enrichment" as used herein refers to an increase in the amount of one enantiomer as compared to the other. A "racemic" mixture is a mixture of equal amounts of (R)- and (S)-enantiomers of a chiral molecule.

As used herein, a "kit" refers to one or more pharmaceutical compositions and instructions for administration or prescription of the one or more compositions. The instructions may consist of product insert, instructions on a package of one or more pharmaceutical compositions, or any other instruction.

As used herein, the term "Mirapex®" refers to tablets containing (S)-pramipexole dihydrochloride, which has the chemical name, (S)-2-amino-4,5,6,7-tetrahydro-6-(propylamino)benzothiazole dihydrochloride monohydrate.

As used herein, the term "naïve patient" refers to a patient that has not previously received pramipexole treatment (either (R)-pramipexole or (S)-pramipexole) or who has not received a titration regimen of pramipexole previous to receiving a starting dose of pramipexole.

As used herein, the term "starting daily dose amount" refers to the amount of pramipexole per day that is administered or prescribed to a patient beginning pramipexole treatment, who has not previously been subjected to a titration regimen of pramipexole. This amount can be administered in multiple unit doses or in a single unit dose, in a single time during the day or at multiple times during the day.

By "adjunctive administration" or "adjunctively" is meant simultaneous administration of more than one compound, in the same dosage form, simultaneous administration in separate dosage forms, and separate administration of the more than one compound. For example, secondary pharmaceutical compositions such as a dopaminergic agonists and/or an antioxidant may be adjunctively administered with (R)-pramipexole where the (R)-pramipexole, the dopaminergic agonists, and the antioxidant are all in separate dosage forms such as 3 individual tablets, or a dopaminergic agonist and/or an antioxidant my be adjunctively administered with (R)-pramipexole in a single dosage form such as a single tablet. As such, each individual pharmaceutical composition may further include one or more pharmaceutically acceptable excipients or carriers.

The term "trituration" may be taken to indicate a method of solidifying a chemical compound. Trituration involves agitating the compound by stirring, beating or a method of the like until the chemical compound forms a crystalline solid or precipitate. This solid may act to seed the remaining chemical compound in solution, causing it to precipitate or crystallize from solution.

(R)-pramipexole is an enantiomer of the active pharmaceutical ingredient of the approved Parkinson's disease (PD) and restless legs syndrome (RLS) treatment Mirapex (pramipexole; (S)-pramipexole). Mirapex® is a high-affinity (low nM $IC_{50}$) agonist at human and rodent recombinant dopamine $D_2$ and $D_3$ receptors, a property that is the pharmacological basis of its efficacy in these disorders. Both the (R)- and the (S)-enantiomers have been shown preclinically to possess neuroprotective properties that are independent of dopamine receptor affinity.

Neuroprotective properties of (S)-pramipexole have been recognized as potentially useful for the treatment of neurodegenerative disorders, but clinical experience with the drug for treatment of dopamine deficiency disorders, such as PD, have shown that dosing is limited both temporally, by the need for prolonged dose titration, and absolutely, in terms of maximum tolerated dose (MTD), due to dopamine agonist-related side effects. These dosing limitations are typical for dopamine receptor agonists of this class:

The maximum allowable single starting dose for Mirapex® is 0.125 mg, given three times a day (t.i.d.); and the maximum allowable dose for Mirapex is 1.5 mg t.i.d., providing a maximum daily dose of 4.5 mg of Mirapex® after 7-8 weeks of titration.

While these dose levels of Mirapex® are useful for treatment of the signs and symptoms of PD and RLS, in neuroprotective assays the potency of (S)-pramipexole as a neuroprotective is approximately 1000-fold lower than its potency as a dopamine agonist. This suggests the therapeutically useful neuroprotective doses cannot be reached using this enantiomer.

(R)-pramipexole possesses similar neuroprotective potency, but lower affinity for dopamine receptors. Accordingly, it has been advanced as a potentially more useful compound for treatment of neurodegenerative disorders. However, previously reported dopamine receptor affinity difference for the (R)-pramipexole compared to (S)-pramipexole would still impose clinically important dose limitations and would still require dose-titration and dose-limitations to avoid dopamine-related side effects. In previous reports utilizing (R)-pramipexole in amyotrophic lateral sclerosis (ALS), a rapidly progressing fatal neurodegenerative disorder, dosing of (R)-pramipexole was suggested to be limited and to require significant dose-titration in animal experiments. The assumed requirement for dose-titration-specifically, the requirement to start dosing at very low doses and increase the dose to a final therapeutically effective dose level over 7-8 weeks-severely limits the usefulness of the neuroprotective potential of the (R)-pramipexole enantiomer. Additionally, the assumed MTD would severely limit the timely exploitation of the neuroprotective potential of the (R)-pramipexole enantiomer.

Various embodiments of the invention presented herein are directed to a multi-component system including (R)-pramipexole and one or more secondary agents, pharmaceutical compositions including (R)-pramipexole and one or more secondary agents, and methods for treating a disease in a subject including the steps of administering (R)-pramipexole and one or more secondary agents. The components of the multi-component system may be administered individually or in combined into a single dosage formula. Therefore, some embodiments of the invention are directed to a pharmaceutical compositions including (R)-pramipexole and one or more secondary agents and a pharmaceutically acceptable excipient or carrier and methods for using such pharmaceutical compositions.

The secondary agents of embodiments may be any agent that when combined with (R)-pramipexole produces a beneficial effect. For example, in some embodiments, the secondary agent may include one or more dopaminergic agonists, catechol-O-methyl transferase (COMT) inhibitors, monoamine oxidase (MOA) inhibitors, excitatory amino acid antagonists and combinations thereof. In other embodiments, the secondary agent may include growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and downregulators, monoamine oxidase type B (MOAB) inhibitors, multi-target agents, kinase inhibitors, B-cell lymphoma (Bcl) inducers, histone deacetylase (HDAC) inhibitors, glial modulators, mitochondrial energy promoting agents, myostatin inhibitors, caspase inhibitors and combinations thereof. Embodiments of the invention are not limited to any particular agent encompassed by the classes of agents described above, and any agent that falls within any of these categories may be utilized in embodiments of the invention. Non-limiting examples, of such agents are provided for clarity.

For example, in some embodiments, exemplary dopamine agonists may include, but are not limited to, apomorphine, carbidopa/levodopa, bromocriptine, lisuride, cabergoline and piribedel, and in particular embodiments, the dopamine agonists may be D2/D3 agonists such as, but nor limited to pramipexole ((6S)-4,5,6,7-tetrahydro-N6-propyl-2,6-benzothiazole-diamine) (e.g., Mirapex®), ropinirole (e.g., Requip®), carbidopa, levodopa, entacapone (e.g., COMtan®), carbidopa/levodopa (e.g., Sinemet®), carbidopa/levodopa/entacapone (e.g. Stalevo®), selegiline (e.g., Eldpryyl®), rotigotine (e.g., Neupro®), rasagaline (e.g., Azilect®), apomorphine (e.g., Apokyn®), bromocriptine (e.g., Parlodel®), amantadine (e.g., Symmetrel®) paliroden, xaliproden, talampanel and combinations thereof. Without wishing to be bound by theory, in such embodiments, (R)-pramipexole may exert a neuroprotective effect while a D2/D3 agonists may activate dopamine receptors. In further embodiments, exemplary dopaminergic agonists may include, but are not limited to, ropinirole, rotigotine, pergolide, amantadine. In other embodiments, exemplary COMT inhibitors may include, but are not limited to, entacapone and tolcapone. In still other embodiments, exemplary MOA inhibitors may include, but are not limited to, selegiline, rasagiline moclobemide, isocarboxazid, phenelzine, tranylcypromine, nialamide, iproniazid, iproclozide, toloxatone, linezolid, dextroamphetamine, EVT 302 (Evotec, Inc.), Ro 19-6491 (Hoffman-La Roche, Inc.), Ro 19-6327 (Hoffman-La Roche, Inc.), deprenyl, pargyline and ladostigil (TV-3326), and in yet other embodiments, exemplary excitatory amino acid antagonists may include, but are not limited to, talampanel.

In further embodiments, exemplary growth factors and neurotrophic factors may include, but are not limited to, insulin-like growth factor-1 (IGF-1), IGF-1 AAV, IPLEX, glial cell line-derived neurotrophic factor (GDNF), hepatocyte growth factor (HGF), and granulocyte colony stimulating factor(G-CSF). In some embodiments, exemplary antioxidants, anti-inflammatories, and immunomodulators may include, but are not limited to, AEOL 10150, cefriaxone, celastrol, coenzyme Q10, copaxone, cox-2 inhibitors (including nimesulide), cyclosporin, ebselen, edaravone (radicut), promethazine, tamoxifen, thalidomide, vitamin E and VP025, and in other embodiments, exemplary AMPA receptor antagonists may include, but are not limited to, 1,2,3,4-tetrahydro-6-nitro-2,3-dioxo-benzo[f]quinoxaline-7-sulfonamide (NBQX) and talampanel. In still other embodiments, exemplary heat shock protein inducers/protein disaggregators and downregulators include, but are not limited to, arimoclomol, ISIS 333611, lithium, misfolded SOD-1 antibodies, rhHSP70, TDP-43 antagonists and trehalose, and in yet other embodiments, exemplary MOAB inhibitors may include, but are not limited to rasagiline [R(+)N-propargyl-1-aminoindan].

In particular embodiments, exemplary multi-target agents may include, but are not limited to, 4-[2(aminomethyl)-1,3-thiazol-4-yl]-2,6 di-tert-butylphenol, and in some embodiments, exemplary kinase inhibitors may include, but are not limited to, olomoucine, quinolin-2(1H)-one derivatives, roscovitine, tamoxifen and combinations thereof. In other embodiments, exemplary Bcl inducers include, but are not limited to, ginsenoside Rb1 and Rg1, G3139, oblimersen and combinations thereof, and in further embodiments, exemplary HDAC mediators may include, but are not limited to, phenylbutyrate, scriptaid, valproic acid and combinations thereof. In still other embodiments, exemplary glial modulators include, but are not limited to, ONO-2506, and in yet other embodiments, exemplary mitochondrial energy promoter agents may include, but are not limited to, resveratrol, creatine, erythropoietin, cholest-4-en-3-One, and oxime (TRO-19622). In still further embodiments, exemplary myostatin inhibitors may include, but are not limited to, ACE-031, MYO-029 and combinations thereof, and in certain embodiments, exemplary caspase inhibitors may include, but are not limited to, ESPA-1002, IDN-6556, pralnacasan and combinations thereof.

Any of the secondary agents described above may be useful in embodiments of the invention. However, in particular embodiments, the secondary agent may be a dopamine agonist. For example, in one exemplary embodiment, the dopamine agonist may be ropinirole (Requip®), and in another exemplary embodiment, the dopamine agonist may be carbidopa/levodopa (Sinemet®). In other particular embodiments, the secondary agent may be an anti-glutamatergic. For example, in one exemplary embodiment, the secondary agent may be riluzole (Rilutek®). In another particular embodiments, the secondary agent may be an excitatory amino acid. For example in one exemplary embodiment, the secondary agent may be talampanel. In still other particular embodiments, the secondary agent may be a growth factor. For example, in one exemplary embodiment, the secondary agent may be IPLEX. In further particular embodiments, the secondary agent may be a caspase inhibitor.

In any of the embodiments described above, an effective amount of (R)-pramipexole and an effective amount of one or more of the secondary agents described above may be provided adjunctively in separate pharmaceutical compositions or in a single dose pharmaceutical composition in which the (R)-pramipexole and one or more secondary agent are combined. In such embodiments, each separate pharmaceutical composition or a single dose pharmaceutical composition may further include a pharmaceutically acceptable excipient or carrier.

The compound 2-amino-4,5,6,7-tetrahydro-6-(propylamino)benzothiazole is a synthetic aminobenzothiazole derivative, having two enantiomers. The (S) enantiomer is a potent agonist of the $D_2$ family of dopamine receptors, with particular affinity for the $D_3$ receptor subtype. As a dopamine agonist, (S)-pramipexole activates dopamine receptors, thus mimicking the effects of the neurotransmitter dopamine. The (S)-pramipexole stereoisomer is a potent agonist of dopamine, with only small daily doses required and indeed tolerated by patients. Both enantiomers are thought to confer neuroprotective effects by their ability to accumulate in the brain, the spinal cord and mitochondria, and independent of the dopamine agonist activity, presumably through inhibition of lipid peroxidation, normalization of mitochondrial function and/or detoxification of oxygen radicals. As such, these compounds may have utility as inhibitors of the cell death cascades and loss of cell viability observed in neurodegenerative diseases.

The degree to which dosing of a molecule has demonstrable phenotypic activity resulting from affinity to particular receptors or other pharmaco-effective proteins, even when the activity results from affinities to unknown targets, can be operationally defined in terms of whether this activity contributes in a positive way ('on-target' activity) or a negative way ('off-target' activity) to a specific and desired therapeutic effect. For any given molecule, a number of 'off-target' activities can theoretically be identified, but 'on-target' activity is restricted to the desired therapeutic effect. To the extent that these activities can be measured and quantified, or comparisons be made with known standards, an index of activity can be generated for each of these categories (the 'activity equivalent', or AE), and one or more ratios generated to compare 'off-target' to 'on-target' activities, useful to compare potential risk-benefit ratios between molecules. Without wishing to be bound by theory, the 'off-target' activity for (R)-pramipexole in neurodegenerative disorders (other than Parkinson's disease) would be the 'on-target' activity for its enantiomer (S)-pramipexole, used to treat PD and restless legs syndrome.

In the case of (R)-pramipexole, two activities can be defined in this context. The first, which is agonist activity at a subset of human dopamine receptors and the resulting behavioral/toxicological phenotype, is 'off-target' activity for most neurodegenerative disorders. This activity results in dose-limiting side effects due to dopamine receptor agonist activity, and for the purposes of the current discussion can be defined to be the dopamine activity equivalent, or DAE. Throughout this application, the term "dopaminergic activity equivalent" (DAE) will mean the measure of activity at the dopamine receptors equivalent to the activity of 1 mg of (S)-pramipexole at the dopamine receptors. For example, a dosage of (R)-pramipexole having a DAE of 0.01 would have activity at the dopamine receptors which is equivalent to the activity of 0.01 mg of (S)-pramipexole. The DAE can also be related to a variety of pharmaceutical terms, including maximum tolerated dose (MTD), no observable adverse effect level (NOAEL), and non-effective dose amount. For example, the NOAEL dose amount for (S)-pramipexole is most preferably below 0.05 mg. This, in turn, corresponds to a DAE of below 0.05. A dose amount of (R)-pramipexole having a DAE of 0.01 would, therefore, be below the DAE for the most preferable (S)-pramipexole NOAEL dose amount of 0.05 mg. In some embodiments, DAE is determined by measuring the binding affinity ($IC_{50}$) or activity ($EC_{50}$) at the $D_2$ and/or $D_3$ receptors relative to the same parameter for 1 mg of (S)-pramipexole. For example, in certain embodiments, DAE may be determined by a suitable in vitro assay such as an $IC_{50}$ binding affinity assay for the $D_2$ or $D_3$ receptor such as those described by Schneider, C. S.; Mierau, J., "Dopamine Autoreceptor Agonists: Resolution and Pharmacological Activity of 2,6-Diaminotetrahydrobenzothiazole and an Aminothiazole Analogue of Apomorphine," (1987) *J. Med. Chem.* 30:494-498; or Wong, S. K.-F.; Shrikhande, A. V., S. K.-F. Wong, "Activation of Extracellular Signal-Regulated Kinase by Dopamine D2 and D3 Receptors," (2003) Society for Neuroscience Abstracts.

Our studies suggest that the DAE for (R)-pramipexole is much lower than may have been previously appreciated. For example, our studies have shown that the binding affinity for (R)-pramipexole to the $D_2$ and $D_3$ dopamine receptors is about 290 and 649 times lower than (S)-pramipexole, respectively, when using high chiral purity (R)-pramipexole. By comparison, the literature reports that the binding affinity for the (R)-pramipexole to the $D_2$ dopamine receptor is about 9-21 times lower than (S)-pramipexole, while the binding affinity for the (R)-pramipexole to the $D_3$ dopamine receptor is about 50 times lower than (S)-pramipexole.

Even more striking, our studies in beagle dogs indicate that the MTD dose ratio of (R)-pramipexole to (S)-pramipexole is 10,000, while the NOAEL dose ratio of (R)-pramipexole to (S)-pramipexole is 20,000. As a biological assay, the MTD and NOAEL in dogs reveal in vivo tolerance heretofore entirely unpredictable. Because of limitations on standard and quantitative analysis, the in vivo MTD and NOAEL in dogs may actually suggest even the slightest impurity of 0.005% could, in fact be responsible for the dopamine agonist-related side effects. These comparative studies suggest that the DAE for (R)-pramipexole is much lower than may previously been appreciated.

The other activity of (R)-pramipexole and (S)-pramipexole is neuroprotection. Neuroprotection is a phenomenon independent of mechanism, and hence qualifies as a category of activity. The neuroprotective activity of (R)-pramipexole and (S)-pramipexole is measurable and approximately equivalent in both enantiomers. Moreover, the neuroprotective activity can be defined in relative terms as the neuroprotective activity equivalent (NAE). Neuroprotective activity equivalent (NAE) refers to the neuroprotective activity inherent in 1 mg of (S)-pramipexole. NAE can be determined, for example, by measuring the neuroprotective activity in a standard in vitro neuroprotective assay relative to the activity of 1 mg of (S)-pramipexole. In some embodiments, the neuroprotective activity is determined by measuring cell death in the presence of MPP+ and/or rotenone in dopaminergic and/or non-dopaminergic cells (as a non-limiting example, see the assay in M. Gu, Journal of Neurochemistry, 91:1075-1081 (2004)).

Unlike the DAE, NAE has been shown to be equal in both pramipexole enantiomers in a number of in vitro tests. However, a larger dose of a pramipexole enatiomer is required to elicit neuroprotective activity in vivo, and because dosages of (S)-pramipexole are limited by the dopaminergic activity of the (S) enantiomer, which can lead to adverse side effects at dosages above the "No Observable Adverse Effect Level" (NOAEL dose amount), DAE is seen as a unit measure of the potential for adverse effects when describing neuroprotection, while the NAE is seen as a unit measure of the potential for therapeutic benefit. A NOAEL dose as used herein refers to an amount of active compound or pharmaceutical agent that produces no statistically or biologically significant increases in the frequency or severity of adverse effects between an exposed population and its appropriate control; some effects may be produced at this level, but they are not considered as adverse, or as precursors to adverse effects.

In practical terms, embodiments of the invention including the administration of (R)-pramipexole provide for significantly greater NAE levels and greater NAE/DAE levels than previously believed possible by administration of (S)-pramipexole thereby maximizing the probability that a therapeutically effective amount of (R)-pramipexole can be administered to a patient to provide neuroprotection. The NAE and the DAE may be useful in terms of a ratio, particularly as a ratio of beneficial to adverse effects, and useful to define a range over which a particular composition may be administered. (S)-pramipexole has a high DAE/NAE ratio, due to the high dopamine affinity, while the corresponding ratio for (R)-pramipexole is significantly lower.

With respect to (S)-pramipexole, exemplary adverse events are dizziness, hallucination, nausea, hypotension, somnolence, constipation, headache, tremor, back pain, postural hypotension, hypertonia, depression, abdominal pain, anxiety, dyspepsia, flatulence, diarrhea, rash, ataxia, dry mouth, extrapyramidal syndrome, leg cramps, twitching, pharyngitis, sinusitis, sweating, rhinitis, urinary tract infection, vasodilatation, flu syndrome, increased saliva, tooth disease, dyspnea, increased cough, gait abnormalities, urinary frequency, vomiting, allergic reaction, hypertension, pruritis, hypokinesia, nervousness, dream abnormalities, chest pain, neck pain, paresthesia, tachycardia, vertigo, voice alteration, conjunctivitis, paralysis, tinnitus, lacrimation, mydriasis and diplopia. For example, a dose of 1.5 mg of (S)-pramipexole has been shown to cause somnolence in human subjects (Public Statement on Mirapex®, Sudden Onset of Sleep from the European Agency for the Evaluation of Medicinal Products; Boehringer Ingelheim product insert for Mirapex® which indicates that the drug is administered as three doses per day). Further, studies performed in dogs, as presented herein, (see Examples and results shown in Table 11) indicate that the NOAEL dose may be as low as 0.00125 mg/kg, which is equivalent to a human dose of 0.0007 mg/kg or 0.05 mg for a 70 kg individual. Thus, with reference to (S)-pramipexole, a NOAEL dose amount may be an amount below 1.5 mg, below 0.50 mg, or more preferably below 0.05 mg. With reference to DAE as defined herein, a NOAEL dose may have a DAE of below 1.5, below 0.5, or more preferably below 0.05.

Generally, an amount larger than the non-effective dose amount of (S)-pramipexole is necessary to have a therapeutic effect in treating diseases alleviated by dopamine agonist activity. This amount, however, may not be desired when a neuroprotective effect is sought, as it may lead to the described adverse side effects. A "non-effective dose amount" as used herein refers to an amount of active compound or pharmaceutical agent that elicits a biological or medicinal response similar to the biological or medicinal response of a placebo as observed in a tissue, system, animal, individual or human that is being treated by a researcher, veterinarian, medical doctor or other clinician. A "non-effective dose amount" may therefore elicit no discernable difference from placebo in positive effects as observed in a tissue, system, animal, individual or human that is being treated by a researcher, veterinarian, medical doctor or other clinician. As such, the "non-effective dose amount" is not expected to (1) prevent a disease; for example, preventing a disease, condition or disorder in an individual that may be predisposed to the disease, condition or disorder but does not yet experience or display the pathology or symptomatology of the disease; (2) inhibit the disease; for example, inhibiting a disease, condition or disorder in an individual that is experiencing or displaying the pathology or symptomatology of the disease, condition or disorder (i.e., arresting or slowing further development of the pathology and/or symptomatology), or (3) ameliorate the disease; for example, ameliorating a disease, condition or disorder in an individual that is experiencing or displaying the pathology or symptomatology of the disease, condition or disorder (i.e., reversing or reducing the pathology and/or symptomatology).

As an example, in monkeys treated with MPTP (1-methyl-4-phenyl-1,2,3,6-tetrahydropyridine), a known dopaminergic neurotoxin, (S)-pramipexole has been shown to antagonize motor deficits and Parkinson-like symptoms in a dose-dependent manner, with the lowest effective oral dose being 0.053 mg/kg (see *Scientific Discussion* at http://www.emea.europa.eu/humandocs/PDFs/EPAR/Sifrol/059197EN6.pdf). This would be equivalent to a human dose of 0.017 mg/kg, or 1.2 mg for a 70 kg individual. In human trials, the lowest effective oral dose of (S)-pramipexole with a significant effect versus placebo in the treatment of Parkinson's disease was found to be 1.1 mg/day. Individual patients may need doses higher than 1.1 mg/day to gain a sufficient effect above the placebo effect (*Initial Scientific Discussion for the Approval of Mirapex* from the European Agency for the Evaluation of Medicinal Products). In human trials, the lowest effective dose with a significant effect versus placebo in the treatment of restless legs syndrome was found to be 0.25 mg/day (Boehringer Ingelheim product insert for Mirapex®). Therefore, with reference to (S)-pramipexole, a non-effective dose amount may be an amount below 1.0 mg/day, below 0.75 mg/day, below 0.5 mg/day, below 0.25 mg/day, or preferably below 0.125 mg/day. With reference to DAE, a non-effective dose amount per day may have a DAE per day below 1.0, below 0.75, below 0.5, below 0.25, or preferably below 0.125.

Other limits on the amount of (S)-pramipexole which can be administered to a patient also include the maximum recommended therapeutic dose and the maximum tolerated dose. A "maximum recommended therapeutic dose" (MRTD) refers to the dosages compiled by the FDA's Center for Drug Evaluation and Research, Office of Pharmaceutical Science, Informatics and Computational Safety Analysis Staff's Maximum Recommended Therapeutic Dose and as described in Matthews, et al., "Assessment of the Health Effects of Chemicals in Humans: I. QSAR Estimation of the Maximum Recommended Therapeutic Dose (MRTD) and No Effect Level (NOEL) of Organic Chemicals Based on Clinical Trial Data,", *Current Drug Discovery Technologies*, 2004, 1:61-76). The FDA's MRTD database cites a MRTD for S-pramipexole of 0.1 mg/kg/day or 7.0 mg/day for a 70 lb. person. Matthews, in turn, estimates that a NOEL (no adverse effect level) usually is about one-tenth of the MRTD, which corresponds to 0.01 mg/kg or about 0.7 mg/day for a 70 lb. person.

Because of its adverse impact on naïve patients, (S)-pramipexole must be titrated over the course of weeks to reach these dosages without dose limiting adverse effects (such as that documented in Boehringer Ingelheim product insert for Mirapex®). For example, for restless leg syndrome, the recommended starting daily dose amount of Mirapex® is 0.125 mg taken once daily 2-3 hours before bedtime. For patients requiring additional symptomatic relief, the daily dose may be increased to 0.25 mg over 4 to 7 day period and then to 0.5 mg over a second 4 to 7 day period. For the treatment of Parkinson's disease, the package insert recommends the following titration schedule for Mirapex®:

| Week | Dosage (mg) | Total daily dose (mg) |
|------|-------------|----------------------|
| 1 | 0.125 tid | 0.375 |
| 2 | 0.25 tid | 0.75 |
| 3 | 0.5 tid | 1.5 |
| 4 | 0.75 tid | 2.25 |
| 5 | 1.0 tid | 3.0 |
| 6 | 1.25 tid | 3.75 |
| 7 | 1.5 tid | 4.5 |

A "maximum tolerated dose" (MTD) as used herein refers to an amount of active compound or pharmaceutical agent which elicits significant toxicity in a tissue, system, animal, individual or human that is being treated by a researcher, veterinarian, medical doctor or other clinician. Single dose toxicity of (S)-pramipexole after oral administration has been studied in rodents, dogs, monkeys and human. In rodents, deaths occurred at doses of 70-105 mg/kg and above (*Initial Scientific Discussion for the Approval of Mirapex* from the European Agency for the Evaluation of Medicinal Products). This is equivalent to a human dose of 7-12 mg/kg, or approximately 500-850 mg for a 70 kg individual. In human subjects, a starting daily dose of (S)-pramipexole of greater than 0.20 mg was not tolerated when administered to a naïve patient. In dogs, vomiting occurred at 0.0007 mg/kg and above while monkeys displayed major excitation at 3.5 mg/kg. Further, the product insert for Mirapex® sets the maximally tolerated dose for humans at 4.5 mg/day, administered as three 1.5 mg single dosages. However, the 4.5 mg/day dosage is not administered to a naïve patient, but, instead, reached after a titration regimen (such as that documented in the product insert for Mirapex®). Generally, the starting daily dosage for administration to a naïve patient is a 0.125 mg dose administered three times per day and a seven-week titration schedule is recommended to reach a 1.5 mg dose administered three times daily. All species showed signs of toxicity related to exaggerated pharmacodynamic responses to (S)-pramipexole. For example, behavioral changes including hyperactivity were common and led to a number of secondary effects, such as reduced body weight and other stress-induced symptoms. In minipigs and monkeys, (S)-pramipexole moderately affected cardiovascular parameters. In rats, the potent prolactin-inhibitory effect of pramipexole affected reproductive organs (e.g. enlarged corpora lutea, pyometra), and showed a dose-related retinal degeneration during long-term exposure (*Initial Scientific Discussion for the Approval of Mirapex* from the European Agency for the Evaluation of Medicinal Products). Studies in dogs indicate a MTD amount of (S)-pramipexole for a human subject may be an amount below 4.5 mg/day, preferably below 1.5 mg/day. Further, the MTD amount for a human subject may be an amount below 0.3 mg/dose based on results of studies disclosed herein, and preferably below 0.2 mg/dose (see Table 11). With reference to DAE, the MTD amount may have a DAE of below 1.5, below 0.3, or below 0.2.

Given the limits on the amount of (S)-pramipexole that can be administered to a patient, the use of the embodiments of the present invention presents a clinically important alternative for the development of new neuroprotective therapies. The literature previously reported that the binding affinity of (R)-pramipexole at the $D_2$ receptor was approximately 9 to 21 times less than about that of (S)-pramipexole, while the binding affinity of (R)-pramipexole at the $D_3$ receptor was approximately 50 times less than about that of (S)-pramipexole (Table 10). These literature derived comparative binding affinity ratios suggest that (R)-pramipexole can be administered only at somewhat higher dosages than (S)-pramipexole. This limitation may occur because the exquisite sensitivity of tissues, systems, animals, and human subjects to the effects of dopamine agonism would preclude the use of (R)-pramipexole at doses that exceed tolerated doses of (S)-pramipexole by a factor greater than the literature derived comparative binding affinity ratios of the two enantiomers.

The seeming preclusion of higher doses of (R)-pramipexole can be demonstrated by reference to a theoretical 50 mg tablet. Assuming a 9 times difference in binding affinities, a 50 mg tablet which is 99.95% pure would have approximately 5.575 DAE (5.55 DAE from the (R)-pramipexole and 0.025 DAE from the (S)-pramipexole). Similarly, a 25 mg tablet would be expected to exhibit a DAE of 2.79 (2.78 from the (R)-pramipexole and 0.0125 DAE from the (S)-pramipexole). The MTD of (S)-pramipexole after a seven week titration regimen is 4.5 mg, or 1.5 mg three times a day, which is equivalent to a 4.5 DAE in a day or 1.5 DAE in a single dose. Further, the NOAEL dose amount for (S)-pramipexole is below 1.5 mg, preferably below 0.50 mg, or more preferably below 0.05 mg, which are each equivalent to 1.5 DAE, 0.5 DAE, and 0.05 DAE, respectively. Given that the single dose MTD for (S)-pramipexole has 1.5 DAE and the NOAEL of (S)-pramipexole has less than about 1.5 DAE, a single dosage of 50 mg with a DAE of 5.55 and a single dosage of 25 mg with a DAE of 2.79 would be precluded when referring solely to the literature derived comparative binding affinity ratios. Further, use of a high chiral purity of 99.95% as used in these theoretical dosages, would result in unacceptably high DAEs of 5.55 and 2.79 beyond the single dosage MTD DAE of 1.5 mg, and far beyond the preferable NOAELs of 0.5 DAE and 0.05 DAE.

To the contrary, in some embodiments, an aspect of the present invention involves unexpectedly high chiral purities that have been attained. These purities have led to MTDs or NOAELs for (R)-pramipexole which are higher than previously appreciated based on the literature derived comparative binding affinities. In some embodiments, pharmaceutical compositions, starting doses, method of treatment, and kits including (R)-pramipexole of high chiral purity are provided. Pursuant the discussion above, a 25 mg dosage with a similar chiral purity of 99.95% would be predicted to be well above the MTD or NOAEL for (S)-pramipexole and, therefore, result in observable adverse side effects. Studies in dogs, however, suggest that the high chiral purity (R)-pramipexole results in NOAEL dose amounts unexpectedly than those that may have been appreciated (Table 1). For example, a 25 mg/kg dosage of (R)-pramipexole with no detectable amount of (S)-pramipexole (0.05% limit of detection) resulted in no observable effects in dogs, which is unexpected based on the literature binding affinity data.

Further, studies in dogs demonstrate a high (approaching absolute) chiral purity of the pramipexole compositions for the (R)-enantiomer. (R)-pramipexole is administered in high dose levels in the studies disclosed herein (equivalent to human doses of 1,000 mg to 3,000 mg; see Examples), so that even the smallest amount of (S)-pramipexole would contribute to the observed NOAEL and MTD. For example, with reference to human equivalence doses based on data obtained in dogs, the MTD for the (R)-enantiomer has been shown to be equivalent to about 3,000 mg for a 70 kg human subject, while the equivalent MTD for the (S)-enantiomer would be equivalent to only 0.30 mg for that same subject (Table 1A). That is a difference of 10,000-fold. The NOAEL dose for the (R)-enantiomer is 20,000-fold greater than for the (S)-enantiomer (Table 1A). Thus, the (R)-pramipexole compositions used in these studies must be at least 99.99% pure if one were to assume that the observed side effects stemmed only from contamination by the (S)-enantiomer. On the other hand, these data demonstrate the high dose levels of the (R)-enantiomer of pramipexole that may be administered safely. This data highlights the usefulness of the high chiral purity for the (R)-enantiomer of pramipexole in various embodiments of the present invention.

Various embodiments of the invention are therefore directed to multi-component systems, pharmaceutical compositions and methods including (R)-pramipexole in higher dosages and higher chiral purities than could be achieved using (S)-pramipexole without eliciting adverse effects. Based on the chiral purity and the in vitro comparative binding affinity ratios, clinical NOAEL dose ratios, or clinical MTD dose ratios (herein "comparative ratios"), it may be possible to predict the DAE for a given dosage of (R)-pramipexole. Table 1 shows the DAE for a 25 mg dose of (R)-pramipexole as a function of comparative ratio and chiral purity. These data show that a much lower DAE can unexpectedly result from a 25 mg dosage form of (R)-pramipexole than may have been previously appreciated, due to the lower comparative ratios described herein when compared to the literature derived comparative ratios.

TABLE 1

DAE for a 25 mg dose of (R)-pramipexole as a function of % chiral purity and the comparative ratio

| Percent Chiral Purity for R PPX | 20,000 comparative ratio | 10,000 comparative ratio | 5,000 comparative ratio | 2,400 comparative ratio | 100 comparative ratio | 10 comparative ratio |
|---|---|---|---|---|---|---|
| 99.9967 | 0.0020749 | 0.0033249 | 0.0058248 | 0.0112413 | 0.2508168 | 2.5007425 |
| 99.9958 | 0.0022999 | 0.0035498 | 0.0060498 | 0.0114662 | 0.2510395 | 2.5009450 |
| 99.9950 | 0.0024999 | 0.0037499 | 0.0062498 | 0.0116661 | 0.2512375 | 2.5011250 |
| 99.9933 | 0.0029249 | 0.0041783 | 0.0066747 | 0.0120909 | 0.2516583 | 2.5015075 |
| 99.9900 | 0.0037499 | 0.0049998 | 0.0074995 | 0.0129156 | 0.2524750 | 2.5022500 |
| 99.9833 | 0.0054248 | 0.0066746 | 0.0091742 | 0.0145899 | 0.2531333 | 2.5037575 |
| 99.9800 | 0.0062498 | 0.0074995 | 0.0099990 | 0.0154158 | 0.2549500 | 2.5045000 |
| 99.9750 | 0.0074997 | 0.0087494 | 0.0112488 | 0.0166641 | 0.2561875 | 2.5056250 |
| 99.9667 | 0.0095746 | 0.0108242 | 0.0133233 | 0.0187382 | 0.2582418 | 2.5074925 |
| 99.9583 | 0.0116745 | 0.0129239 | 0.0154229 | 0.0208373 | 0.2603208 | 2.5093825 |
| 99.9500 | 0.0137494 | 0.0149988 | 0.0174975 | 0.0229115 | 0.2623750 | 2.5112500 |
| 99.9333 | 0.0179242 | 0.0191733 | 0.0216717 | 0.0270847 | 0.2665083 | 2.5150075 |
| 99.9000 | 0.0262488 | 0.0274975 | 0.0299950 | 0.0354063 | 0.2747500 | 2.5225000 |

TABLE 1-continued

DAE for a 25 mg dose of (R)-pramipexole as a function
of % chiral purity and the comparative ratio

| Percent Chiral Purity for R PPX | 20,000 comparative ratio | 10,000 comparative ratio | 5,000 comparative ratio | 2,400 comparative ratio | 100 comparative ratio | 10 comparative ratio |
|---|---|---|---|---|---|---|
| 99.8333 | 0.0429229 | 0.0441798 | 0.0466666 | 0.0520743 | 0.2912583 | 2.5375075 |
| 99.8000 | 0.0512475 | 0.0524950 | 0.0549900 | 0.0603958 | 0.2995000 | 2.5450000 |
| 99.7500 | 0.0637469 | 0.0649938 | 0.0674875 | 0.0728906 | 0.3118750 | 2.5562500 |
| 99.6667 | 0.0845708 | 0.0858167 | 0.0883093 | 0.0937065 | 0.3324918 | 2.5749925 |
| 99.5800 | 0.1062448 | 0.1074895 | 0.1099790 | 0.1153729 | 0.3539500 | 2.5945000 |
| 99.5000 | 0.1262438 | 0.1274875 | 0.1299750 | 0.1353656 | 0.3737500 | 2.6125000 |
| 99.3333 | 0.1679167 | 0.1691583 | 0.1764167 | 0.1770222 | 0.4150083 | 2.6500075 |
| 99.0000 | 0.2512375 | 0.2524750 | 0.2549500 | 0.2603125 | 0.4975000 | 2.7250000 |
| 98.3300 | 0.4187291 | 0.4199583 | 0.4224165 | 0.4277427 | 0.6633250 | 2.8757500 |
| 98.0000 | 0.5102250 | 0.5024500 | 0.5049000 | 0.5102083 | 0.7450000 | 2.9500000 |
| 97.5000 | 0.62621875 | 0.6274375 | 0.629875 | 0.6351563 | 0.86875 | 3.0625 |

Table 1 attempts to illustrate the importance of both purity and affinity on even a 25 mg single oral dosage. Assumptions regarding dopaminergic activity of the (R)-pramipexole at the dopamine receptors would seemingly preclude even a high purity (even 100% pure) 25 mg (R)-pramipexole tablet. Based upon the disclosure of the present invention one can immediately envisage numerous tables to illustrate the point. Tables 1A and 1B below are intended to illustrate the importance of purity for a single oral dosage form of (R)-pramipexole by illustrating the impact of even the smallest contamination of the composition by (S)-pramipexole

TABLE 1A

"NOAEL" dosages of (R)-pramipexole
compositions (based on DAE <0.05)

|  | 50 mg | 100 mg | 150 mg | 200 mg | 250 mg | 500 mg |
|---|---|---|---|---|---|---|
| (R)-purity % | 99.9000 | 99.9500 | 99.9667 | 99.9750 | 99.9800 | 99.9900 |
| (S)-impurity % | 0.1000 | 0.0500 | 0.0333 | 0.0250 | 0.0200 | 0.0100 |
| (S)-impurity DAE | 0.05 | 0.05 | 0.05 | 0.05 | 0.05 | 0.05 |

TABLE 1B

"Non-effective" dosages of (R)-pramipexole
compositions (based on DAE <0.125)

|  | 50 mg | 100 mg | 150 mg | 200 mg | 250 mg | 500 mg |
|---|---|---|---|---|---|---|
| (R)-purity % | 99.7500 | 99.8750 | 99.9170 | 99.9380 | 99.9500 | 99.9750 |
| (S)-impurity % | 0.2500 | 0.1250 | 0.0830 | 0.0620 | 0.0500 | 0.0250 |
| (S)-impurity DAE | 0.125 | 0.125 | 0.125 | 0.125 | 0.125 | 0.125 |

Based on the comparative ratios for binding affinity, NOAEL and MTD values, it is then possible to predict the amount of (R)-pramipexole that could be administered. Table 2 shows DAE as a function of a dosage of (R)-pramipexole (left hand column) and the comparative ratio (top row). With reference to Table 2, a unit dose can be chosen which allows for an amount of (R)-pramipexole having DAE which is equal to the non-effective amount of (S)-pramipexole. Indeed, unless a dual DAE/NAE effect is desired, a DAE would be avoided or minimized in a pharmaceutical composition. Thus, any single dose greater than 25 milligrams would not be expected to avoid off-target activity and would be expressly avoided by one skilled in the art. This is not true if, as in present invention, the comparative ratios exceed 200. This is best illustrated by Table 2.

TABLE 2

DAE as a function of (R)-pramipexole and comparative ratio (assuming 100% chiral purity of (R)-pramipexole)

|  | 20,000 | 10,000 | 5,000 | 2,400 | 1,700 | 1,300 | 650 | 400 | 300 | 200 | 100 | 50 |
|---|---|---|---|---|---|---|---|---|---|---|---|---|
| 2.5 | 0.00013 | 0.00025 | 0.0005 | 0.0010 | 0.0015 | 0.0019 | 0.0038 | 0.0063 | 0.0083 | 0.0125 | 0.0250 | 0.0500 |
| 5 | 0.00025 | 0.00050 | 0.001 | 0.0021 | 0.0029 | 0.0038 | 0.0077 | 0.0125 | 0.0167 | 0.0250 | 0.0500 | 0.1000 |
| 6.25 | 0.00031 | 0.00063 | 0.00125 | 0.0026 | 0.0037 | 0.0048 | 0.0096 | 0.0156 | 0.0208 | 0.0313 | 0.0625 | 0.1250 |
| 10 | 0.00050 | 0.00100 | 0.002 | 0.0042 | 0.0059 | 0.0077 | 0.0154 | 0.0250 | 0.0333 | 0.0500 | 0.1000 | 0.2000 |
| 12.5 | 0.00083 | 0.00125 | 0.0025 | 0.0052 | 0.0074 | 0.0096 | 0.0192 | 0.0313 | 0.0417 | 0.0625 | 0.1250 | 0.2500 |
| 15 | 0.00075 | 0.00150 | 0.003 | 0.0063 | 0.0088 | 0.0115 | 0.0231 | 0.0375 | 0.0500 | 0.0750 | 0.1500 | 0.3000 |
| 20 | 0.00100 | 0.00200 | 0.004 | 0.0083 | 0.0118 | 0.0154 | 0.0308 | 0.0500 | 0.0657 | 0.1000 | 0.2000 | 0.4000 |
| 25 | 0.00125 | 0.00250 | 0.005 | 0.0104 | 0.0147 | 0.0192 | 0.0385 | 0.0625 | 0.0833 | 0.1250 | 0.2500 | 0.5000 |
| 32.5 | 0.00163 | 0.00325 | 0.0065 | 0.0135 | 0.0191 | 0.0250 | 0.0500 | 0.0813 | 0.1083 | 0.1625 | 0.3250 | 0.6500 |
| 37.5 | 0.00188 | 0.00375 | 0.0075 | 0.0156 | 0.0221 | 0.0288 | 0.0577 | 0.0938 | 0.1250 | 0.1875 | 0.3750 | 0.7500 |
| 50 | 0.0025 | 0.0050 | 0.0100 | 0.0208 | 0.0294 | 0.0385 | 0.0769 | 0.1250 | 0.1667 | 0.2500 | 0.5000 | 1.0000 |
| 65 | 0.0033 | 0.0065 | 0.0130 | 0.0271 | 0.0382 | 0.0500 | 0.1000 | 0.1625 | 0.2167 | 0.3250 | 0.6500 | 1.3000 |
| 80 | 0.0040 | 0.0080 | 0.0160 | 0.0333 | 0.0471 | 0.0615 | 0.1231 | 0.2000 | 0.2667 | 0.4000 | 0.8000 | 1.6000 |
| 81.25 | 0.0041 | 0.0081 | 0.0163 | 0.0339 | 0.0478 | 0.0625 | 0.1250 | 0.2031 | 0.2708 | 0.4063 | 0.8125 | 1.6250 |
| 85 | 0.0043 | 0.0085 | 0.0170 | 0.0354 | 0.0500 | 0.0654 | 0.1308 | 0.213 | 0.283 | 0.425 | 0.850 | 1.700 |
| 100 | 0.0050 | 0.0100 | 0.0200 | 0.0417 | 0.0588 | 0.0769 | 0.1538 | 0.250 | 0.333 | 0.500 | 1.000 | 2.000 |
| 120 | 0.0060 | 0.0120 | 0.0240 | 0.0500 | 0.0706 | 0.0923 | 0.1846 | 0.300 | 0.400 | 0.600 | 1.200 | 2.400 |
| 130 | 0.0065 | 0.0130 | 0.0260 | 0.0542 | 0.0765 | 0.1000 | 0.2000 | 0.325 | 0.433 | 0.650 | 1.300 | 2.600 |
| 150 | 0.0075 | 0.0150 | 0.0300 | 0.0625 | 0.0882 | 0.1154 | 0.2308 | 0.375 | 0.500 | 0.750 | 1.500 | 3.000 |
| 162.5 | 0.0081 | 0.0163 | 0.0325 | 0.0677 | 0.0956 | 0.1250 | 0.2500 | 0.406 | 0.542 | 0.813 | 1.625 | 3.250 |
| 200 | 0.0100 | 0.0200 | 0.0400 | 0.0833 | 0.1176 | 0.1538 | 0.3077 | 0.500 | 0.667 | 1.000 | 2.000 | 4.000 |

TABLE 2-continued

DAE as a function of (R)-pramipexole and comparative ratio (assuming 100% chiral purity of (R)-pramipexole)

| | 20,000 | 10,000 | 5,000 | 2,400 | 1,700 | 1,300 | 650 | 400 | 300 | 200 | 100 | 50 |
|---|---|---|---|---|---|---|---|---|---|---|---|---|
| 212.5 | 0.011 | 0.021 | 0.043 | 0.0885 | 0.1250 | 0.1635 | 0.3269 | 0.531 | 0.708 | 1.063 | 2.125 | 4.250 |
| 250 | 0.013 | 0.025 | 0.050 | 0.1042 | 0.1471 | 0.1923 | 0.3846 | 0.625 | 0.833 | 1.250 | 2.500 | 5.000 |
| 260 | 0.013 | 0.026 | 0.052 | 0.1083 | 0.1529 | 0.2000 | 0.4000 | 0.650 | 0.867 | 1.300 | 2.600 | 5.200 |
| 300 | 0.015 | 0.030 | 0.060 | 0.1250 | 0.1765 | 0.2308 | 0.4615 | 0.750 | 1.000 | 1.500 | 3.000 | 6.000 |
| 325 | 0.016 | 0.033 | 0.065 | 0.135 | 0.191 | 0.250 | 0.500 | 0.813 | 1.083 | 1.625 | 3.250 | 6.500 |
| 340 | 0.017 | 0.034 | 0.068 | 0.142 | 0.200 | 0.262 | 0.523 | 0.850 | 1.133 | 1.700 | 3.400 | 6.800 |
| 350 | 0.018 | 0.035 | 0.070 | 0.146 | 0.206 | 0.269 | 0.538 | 0.875 | 1.167 | 1.750 | 3.500 | 7.000 |
| 400 | 0.020 | 0.040 | 0.080 | 0.167 | 0.235 | 0.308 | 0.615 | 1.000 | 1.333 | 2.000 | 4.000 | 8.000 |
| 500 | 0.025 | 0.050 | 0.100 | 0.208 | 0.294 | 0.385 | 0.769 | 1.3 | 1.7 | 2.5 | 5.0 | 10.0 |
| 600 | 0.030 | 0.060 | 0.120 | 0.250 | 0.353 | 0.462 | 0.923 | 1.5 | 2.0 | 3.0 | 6.0 | 12.0 |
| 625 | 0.031 | 0.063 | 0.125 | 0.260 | 0.368 | 0.481 | 0.962 | 1.6 | 2.1 | 3.1 | 6.3 | 12.5 |
| 650 | 0.033 | 0.065 | 0.130 | 0.271 | 0.382 | 0.500 | 1.000 | 1.6 | 2.2 | 3.3 | 6.5 | 13.0 |
| 850 | 0.043 | 0.085 | 0.170 | 0.354 | 0.500 | 0.654 | 1.308 | 2.1 | 2.8 | 4.3 | 8.5 | 17.0 |
| 1000 | 0.050 | 0.100 | 0.200 | 0.417 | 0.588 | 0.769 | 1.538 | 2.5 | 3.3 | 5.0 | 10.0 | 20.0 |
| 1200 | 0.060 | 0.120 | 0.240 | 0.500 | 0.706 | 0.923 | 1.846 | 3.0 | 4.0 | 6.0 | 12.0 | 24.0 |
| 1250 | 0.083 | 0.125 | 0.250 | 0.521 | 0.735 | 0.962 | 1.923 | 3.1 | 4.2 | 6.3 | 12.5 | 25.0 |
| 1300 | 0.065 | 0.130 | 0.260 | 0.542 | 0.765 | 1.000 | 2.000 | 3.3 | 4.3 | 6.5 | 13.0 | 26.0 |
| 1700 | 0.085 | 0.170 | 0.340 | 0.705 | 1.000 | 1.308 | 2.615 | 4.3 | 5.7 | 8.5 | 17.0 | 34.0 |
| 2000 | 0.100 | 0.200 | 0.400 | 0.833 | 1.176 | 1.538 | 3.077 | 5.0 | 6.7 | 10.0 | 20.0 | 40.0 |
| 2400 | 0.120 | 0.240 | 0.480 | 1.00 | 1.41 | 1.85 | 3.69 | 6.0 | 8.0 | 12.0 | 24.0 | 48.0 |
| 2500 | 0.125 | 0.250 | 0.500 | 1.04 | 1.47 | 1.92 | 3.85 | 6.3 | 8.3 | 12.5 | 25.0 | 50.0 |
| 3250 | 0.163 | 0.325 | 0.650 | 1.35 | 1.91 | 2.50 | 5.00 | 8.1 | 10.8 | 16.3 | 32.5 | 65.0 |
| 5000 | 0.250 | 0.500 | 1.000 | 2.08 | 2.94 | 3.85 | 7.69 | 12.5 | 16.7 | 25.0 | 50.0 | 100.0 |
| 6500 | 0.325 | 0.650 | 1.300 | 2.71 | 3.82 | 5.00 | 10.00 | 16.3 | 21.7 | 32.5 | 65.0 | 130.0 |
| 8500 | 0.425 | 0.850 | 1.700 | 3.54 | 5.00 | 6.54 | 13.08 | 21.3 | 28.3 | 42.5 | 85.0 | 170.0 |
| 10000 | 0.500 | 1.000 | 2.000 | 4.17 | 5.88 | 7.69 | 15.38 | 25.0 | 33.3 | 50.0 | 100.0 | 200.0 |
| 20000 | 1.000 | 2.000 | 4.000 | 8.33 | 11.76 | 15.38 | 30.77 | 50.0 | 66.7 | 100.0 | 200.0 | 400.0 |

A DAE equivalent to a preferred non-effective dose amount of the (S)-pramipexole may be below 1.0 mg; more preferably below 0.5 mg, and more preferably below 0.125 mg.

Similarly, one can ascertain the amount of (R)-pramipexole that could be administered which would be equivalent to a no observable adverse effect level dose amount of the (S)-pramipexole. Table 3 shows DAE as a function of a dosage of (R)-pramipexole (left hand column) and the comparative ratio (top row). With reference to Table 3, a unit dose can be chosen which allows for an amount of (R)-pramipexole having a DAE equal to the NOAEL dose amount of (S)-pramipexole. While 0.125 avoids unwanted effects, less than 0.05 avoids NOAEL. The difference in literature report and actual results is even more striking in Table 3.

TABLE 3

DAE as a function of dosages of (R)-pramipexole and comparative ratio (assuming 100% chiral purity of (R)-pramipexole)

| | 20,000 | 10,000 | 5,000 | 2,400 | 1,700 | 1,300 | 650 | 400 | 300 | 200 | 100 | 50.000 |
|---|---|---|---|---|---|---|---|---|---|---|---|---|
| 2.5 | 0.00013 | 0.00025 | 0.00050 | 0.00104 | 0.0015 | 0.0019 | 0.0038 | 0.0063 | 0.0083 | 0.0125 | 0.025 | 0.050 |
| 5 | 0.00025 | 0.00050 | 0.00100 | 0.00208 | 0.0029 | 0.0038 | 0.0077 | 0.0125 | 0.0167 | 0.0250 | 0.050 | 0.100 |
| 6.25 | 0.00031 | 0.00063 | 0.00125 | 0.00260 | 0.0037 | 0.0048 | 0.0096 | 0.0156 | 0.0208 | 0.0313 | 0.063 | 0.125 |
| 10 | 0.00050 | 0.00100 | 0.00200 | 0.00417 | 0.0059 | 0.0077 | 0.0154 | 0.0250 | 0.0333 | 0.0500 | 0.100 | 0.200 |
| 12.5 | 0.00063 | 0.00125 | 0.00250 | 0.00521 | 0.0074 | 0.0096 | 0.0192 | 0.0313 | 0.0417 | 0.0625 | 0.125 | 0.250 |
| 15 | 0.00075 | 0.00150 | 0.00300 | 0.00625 | 0.0088 | 0.0115 | 0.0231 | 0.0375 | 0.0500 | 0.0750 | 0.150 | 0.300 |
| 20 | 0.00100 | 0.00200 | 0.00400 | 0.00833 | 0.0118 | 0.0154 | 0.0308 | 0.0500 | 0.0667 | 0.1000 | 0.200 | 0.400 |
| 25 | 0.00125 | 0.00250 | 0.00500 | 0.01042 | 0.0147 | 0.0192 | 0.0385 | 0.0625 | 0.0833 | 0.1250 | 0.250 | 0.500 |
| 32.5 | 0.00163 | 0.00325 | 0.00650 | 0.01354 | 0.0191 | 0.0250 | 0.0500 | 0.0813 | 0.1083 | 0.1625 | 0.325 | 0.650 |
| 37.5 | 0.00188 | 0.00375 | 0.00750 | 0.01563 | 0.0221 | 0.0288 | 0.0577 | 0.0938 | 0.1250 | 0.1875 | 0.375 | 0.750 |
| 50 | 0.0025 | 0.0050 | 0.0100 | 0.0208 | 0.0294 | 0.0385 | 0.0769 | 0.1250 | 0.1667 | 0.2500 | 0.500 | 1.000 |
| 65 | 0.0033 | 0.0065 | 0.0130 | 0.0271 | 0.0382 | 0.0500 | 0.1000 | 0.1625 | 0.2167 | 0.3250 | 0.650 | 1.300 |
| 80 | 0.0040 | 0.0080 | 0.0160 | 0.0333 | 0.0471 | 0.0615 | 0.1231 | 0.2000 | 0.2667 | 0.4000 | 0.800 | 1.600 |
| 81.25 | 0.0041 | 0.0081 | 0.0163 | 0.0339 | 0.0478 | 0.0625 | 0.1250 | 0.2031 | 0.2708 | 0.4063 | 0.813 | 1.625 |
| 85 | 0.0043 | 0.0085 | 0.0170 | 0.0354 | 0.0500 | 0.0654 | 0.1308 | 0.2125 | 0.2833 | 0.4250 | 0.850 | 1.700 |
| 100 | 0.0050 | 0.0100 | 0.0200 | 0.0417 | 0.0588 | 0.0769 | 0.1538 | 0.2500 | 0.3333 | 0.5000 | 1.000 | 2.000 |
| 120 | 0.0060 | 0.0120 | 0.0240 | 0.0500 | 0.0706 | 0.0923 | 0.1846 | 0.3000 | 0.4000 | 0.6000 | 1.200 | 2.400 |
| 130 | 0.0065 | 0.0130 | 0.0260 | 0.0542 | 0.0765 | 0.1000 | 0.2000 | 0.3250 | 0.4333 | 0.6500 | 1.300 | 2.600 |
| 150 | 0.0075 | 0.0150 | 0.0300 | 0.0625 | 0.0882 | 0.1154 | 0.2308 | 0.3750 | 0.5000 | 0.7500 | 1.500 | 3.000 |
| 162.5 | 0.0081 | 0.0163 | 0.0325 | 0.0677 | 0.0956 | 0.1250 | 0.2500 | 0.4063 | 0.5417 | 0.8125 | 1.625 | 3.250 |
| 200 | 0.0100 | 0.0200 | 0.0400 | 0.0833 | 0.1176 | 0.1538 | 0.3077 | 0.5000 | 0.6667 | 1.0000 | 2.000 | 4.000 |
| 212.5 | 0.0106 | 0.0213 | 0.0425 | 0.0885 | 0.1250 | 0.1635 | 0.3269 | 0.5313 | 0.7083 | 1.0625 | 2.125 | 4.250 |
| 250 | 0.0125 | 0.0250 | 0.0500 | 0.1042 | 0.1471 | 0.1923 | 0.3846 | 0.6250 | 0.8333 | 1.2500 | 2.500 | 5.000 |
| 260 | 0.0130 | 0.0260 | 0.0520 | 0.1083 | 0.1529 | 0.2000 | 0.4000 | 0.6500 | 0.8667 | 1.3000 | 2.600 | 5.200 |
| 300 | 0.0150 | 0.0300 | 0.0600 | 0.1250 | 0.1765 | 0.2308 | 0.4615 | 0.7500 | 1.0000 | 1.5000 | 3.000 | 6.000 |
| 400 | 0.0200 | 0.0400 | 0.0800 | 0.1667 | 0.2353 | 0.3077 | 0.6154 | 1.0000 | 1.3333 | 2.0000 | 4.000 | 8.000 |
| 500 | 0.0250 | 0.0500 | 0.1000 | 0.2083 | 0.2941 | 0.3846 | 0.7692 | 1.2500 | 1.6667 | 2.5000 | 5.000 | 10.000 |
| 600 | 0.0300 | 0.0600 | 0.1200 | 0.2500 | 0.3529 | 0.4615 | 0.9231 | 1.5000 | 2.0000 | 3.0000 | 6.000 | 12.000 |
| 625 | 0.0313 | 0.0625 | 0.1250 | 0.2604 | 0.3676 | 0.4808 | 0.9615 | 1.5625 | 2.0833 | 3.1250 | 6.250 | 12.500 |
| 650 | 0.0325 | 0.0650 | 0.1300 | 0.2708 | 0.3824 | 0.5000 | 1.0 | 1.6 | 2.2 | 3.3 | 6.5 | 13.0 |

TABLE 3-continued

DAE as a function of dosages of (R)-pramipexole and comparative ratio (assuming 100% chiral purity of (R)-pramipexole)

|  | 20,000 | 10,000 | 5,000 | 2,400 | 1,700 | 1,300 | 650 | 400 | 300 | 200 | 100 | 50.000 |
|---|---|---|---|---|---|---|---|---|---|---|---|---|
| 850 | 0.0425 | 0.0850 | 0.1700 | 0.3542 | 0.5000 | 0.6538 | 1.3 | 2.1 | 2.8 | 4.3 | 8.5 | 17.0 |
| 1000 | 0.0500 | 0.1000 | 0.2000 | 0.4167 | 0.5882 | 0.7692 | 1.5 | 2.5 | 3.3 | 5.0 | 10.0 | 20.0 |
| 1200 | 0.0600 | 0.1200 | 0.2400 | 0.5000 | 0.7059 | 0.9231 | 1.8 | 3.0 | 4.0 | 6.0 | 12.0 | 24.0 |
| 1250 | 0.0625 | 0.1250 | 0.2500 | 0.5208 | 0.7353 | 0.9615 | 1.9 | 3.1 | 4.2 | 6.3 | 12.5 | 25.0 |
| 2000 | 0.1000 | 0.2000 | 0.4000 | 0.8333 | s | 1.5385 | 3.1 | 5.0 | 6.7 | 10.0 | 20.0 | 40.0 |
| 2400 | 0.1200 | 0.2400 | 0.4800 | 1.0000 | 1.4118 | 1.8462 | 3.7 | 6.0 | 8.0 | 12.0 | 24.0 | 48.0 |
| 2500 | 0.1250 | 0.2500 | 0.5000 | 1.0417 | 1.4706 | 1.9231 | 3.8 | 6.3 | 8.3 | 12.5 | 25.0 | 50.0 |
| 3250 | 0.1625 | 0.3250 | 0.6500 | 1.3542 | 1.9118 | 2.5000 | 5.0 | 8.1 | 10.8 | 16.3 | 32.5 | 65.0 |
| 5000 | 0.2500 | 0.5000 | 1.00 | 2.08 | 2.94 | 3.85 | 7.7 | 12.5 | 16.7 | 25.0 | 50.0 | 100.0 |
| 6500 | 0.3250 | 0.6500 | 1.30 | 2.71 | 3.82 | 5.00 | 10.0 | 16.3 | 21.7 | 32.5 | 65.0 | 130.0 |
| 8500 | 0.4250 | 0.8500 | 1.70 | 3.54 | 5.00 | 6.54 | 13.1 | 21.3 | 28.3 | 42.5 | 85.0 | 170.0 |
| 10000 | 0.5000 | 1.0000 | 2.00 | 4.17 | 5.88 | 7.69 | 15.4 | 25.0 | 33.3 | 50.0 | 100.0 | 200.0 |
| 20000 | 1.0000 | 2.0000 | 4.00 | 8.33 | 11.76 | 15.38 | 30.8 | 50.0 | 66.7 | 100.0 | 200.0 | 400.0 |

A DAE equivalent to a preferred no observable adverse effect level (NOAEL) dose amount of the (S)-pramipexole may be below 0.5 mg, preferably below 0.05 mg.

Further, Table 4 shows DAE as a function of a dosage of (R)-pramipexole (left hand column) and the comparative ratio (top row). With reference to Table 4, a unit dose can be chosen which allows a dose amount of (R)-pramipexole having a particular DAE.

TABLE 4

DAE as a function of dosages of (R)-pramipexole and comparative ration (assuming 100% chiral purity of (R)-pramipexole)

|  | 20,000 | 10,000 | 5,000 | 2,400 | 1,700 | 1,300 | 650 | 400 | 300 | 200 | 100 | 50 |
|---|---|---|---|---|---|---|---|---|---|---|---|---|
| 2.5 | 0.00013 | 0.00025 | 0.00050 | 0.0010 | 0.0015 | 0.0019 | 0.0038 | 0.0063 | 0.0083 | 0.013 | 0.025 | 0.050 |
| 5 | 0.00025 | 0.00050 | 0.00100 | 0.0021 | 0.0029 | 0.0038 | 0.0077 | 0.0125 | 0.0167 | 0.025 | 0.050 | 0.100 |
| 6.25 | 0.00031 | 0.00063 | 0.00125 | 0.0026 | 0.0037 | 0.0048 | 0.0096 | 0.0156 | 0.0208 | 0.031 | 0.063 | 0.125 |
| 10 | 0.00050 | 0.00100 | 0.00200 | 0.0042 | 0.0059 | 0.0077 | 0.0154 | 0.0250 | 0.0333 | 0.050 | 0.100 | 0.200 |
| 12.5 | 0.00063 | 0.00125 | 0.00250 | 0.0052 | 0.0074 | 0.0096 | 0.0192 | 0.0313 | 0.0417 | 0.063 | 0.125 | 0.250 |
| 15 | 0.00075 | 0.00150 | 0.00300 | 0.0063 | 0.0088 | 0.0115 | 0.0231 | 0.0375 | 0.0500 | 0.075 | 0.150 | 0.300 |
| 20 | 0.00100 | 0.00200 | 0.00400 | 0.0083 | 0.0118 | 0.0154 | 0.0308 | 0.0500 | 0.0667 | 0.100 | 0.200 | 0.400 |
| 25 | 0.00125 | 0.00250 | 0.00500 | 0.0104 | 0.0147 | 0.0192 | 0.0365 | 0.0625 | 0.0833 | 0.125 | 0.250 | 0.500 |
| 40 | 0.00200 | 0.00400 | 0.00800 | 0.0167 | 0.0235 | 0.0308 | 0.0615 | 0.1000 | 0.1333 | 0.200 | 0.400 | 0.800 |
| 50 | 0.00250 | 0.00500 | 0.010 | 0.021 | 0.029 | 0.038 | 0.077 | 0.125 | 0.167 | 0.250 | 0.500 | 1.000 |
| 60 | 0.00300 | 0.00600 | 0.012 | 0.025 | 0.035 | 0.046 | 0.092 | 0.150 | 0.200 | 0.300 | 0.600 | 1.200 |
| 65 | 0.00325 | 0.00650 | 0.013 | 0.027 | 0.038 | 0.050 | 0.100 | 0.163 | 0.217 | 0.325 | 0.650 | 1.300 |
| 80 | 0.00400 | 0.00800 | 0.016 | 0.033 | 0.047 | 0.062 | 0.123 | 0.200 | 0.267 | 0.400 | 0.800 | 1.600 |
| 85 | 0.00425 | 0.00850 | 0.017 | 0.035 | 0.050 | 0.065 | 0.131 | 0.213 | 0.283 | 0.425 | 0.850 | 1.700 |
| 100 | 0.00500 | 0.010 | 0.020 | 0.042 | 0.059 | 0.077 | 0.154 | 0.250 | 0.333 | 0.500 | 1.000 | 2.000 |
| 130 | 0.00650 | 0.013 | 0.026 | 0.054 | 0.076 | 0.100 | 0.200 | 0.325 | 0.433 | 0.650 | 1.300 | 2.600 |
| 150 | 0.00750 | 0.015 | 0.030 | 0.063 | 0.088 | 0.115 | 0.231 | 0.375 | 0.500 | 0.750 | 1.500 | 3.000 |
| 162.5 | 0.00813 | 0.016 | 0.033 | 0.068 | 0.096 | 0.125 | 0.250 | 0.406 | 0.542 | 0.813 | 1.625 | 3.250 |
| 200 | 0.010 | 0.020 | 0.040 | 0.083 | 0.118 | 0.154 | 0.308 | 0.500 | 0.667 | 1.000 | 2.000 | 4.000 |
| 260 | 0.013 | 0.026 | 0.052 | 0.108 | 0.153 | 0.200 | 0.400 | 0.650 | 0.867 | 1.300 | 2.6 | 5.2 |
| 300 | 0.015 | 0.030 | 0.060 | 0.125 | 0.176 | 0.231 | 0.462 | 0.750 | 1.000 | 1.500 | 3.0 | 6.0 |
| 325 | 0.016 | 0.033 | 0.065 | 0.135 | 0.191 | 0.250 | 0.500 | 0.813 | 1.083 | 1.625 | 3.3 | 6.5 |
| 340 | 0.017 | 0.034 | 0.068 | 0.142 | 0.200 | 0.262 | 0.523 | 0.850 | 1.133 | 1.700 | 3.4 | 6.8 |
| 350 | 0.018 | 0.035 | 0.070 | 0.146 | 0.206 | 0.269 | 0.538 | 0.875 | 1.167 | 1.750 | 3.5 | 7.0 |
| 400 | 0.020 | 0.040 | 0.080 | 0.167 | 0.235 | 0.308 | 0.615 | 1.000 | 1.333 | 2.000 | 4.0 | 8.0 |
| 480 | 0.024 | 0.048 | 0.096 | 0.200 | 0.282 | 0.369 | 0.738 | 1.200 | 1.600 | 2.400 | 4.8 | 9.6 |
| 500 | 0.025 | 0.050 | 0.100 | 0.208 | 0.294 | 0.385 | 0.769 | 1.250 | 1.667 | 2.500 | 5.0 | 10.0 |
| 600 | 0.030 | 0.060 | 0.120 | 0.250 | 0.353 | 0.462 | 0.923 | 1.500 | 2.000 | 3.000 | 6.0 | 12.0 |
| 850 | 0.043 | 0.085 | 0.170 | 0.354 | 0.500 | 0.654 | 1.308 | 2.125 | 2.833 | 4.250 | 8.5 | 17.0 |
| 1000 | 0.050 | 0.100 | 0.200 | 0.417 | 0.588 | 0.769 | 1.538 | 2.500 | 3.3 | 5.0 | 10.0 | 20.0 |
| 1200 | 0.060 | 0.120 | 0.240 | 0.500 | 0.706 | 0.923 | 1.846 | 3.000 | 4.0 | 6.0 | 12.0 | 24.0 |
| 1250 | 0.063 | 0.125 | 0.250 | 0.521 | 0.735 | 0.962 | 1.923 | 3.125 | 4.2 | 6.3 | 12.5 | 25.0 |
| 1300 | 0.065 | 0.130 | 0.260 | 0.542 | 0.765 | 1.000 | 2.000 | 3.250 | 4.3 | 6.5 | 13.0 | 26.0 |
| 1500 | 0.075 | 0.150 | 0.300 | 0.625 | 0.882 | 1.154 | 2.308 | 3.750 | 5.0 | 7.5 | 15.0 | 30.0 |
| 1700 | 0.085 | 0.170 | 0.340 | 0.708 | 1.000 | 1.308 | 2.615 | 4.250 | 5.7 | 8.5 | 17.0 | 34.0 |
| 2000 | 0.100 | 0.200 | 0.400 | 0.833 | 1.176 | 1.538 | 3.077 | 5.000 | 6.7 | 10.0 | 20.0 | 40.0 |
| 2400 | 0.120 | 0.240 | 0.480 | 1.000 | 1.412 | 1.846 | 3.692 | 6.000 | 8.0 | 12.0 | 24.0 | 48.0 |
| 2500 | 0.125 | 0.250 | 0.500 | 1.042 | 1.471 | 1.923 | 3.846 | 6.250 | 8.3 | 12.5 | 25.0 | 50.0 |
| 3250 | 0.163 | 0.325 | 0.650 | 1.354 | 1.912 | 2.500 | 5.000 | 8.125 | 10.8 | 16.3 | 32.5 | 65.0 |
| 4000 | 0.200 | 0.400 | 0.800 | 1.667 | 2.353 | 3.077 | 6.154 | 10.000 | 13.3 | 20.0 | 40.0 | 80.0 |
| 5000 | 0.250 | 0.500 | 1.000 | 2.083 | 2.941 | 3.846 | 7.7 | 12.5 | 16.7 | 25.0 | 50.0 | 100.0 |
| 6500 | 0.325 | 0.650 | 1.300 | 2.708 | 3.824 | 5.000 | 10.0 | 16.3 | 21.7 | 32.5 | 65.0 | 130.0 |
| 8500 | 0.425 | 0.850 | 1.700 | 3.542 | 5.000 | 6.538 | 13.1 | 21.3 | 28.3 | 42.5 | 85.0 | 170.0 |
| 10000 | 0.500 | 1.000 | 2.000 | 4.167 | 5.882 | 7.692 | 15.4 | 25.0 | 33.3 | 50.0 | 100.0 | 200.0 |
| 12000 | 0.600 | 1.200 | 2.400 | 5.000 | 7.059 | 9.231 | 18.5 | 30.0 | 40.0 | 60.0 | 120.0 | 240.0 |

TABLE 4-continued

DAE as a function of dosages of (R)-pramipexole and comparative ration (assuming 100% chiral purity of (R)-pramipexole)

|  | 20,000 | 10,000 | 5,000 | 2,400 | 1,700 | 1,300 | 650 | 400 | 300 | 200 | 100 | 50 |
|---|---|---|---|---|---|---|---|---|---|---|---|---|
| 20000 | 1.000 | 2.000 | 4.000 | 8.333 | 11.765 | 15.385 | 30.8 | 50.0 | 66.7 | 100.0 | 200.0 | 400.0 |
| 25000 | 1.250 | 2.500 | 5.000 | 10.417 | 14.706 | 19.231 | 38.5 | 62.5 | 83.3 | 125.0 | 250.0 | 500.0 |
| 35000 | 1.750 | 3.500 | 7.000 | 14.583 | 20.588 | 26.923 | 53.8 | 87.5 | 116.7 | 175.0 | 350.0 | 700.0 |
| 50000 | 2.500 | 5.000 | 10.000 | 20.833 | 29.412 | 38.462 | 76.9 | 125.0 | 166.7 | 250.0 | 500.0 | 1000.0 |
| 75000 | 3.750 | 7.500 | 15.000 | 31.250 | 44.118 | 57.692 | 115.4 | 187.5 | 250.0 | 375.0 | 750.0 | 1500.0 |
| 100000 | 5.000 | 10.000 | 20.000 | 41.667 | 58.824 | 76.923 | 153.8 | 250.0 | 333.3 | 500.0 | 1000.0 | 2000.0 |

DAE below 0.2, or below 5.

The higher comparative ratios described herein further suggest that a given dose of (R)-pramipexole can contain a certain amount of (S)-pramipexole impurity before exceeding the acceptable DAE. For example, Table 3 shows that a 25 mg dose of (R)-pramipexole results in 0.00125 DAE at a comparative ratio of 20,000 as suggested by the NOAEL ratio of (R)-pramipexole to (S)-pramipexole in the dog studies, assuming a 100% chiral purity of (R)-pramipexole. Theoretically, an additional 1.4 mg of (S)-pramipexole could be added without exceeding the DAE for a single dose MTD of (S)-pramipexole, while an additional 0.045 mg of (S)-pramipexole could be added before exceeding the preferable NOAEL dose amount of (S)-pramipexole. These compositions would be 96% pure and 99.8% pure. By contrast, a 25 mg of 100% pure (R)-pramipexole would result in 2.78 DAE, using the comparative binding affinity ratio of 9 from the literature, suggesting that even 100% purity would be insufficient to avoid adverse side effects. Hence, the present invention further provides particular doses of (R)-pramipexole which unexpectedly tolerate small amounts of (S)-pramipexole impurities.

Without wishing to be bound by theory, the neuroprotective effect of the compositions of the present invention may derive at least in part from the ability of the (R)-pramipexole to prevent neural cell death by at least one of three mechanisms: (1) the (R)-pramipexole may be reduce the formation of reactive oxygen species in cells with impaired mitochondrial energy production; (2) (R)-pramipexole may partially restore the reduced mitochondrial membrane potential that has been correlated with Alzheimer's disease, Parkinson's disease and amyotrophic lateral sclerosis diseases; and (3) (R)-pramipexole may block the cell death pathways which are produced by pharmacological models of Alzheimer's disease, Parkinson's disease, amyotrophic lateral sclerosis diseases and mitochondrial impairment.

Although any methods and materials similar or equivalent to those described herein can be used in the practice or testing of embodiments of the present invention, the preferred methods, devices, and materials are now described.

Pharmaceutical Compositions

Various embodiments of the invention include pharmaceutical compositions that include an effective amount of (R)-pramipexole and an effective amount of one or more secondary agents. In such embodiments, the effective amount of (R)-pramipexole and the effective amount of one or more secondary agents may be provided adjunctively in separate pharmaceutical compositions or in a single dose pharmaceutical composition. Each composition may further include a pharmaceutically acceptable excipient or carrier.

As such, certain embodiments of the invention provide a composition including (R)-pramipexole. The compositions of the invention may include (R)-pramipexole having a chiral purity at least greater that 96%. For example, the chiral purity may be at least 99.5%, at least 99.6%, at least 99.7%, at least 99.8%, at least 99.9%, least 99.95%, or preferably at least 99.99%. In some embodiments, the composition my have a chiral purity for (R)-pramipexole of 99.90% or greater, and in other embodiments, the composition has a chiral purity for (R)-pramipexole of 99.95% or greater. In still other embodiments, the composition has a chiral purity for (R)-pramipexole of 99.99% or greater, and in certain embodiments, the chiral purity for (R)-pramipexole is 100%.

The high chiral purity of the (R)-pramipexole used herein may allow for therapeutic compositions that have a wide individual and daily dose range. For example, in some embodiments, the amount of (R)-pramipexole may be from about 0.01 mg/kg/day to about 10,000 mg/kg/day, from about 1 mg/kg/day to about 1,000 mg/kg/day, from about 0.1 mg/kg/day to about 1,000 mg/kg/day, from about 1 mg/kg/day to about 1,000 mg/kg/day, from about 1,000 mg/kg/day to about 10,000 mg/kg/day, or from about 1 mg/kg/day to about 100 mg/kg/day. In other embodiments, the amount of (R)-pramipexole may be from about 3 mg/kg/day to about 70 mg/kg/day. In still other embodiments, amount of (R)-pramipexole may be from about 7 mg/kg/day to about 40 mg/kg/day. In yet other embodiments, the amount of (R)-pramipexole may be from about 3 mg/kg/day to about 50 mg/kg/day. In further embodiments, the dosage may be 10 mg/day to 1,500 mg/day, more preferably 100 mg/day to 600 mg/day. The amount of (R)-pramipexole in the compositions may preferably be about 25 mg to about 5,000 mg, about 50 mg to about 5,000 mg, from about 100 mg to about 3,000 mg, from about 300 mg to about 1,500 mg, from about 500 mg to about 1,000 mg. In yet further embodiments, the amount of (R)-pramipexole in the compositions may be about from about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 200 mg, to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the amount of (R)-pramipexole is from about 600 mg to about 900 mg. This dose may be administered as a single daily dose, or may be divided into several doses administered throughout the day, for example, 1 to 5 doses, preferably two or three doses per day. In some embodiments, the amount of (R)-pramipexole is from about 50 mg to about 5000 mg. In some embodiments, the amount of (R)-pramipexole is from about 100 mg to about 3000 mg. In some embodiments, the amount of (R)-pramipexole is from about 300 mg to about 1500 mg. In some embodiments, the amount of (R)-pramipexole is from about 500 mg to about 1000 mg. In some embodiments, the composition is suitable for oral administration. In some embodiments, the composition is a solid oral dosage form.

In some embodiments, one or more secondary therapeutic agents such as, for example, dopamine agonists, dopaminergic agonists, COMT inhibitors, MOA inhibitors, excitatory amino acid antagonists, growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and downregulators, monoamine oxidase type B (MOAB) inhibitors, multi-target agents, kinase inhibitors, Bcl inducers, histone deacetylase (HDAC) mediators, glial modulators, mitochondrial energy promoting agents, myostatin inhibitors, caspase inhibitors and combinations thereof may be adjunctively administered with (R)-pramipexole.

Exemplary dopamine agonists include, but are not limited to, apomorphine, carbidopa/levodopa, bromocriptine, lisuride, cabergoline and piribedel. Exemplary dopaminergic agonists include, but are not limited to, ropinirole, rotigotine, pergolide, amantadine. Exemplary COMT inhibitors include, but are not limited to entacapone and tolcapone. Exemplary MOA inhibitors include, but are not limited to, selegiline, rasagiline moclobemide, isocarboxazid, phenelzine, tranylcypromine, nialamide, iproniazid, iproclozide, toloxatone, linezolid, dextroamphetamine, EVT 302 (Evotec, Inc.), Ro 19-6491 (Hoffman-La Roche, Inc.), Ro 19-6327 (Hoffman-La Roche, Inc.), deprenyl, pargyline and ladostigil (TV-3326). Exemplary excitatory amino acid antagonists include, but are not limited to, talampanel.

In particular embodiments, one or more secondary agents that are dopamine agonists, such as, for example, D2/D3 agonists may be adjunctively administered with (R)-pramipexole. In such embodiments, the (R)-pramipexole exert neuroprotective effects while the D2/D3 agonists activate dopamine receptors. The invention is not limited to any particular dopamine agonist, and any dopamine agonist or combination of dopamine agonists known in the art may be used in combination with (R)-pramipexole in embodiments of the invention. For example, useful D2/D3 agonists may include, but are not limited to, pramipexole ((6S)-4,5,6,7-tetrahydro-N6-propyl-2,6-benzothiazole-diamine) (e.g., Mirapex®), ropinirole (e.g., Requip®), carbidopa, levodopa, entacapone (e.g., COMtan®), carbidopa/levodopa (e.g., Sinemet®), carbidopa/levodopa/entacapone (e.g. Stalevo®), selegiline (e.g., Eldpryyl®), rotigotine (e.g., Neupro®), rasagaline (e.g., Azilect®), apomorphine (e.g., Apokyn®), bromocriptine (e.g., Parlodel®), amantadine (e.g., Symmetrel®) paliroden, xaliproden, talampanel and combinations thereof. In such embodiments, the secondary agent may have a DAE that is substantially greater that (R)-pramipexole. Thus, the combination of (R)-pramipexole and one or more dopamine agonists may result in a multi-component system or a pharmaceutical composition that provides both a high NAE and a high DAE and elicits both good neuroprotective effects and improved dopamine activity.

For example, daily dosages of a dopamine agonist administered adjunctively with (R)-pramipexole may a therapeutically effective amount, for example, from about 2 mg to about 6 mg of apomorphine, up to about 1000 mg of levodopa, up to about 1000 mg of levodopa in combination with carbidopa, wherein the ratio of carbidopa/levodopa is 1:4 or 1:10, from about 2 mg to about 24 mg of ropinorole, from about 2 mg to about 6 mg of rotigotine, from about 0.05 mg to about 5 mg of pergolide, from about 100 to about 400 mg of amantadine, from about 200 mg to about 1600 mg of entacapone, from about 300 mg to about 600 mg of tolcapone, about 10 mg of selegiline, from about 0.5 mg to about 1 mg of rasagiline.

The dopamine agonists of embodiments may provided in any suitable dose that is therapeutically effective. For example, in some embodiments, (S)-pramipexole may be provided an amount that does not exceed about 1.0 mg. In others, the non-effective dose amount of (S)-pramipexole is an amount that does not exceed about 0.75 mg, about 0.5 mg, about 0.25 mg, or about 0.125 mg. In some embodiments, the non-effective dose amount of (S)-pramipexole is less than about 0.125 mg.

In various embodiments, an effective amount of one or more growth factors and/or neurotrophic factors such as, but are not limited to, insulin-like growth factor-1 (IGF-1), IGF-1 adenoviral-associated virus (IGF-1 AAV), mecasermin rinfabate (IPLEX), glial cell line-derived neurotrophic factor (GDNF), hepatocyte growth factor (HGF), granulocyte colony stimulating factor (G-CSF), or combination thereof may be adjunctively administered with (R)-pramipexole. For example, some embodiments include pharmaceutical compositions that include an effective amount of (R)-pramipexole and an effective amount of IGF-1. In such embodiments, the effective amount of (R)-pramipexole and the effective amount of IGF-1 may be provided adjunctively in separate pharmaceutical compositions or in a single dose pharmaceutical composition wherein each composition may further include a pharmaceutically acceptable excipient or carrier.

The IGF-1 system includes three structurally related ligands (IGF-1, IGF-2 and insulin), their respective receptors, and at least six IGF-1 binding proteins (IGFBP), and IGF-1 may exert multiple actions within the peripheral and central nervous systems. The majority of circulating IGF-1 is bound and sequestered by IGFBPs, thereby extending the half-life of IGF-1, regulating its distribution, and controlling its bioavailability in various tissues. IGF-1 functions are mediated via the IGF-1R, a hetero-tetramer having two extracellular α-subunits which contain the ligand binding site and two transmembrane β-subunits which have tyrosine kinase activity upon ligand binding and catalyze the auto-phosphorylation of tyrosine residues on the intracellular domain of the n-subunit. Auto-phosphorylation of the receptor causes recruitment of the adaptor molecules insulin receptor substrate 1 and 2 (IRS1 and IRS2). Upon phosphorylation, the IRS proteins activate signaling pathways including the PI3K/Akt and p44/42 MAPK pathways.

Additional pathways linked to IGF-1 signaling include the JNK, p38 MAPK, and mTOR signaling pathways. Signaling pathways activated by IGF-1 result in a wide range of cellular effects including cellular proliferation, differentiation and inhibition of apoptosis. The neuroprotective properties of IGF-1 have been addressed in many models of neuronal degeneration. For example, Sakowski et al., 1 Amyotrophic Lateral Sclerosis, 1-11 (2008) have shown a beneficial effects of IGF-1 in neuronal cell types including human neuroblastoma cells, dorsal root ganglion cells and motor neurons. Additionally, Studies in cell lines and animal models offer insight into the potential of IGF-1 as a treatment for ALS, and in vitro studies indicate that IGF-1 may have neuroprotective properties in ALS models. For example, in one such model system, primary embryonic rat spinal motor neurons, which express IGF-IR and respond to exogenous IGF-1 treatment. Studies using primary motor neuron cultures demonstrate that IGF-1 prevents glutamate-induced caspase-3 cleavage, DNA fragmentation and cell death. The window for the protective effects of IGF-1 in these studies was small following exposure to glutamate and implies that the effects of IGF-1 might impact early events in the activation of cell death. These studies suggest that activation of the PI3K/Akt and p44/42 MAPK signaling pathways may be instrumental in the protective effects of IGF-1, as determined utilizing pathway-specific small molecule inhibitors.

The signaling pathways implicated by these studies also correlate with axon outgrowth in postnatal corticospinal motor neurons (CSMN), which are subject to degeneration in ALS. These studies confirm that IGF-1 leads to activation of the PI3K/Akt and p44/42 MAPK signaling pathways in CSMN and indicate that blockade of these pathways results in defects in axonal outgrowth. Adenoviral-associated viral (AAV)-mediated expression of IGF-1 in SH-SY5Y neurons and primary motor neurons also causes significant protection against glutamate-induced toxicity. Neighboring neurons without AAV-IGF-1 expression were also protected against glutamate-induced toxicity, indicating that this delivery method produces biologically active IGF-1 which is released from transfected cells. Taken together, these data indicate that IGF-1 is protective to motor neurons, activates signaling pathways associated with cell survival, and promotes axonal outgrowth.

IPLEX is a hybrid protein complex of human insulin-like growth factor-1 (rhIGF-1) and human insulin-like growth factor-binding protein-3 (rhIGFBP-3) which is for the treatment of growth failure in children with severe primary IGF-1 deficiency and which may be provide therapy for neurodegenerative diseases such as ALS and muscular dystrophy. Glial cell line-derived neurotrophic factor (GDNF) is a small protein that potently promotes the survival and differentiation of dopaminergic and motor neurons. Hepatocyte growth factor (HGF) is a paracrine cellular growth, motility and morphogenic factor that is secreted by mesenchymal cells and targets and acts primarily upon epithelial and endothelial cells. HGF regulates cell growth, cell motility, and morphogenesis by activating a tyrosine kinase signaling cascade after binding to the proto-oncogene c-Met receptor and has a major role in embryonic organ development, in adult organ regeneration and in wound healing. Its ability to stimulate mitogenesis, cell motility, and matrix invasion may provide HGF with a central role in angiogenesis and tissue regeneration. Granulocyte-colony stimulating factor (G-CSF) is a neurotrophic factor that has been shown to protect cultured motoneurons from apoptosis that has been shown to increase survival of motoneurons and decreases muscular denervation atrophy in ALS mice. G-CSF is clinically well tolerated and crosses the intact blood-brain barrier.

In various embodiments, an effective amount of one or more antioxidants, anti-inflammatories, and immunomodulators such as, but are not limited to, AEOL 10150, cefriaxone, celastrol, coenzyme Q10, copaxone, cox-2 inhibitors (including nimesulide), cyclosporin, ebselen, edaravone (radicut), promethazine, tamoxifen, thalidomide, vitamin E, VP025, or combination thereof may be adjunctively administered with (R)-pramipexole. Without wishing to be bound by theory, substantial evidence suggests that both inflammation and oxidative damage contribute to the pathogenesis of motor neuron degeneration in ALS. Therefore, combining (R)-pramipexole with one or more antioxidants, anti-inflammatories, and immunomodulators may provide improved or synergistic neuroprotective activity over (R)-pramipexole alone.

AEOL-10150, a small-molecule antioxidant analogous to the catalytic site of superoxide dismutase, is a potential treatment for ALS, stroke, spinal cord injury, lung inflammation and mucositis that appears to be safe and well-tolerated in both a single and a multi-dose. Ceftriaxone is a beta-lactam antibiotic that acts to inhibit bacterial synthetic pathways that has been shown to be a potent stimulator of glutamate receptor (GLT1), a principal excitatory neurotransmitter in the nervous system whose activation is handled by the glutamate transporter (GLT1). Ceftriaxone increases expression of GLT1 in brain and up-regulates biochemical and functional activity of GLT-1 and appears to delay the loss of neurons and muscle strength and increase survival in the mouse model of ALS. Glutamine is important for normal excitatory synaptic transmission, while its dysfunction is implicated in acute and chronic neurological disorders, including ALS, stroke, brain tumors and epilepsy. Celastrol is a potent anti-inflammatory compound that significantly improves weight loss, motor performance and delays the onset of disease in the mouse model of ALS. Celastrol treatment. Coenzyme Q10 (CoQ10) is a mitochondrial cofactor and a powerful antioxidant that has been shown to naturally accumulate at low levels in number of conditions including Parkinson's disease, heart disease and cancer. It has recently been reported that CoQ10 may extend the survival in mouse models of several neurodegenerative disorders such as ALS.

The inflammatory process in ALS appears to involve infiltration of T cells and activation of antigen presenting cells co-localizing with motor neuron damage in the brain and spinal cord. T cells may damage motor neurons by cell-cell contact or cytokine secretion, or contribute indirectly to motor neuron damage through activation of microglia and macrophages. Alternatively, T cell infiltration may be an epiphenomenon related to clearance of dead motor neurons. Animal models of neuroinflammation and neurodegeneration indicate that T cell response can be neuroprotective or even enhance neurogenesis. Therefore, it is possible that T cells can be induced to slow motor neuron destruction and facilitate repair in ALS. Copaxone (glatiramer acetate) is an immunomodulator that appears to induce CD8 T cell response has shown promising results in treatment of ALS in animal models.

Cox-2 inhibitors, such as nimesulide, are a type of non-steroidal anti-inflammatory drug (NSAID) that directly target cox-2, an enzyme responsible for inflammation and pain that have been implicated as potential therapeutics for ALS treatment in experimental studies in animal models, cell culture models of ALS-type neurodegeneration, and studies of postmortem ALS brain. For example, prophylactic dietary supplementation with nimesulide resulted in a significant delay in the onset of motor impairment and reduced cox-2-mediated induction of pro-inflammatory prostaglandin in the cervical spinal cord toward normal levels which provides evidence for the therapeutic use of cox-2 inhibitors in ALS.

Cyclosporin is an inhibitor of the mitochondrial permeability pore and an anti-anti-inflammatory/immunosuppressant that has been shown increase survival in animal models of ALS. Ebselen has appears to affect multiple pathways including modulation of NMDA function via the NMDA redox site and inhibition of several kinases including p38MAPK and JNK that may prevent binding of certain transcription factors such as AP-1. Edaravone is a free-radical scavenger for treatment of cerebral ischemia that may slow symptom progression and motor neuron degeneration in the ALS model mice. Promethazine is a H1 receptor antagonist antihistamine and antiemetic that has been shown to delay the onset of ALS in mice. Tamoxifen is a selective estrogen receptor modulator used in the treatment of breast cancer. Recently, tamoxifen has been implicated as a protein kinase C inhibitor with anti-glutamate activity that may reduce the toxic effect of excess of glutamate on motor neurons in ALS. Thalidomide, a small molecule drug, inhibits TNF-alpha protein synthesis that can readily cross the blood-brain barrier that may reduce inflammation. TNF-alpha plays a major role in central nervous system neuroinflammation-mediated cell death, and thalidomide may reduce the neuroinflammation associated with TNF-alpha that is secreted by the brain-resident marcophages (the microglial cell) in response to various stimuli. VP025 inhibits neuro-inflammation and appear to slow the progression of ALS through interaction with immune cells leading to the modulation of cytokines. The antioxidant vitamin E (alpha-tocopherol) has been shown to slow down the onset and progression of the paralysis in transgenic mice expressing a mutation in the superoxide dismutase gene found in certain forms of familial ALS.

In some embodiments, effective amount of one or more anti-glutamatergics and ion channel blockers such as, but are not limited to, FP-0011, memantine, N-acetylated-a-linked acidic dipeptidease (NAALADase) inhibitors, nimodipine, riluzole or combination thereof may be adjunctively administered with (R)-pramipexole. Excessive glutamate levels have been shown to be toxic to neurons, and evidence suggests that both direct and indirect glutamate toxicity may contribute to the pathogenesis of motor neuron degeneration in diseases such as ALS.

FP0011 is an antiglutamatergic compound that may reduce presynaptic glutamate levels and shows strong neuroprotective properties. Memantine is a noncompetitive N-methyl-d-aspartate (NMDA) receptor antagonist that has been shown to protect neurons against NMDA or glutamate-induced toxicity in vitro and in animal models of neurodegenerative diseases. N-Acetylated-Alpha-Linked-Acidic-Dipeptidase (NAALADase) converts N-Acetyl-Aspartyl-Glutamate into glutamate during neuronal damage and may represent a new approach to block the release of excess glutamate without interfering with normal brain function in treatment of neurodegenerative disorders. Nimodipine is a dihydropyridine calcium channel blocker which may antagonize excitatory amino acid receptor activation decreasing calcium entry into damaged neurons and might help to slow or reverse ALS. Riluzole is an anti-convulsant and a neuroprotective agent that specifically blocks sodium channels in their inactivated states. Riluzole has been shown to significantly prolong survival in the bulbar-onset group of the overall population.

In other embodiments, an effective amount of one or more AMPA receptor antagonists such as, but are not limited to, 1,2,3,4-tetrahydro-6-nitro-2,3-dioxo-benzo[f]quinoxaline-7-sulfonamide (NBQX), talampanel, or combination thereof may be adjunctively administered with (R)-pramipexole. AMPA antagonists have shown clear beneficial effect in mouse models of ALS, including prolonged survival and maintained or improved motor function.

1,2,3,4-tetrahydro-6-nitro-2,3-dioxo-benzo[f]quinoxaline-7-sulfonamide (NBQX) is an AMPA receptor antagonist that may reduce excitotoxicity which has been implicated in the selective motor neuron loss in ALS. Talampanel is a selective AMPA receptor antagonist that prevents glutamate excitotoxicity which may trigger motor neuron death. Talampanel has been studied in a small group of human subjects with ALS, showing a positive trend in the ALS Functional Rating Scale as compared to those treated with placebo.

In still other embodiments, an effective amount of one or more heat shock protein inducers, protein disaggregators or protein downregulators such as, but are not limited to, arimoclomol, ISIS 333611, lithium, misfolded SOD-1 antibodies, rhHSP70, TDP-43 antagonists and trehalose or combinations thereof may be adjunctively administered with (R)-pramipexole.

Arimoclomol has been shown to protect motor nerves subjected to physical trauma and accelerate the regeneration of previously damaged nerves in animals by amplifying "molecular chaperone" proteins thereby enhancing a cell's natural ability to mend damaged, misfolded proteins. Thus, Arimoclomol may provide cellular protection from misfolded, toxic proteins that are believed to cause many neurodegenerative diseases and may have broad application profile in various neurodegenerative diseases including, for example, ALS. ISIS 333611 inhibits Cu/Zn superoxide dismutase (SOD1) a molecule associated with the familial form of ALS, and delivery of ISIS 333611 directly to the cerebral spinal fluid significantly decreases production of the mutant protein in neurons and surrounding cells and has been shown to prolong the lifetime of rats that show features of ALS. Lithium has been shown to possess neuroprotective properties in a variety of disease models such as brain ischemia and kainite toxicity and appears to have the ability to promote autophagy through the inhibition of inositol-monophosphatase 1. In disease models of ALS, lithium delays disease onset and augments life span through the activation of autophagy, increasing in the number of mitochondria in motor neurons and suppressing reactive astrogliosis.

Misfolding of SOD1 has emerged as mechanism underlying motor neuron degeneration in individuals with ALS who carry a mutant SOD1 gene. The SOD1 exposed dimer interface (SEDI) antibody recognizes only those SOD1 conformations in which the native dimer is disrupted or misfolded, and by binding specifically to the misfolded protein, SEDI has been shown to ameliorate mutant protein deposition in the cytoplasm and augment life span.

One of the most common cellular mechanisms to survive a stressful condition is the heat shock response, characterized by an increase in the transcription of a subset of genes resulting in the production of inducible heat shock proteins, and insufficient availability of HSP70 may contribute to motorneuron death in ALS mice. HSP70 expression has been shown to confer neuroprotection, and exogenous delivery of recombinant human HSP70 (rhHSP70) has been shown to increase life span, delay symptom onset, preserve motor function, and prolong motorneuron survival in mouse models of ALS.

Evidence suggests a pathophysiological link between ubiquitinated TAR DNA binding protein (TDP-43) and ALS, and TDP-43 inclusions have been shown to play a role in the pathogenesis of ALS. Therefore, TDP-43 antagonists may have a therapeutic effect on neurodegenerative diseases. Trehalose is a natural alpha-linked disaccharide formed by an α, α-1, 1-glucoside bond between two α-glucose units that may inhibit polyglutamine-induced protein aggregation in vitro and in vivo in Huntington's disease models.

In yet other embodiments, an effective amount of one or more MOAB inhibitor such as, but are not limited to, R(+)N-propargyl-1-aminoindan (rasagiline) may be adjunctively administered with (R)-pramipexole. Rasagiline is an irreversible inhibitor of MOAB that has been shown to have a significant dose-dependent therapeutic effect on both preclinical and clinical motor function and survival in neurodegenerative disorders.

In further embodiments, with an effective amount of one or more multi-target agents such as, but are not limited to, 4-[2(aminomethyl)-1,3-thiazol-4-yl]-2,6 di-tert-butylphenol (BN82451) may be adjunctively administered with (R)-pramipexole. BN82451 belongs to a family of small molecules designated as multi-targeting or hybrid molecules that is orally active, penetrates central nervous system, and elicits potent neuronal protection, due to Na+ channel blockade, antioxidant properties, and mitochondria-protecting activity, and anti-inflammatory properties due to inhibition of cyclooxygenases.

In still further embodiments, an effective amount of one or more kinase inhibitors such as, but are not limited to, olomoucine, quinolin-2(1H)-one derivatives, roscovitine, tamoxifen and combinations thereof may be adjunctively administered with (R)-pramipexole. Misfolding of SOD1 leads to protein aggregation which has been observed in animal models of ALS as well as in human sporadic and familial ALS patients and is one of the earliest measurable events in the mouse. The protein aggregates may also impair or alter the function of the proteasome, the cell's protein degradation machinery, which, in turn, may alter the half-life of key cell cycle regulatory proteins including, for example, cyclin dependent kinases (CDKs) which control the cell's division cycle. In fact, post mortem examinations of human ALS patients indicate that of CDK4 and CDK6 concentrations may be increased in neurons and CDK2 concentrations may be increased in astrocytes. Furthermore, activation and proliferation of astrocytes and microglia in humans and the mouse model astrocytes and microglia raise the possibility that generalized, non-specific inflammation and release of proliferative factors can directly cause aberrant cell cycle reentry and apoptosis in neurons as a result of increased CDK2 concentrations. Therefore, inhibition of cell cycle re-entry by inhibiting kinases such as, for example, CDK2, CDK4, and CDK6 could protect neurons from apoptosis, and might protect against astrocyte and microglial proliferation. Olomoucine is a known inhibitor of CDK2 and CDK5 that has been shown to arrests cells both in late G1 and at the G2/M transition (prophase/metaphase) of the cell cycle. Quinolin-2(1H)-one derivatives selectively inhibit cyclin-dependent kinase 5 (CDK5) which has been implicated in a number of neurodegenerative disorders such as, for example, Alzheimer's disease, ALS, and ischemic stroke. Roscovitine is a potent inhibitor of CDK1, CDK2, and CDK5 that has been shown to mediates neuropathology in Nieman's Pick Type C disease (a fatal neurodegenerative disorder). Tamoxifen has been widely used as a selective estrogen receptor modulator in the treatment of breast cancer, and a new mode of action for tamoxifen has been discovered which implicates it as a protein kinase C inhibitor with anti-glutamate activity. Excess of glutamate is believed to play a role in ALS due to its toxic effect on motor neurons.

In yet further embodiments, an effective amount of one or more agents Bcl inducers such, but are not limited to, ginsenoside Rb1, ginsenoside Rg1, G3139, oblimersen, and combinations thereof may be adjunctively administered with (R)-pramipexole. Ginsenosides Rb1 and ginsenoside Rg1 are extracted from ginseng root and appear to protect spinal neurons from excitotoxicity induced by glutamate and kainic acid, as well as oxidative stress, by stimulating Bcl expression. G3139 (oblimersen) is an 18-mer phosphorothioate oligo deoxy ribonucleotide antisense molecule, which is targeted to the initiation codon region of the Bcl-2 mRNA and effectively inhibits Bcl-2 transcription. Bcl-2 is a predominately integral membrane protein that is found in the outer mitochondrial membrane, endoplasmic reticulum, or outer nuclear membrane that is capable of forming ion channels in artificial membranes and can block the release of cytochrome c into the cytosol at least in part by correcting a defect in ATP/ADP exchange across the mitochondrial membrane. Cytochrome c forms an "apoptosome" complex with ATP, Apaf-1, and pro-caspase 9, which leads to the cleavage of the latter into an active peptide.

In some embodiments, an effective amount of one or more histone deacetylase (HDAC) inhibitors such as, but are not limited to, phenylbutyrate, scriptaid, valproic acid, and combinations thereof may be adjunctively administered with (R)-pramipexole. Transcription dysregulation may play a role in the pathogenesis of ALS. HDAC inhibitors can "desilence" a genome, allowing expression of genes that under normal situations would not be expressed thereby reversing this dysregulation. Sodium phenylbutyrate is an HDAC inhibitor that improves transcription and post-transcriptional pathways and promotes cell survival in a mouse model of motor neuron disease. Scriptaid is an HDAC inhibitor that changes the expression profile of protein factors that are involved in the recognition and binding of protein aggregates by the dynactin complex. Sodium valproate is an HDAC inhibitor that has been demonstrated to inhibit microglial cells hyperactivity and production of inflammatory mediators, appears to have protective effects in the superoxide dismutase (SOD) in mouse model of ALS, and stimulates stem cell activity, which may allow for regeneration of damaged motor neurons.

In other embodiments, an effective amount of one or more glial modulators such as, but are not limited to, ONO-2506 may be adjunctively administered with (R)-pramipexole. ONO-2506 lowers the potential for glutamate excitotoxicity by increasing the activity of glutamate transporters in astrocytes and has been shown to inhibit expansion of cerebral infarction by modulating the function of astrocytes. Early studies suggest that ONO-2506 may exhibit a neuroprotective effect by preventing irreversible injury to neurons in the brain.

In yet other embodiments, an effective amount of one or more mitochondrial energy promoters such as, but are not limited to, resveratrol, creatine, erythropoietin, cholest-4-en-3-One, oxime (TRO-19622) and combinations thereof may be adjunctively administered with (R)-pramipexole. Resveratrol is a powerful antioxidant found in red grape skins that has been found to suppress the influx of calcium into cells associated with glutamate-induced cell toxicity. Creatine aids in the formation of ATP, the primary source of cellular energy in the body, and has been shown to provide protective mechanisms against neurodegenerative disorders by stabilizing cellular membranes and mitochondrial energy-transfer complexes which may reduce motor neuron death by improving mitochondrial function. Creatine may also reduce oxidative stress and increase glutamate uptake and may help reduce the loss of muscle strength in ALS patients. Erythropoietin (EPO) is a glycoprotein hormone that controls erythropoiesis, red blood cell production that has recently been identified as a cytokine with various neuroprotective effects, including, for example, reduction of inflammation, enhancement of survival signals, and prevention of neuronal cell death. Cholest-4-en-3-one, oxime (TRO-19622) is a low molecular-weight compound shown to enhance motor neuron survival and growth by interacting with protein components of the mitochondrial permeability transition pore and that may rescue motor neuron cell bodies from axonomy-induced cell death in vivo.

In still other embodiments, an effective amount of one or more myostatin inhibitors such as, but are not limited to, ACE-031, MYO-029 and combinations thereof may be adjunctively administered with (R)-pramipexole. Myostatin is a negative regulator of muscle mass and inhibiting myostatin the body may be free to rebuild muscle tissue. The functional improvement of dystrophic muscle by myostatin blockade may provide a novel pharmacological strategy for treatment of diseases associated with muscle wasting such as DMD and ALS. ACE-031 is a myostatin inhibitor that was developed to treat diseases involving the loss of muscle mass, strength and function in diseases including muscular dystrophy, ALS, and cancer-related muscle loss. MYO-029 is a recombinant human antibody designed to bind to and inhibit the activity of myostatin.

In certain embodiments, an effective amount of one or more caspase inhibitors such as, but are not limited to, ESPA-1002, IDN-6556, pralnacasan, and combinations thereof may be adjunctively administered with (R)-pramipexole. Caspases are the mammalian cell death effector proteins that appear to be up-regulated in ALS. Apoptosis, programmed cell death, has been demonstrated to occur in the CNS, following both acute injury and during chronic neurodegenerative conditions such as ALS, and caspase inhibition has been demonstrated to be therapeutically effective in moderating excessive apoptosis. Therefore, targeted inhibition of caspases may represent a potential therapeutic option for treatment of neurodegenerative disorders. ESPA-1002 is a specific inhibitor of caspase 8 and caspase 9. IDN-6556 is a caspase inhibitor that has been shown to slow progression of ALS. Pralnacasan is an inhibitor of the inflammatory caspase interleukin-1-converting enzyme (ICE) and has been shown to significantly slow symptom progression of ALS.

Various embodiments of the invention are directed to multi-component therapeutics, multi-component systems, and pharmaceutical compositions in which (R)-pramipexole and one or more secondary therapeutic agents such as, for example, those listed above are provided in separate unit doses that are administered to a patient in need of treatment in separate, individual pharmaceutical compositions. Various other embodiments are directed to multi-component therapeutics, multi-component systems, and pharmaceutical compositions the include (R)-pramipexole and one or more secondary therapeutic agents such as those listed above in a single unit dose form that can be administered to a patient in need of treatment in a single pharmaceutical composition. In such embodiments, the separate, individual pharmaceutical compositions and the single pharmaceutical composition including both (R)-pramipexole and one or more secondary therapeutic agents may include one or more pharmaceutically acceptable adjuvant, carrier or excipient.

The multi-component therapeutics, multi-component systems, and pharmaceutical compositions are not limited by the type or secondary therapeutic agent and any of the secondary agents described above may be useful in embodiments of the invention. However, in particular embodiments, the secondary agent may be a dopamine agonist. For example, in one exemplary embodiment, the dopamine agonist may be ropinirole (Requip®), and in another exemplary embodiment, the dopamine agonist may be carbidopa/levodopa (Sinemet®). In other particular embodiments, the secondary agent may be an anti-glutamatergic. For example, in one exemplary embodiment, the secondary agent may be riluzole (Rilutek®). In yet other particular embodiments, the secondary agent may be an excitatory amino acid. For example, in one exemplary embodiment, the secondary agent may be talampanel. In still other particular embodiments, the secondary agent may be a growth factor. For example, in one exemplary embodiment, the secondary agent may be IPLEX. In further particular embodiments, the secondary agent may be a caspase inhibitor.

The multi-component therapeutics, multi-component systems, and pharmaceutical compositions, of some embodiments, may generally be used as neuroprotectants or to provide neuroprotection in a patient to which the compositions are administered. In other embodiments, the multi-component therapeutics, multi-component systems, and pharmaceutical compositions may be useful in the treatment of diseases related to neuronal degeneration or neuronal cell death or to alleviate the symptoms of such diseases by the action of a neuroprotectant. In still other embodiments, the multi-component therapeutics, multi-component systems, and pharmaceutical compositions of the invention may additionally be useful for restoring or improving neuronal, retinal and muscle function in patients, to treat neurodegenerative diseases, or diseases associated with mitochondrial dysfunction or increased oxidative stress, and in particular embodiments, the multi-component therapeutics, multi-component systems, and pharmaceutical compositions may be used to treat neurodegenerative dementias, neurodegenerative movement disorders, ataxia, seizure disorders, motor neuron disorders or diseases, and inflammatory demyelinating disorders in patients.

Embodiments of the invention are not limited to a particular mode of action. For instance, in some embodiments, the multi-component therapeutics, multi-component systems, and pharmaceutical compositions of the invention may be effective as inhibitors of oxidative stress or lipid peroxidation and may be useful in detoxification of oxygen radicals and normalization of mitochondrial function which may be useful in the treatment of numerous diseases. For example, increases in reactive oxygen species and other free radicals have been associated with ALS and at least in some cases may be the result of mutations in the SOD-1 gene which destroys superoxide radicals. In fact, the SOD-1 enzyme may play a pivotal role in the pathogenesis and progression of familial amyotrophic lateral sclerosis (FALS) which make up about 10% of all ALS patients are familial cases and of which 20% have mutations in the SOD-1 gene. Moreover, recent studies have linked premature neuronal death associated with ALS to mutated mitochondrial genes which lead to abnormalities in functioning of the energy production pathways in mitochondria. In other embodiments, the multi-component therapeutics, multi-component systems, and pharmaceutical compositions may be effective as treatment for impaired motor function in, for example, cardiac and striated muscle and retinal tissues which is associated with various degenerative diseases and neurodegenerative diseases such as ALS, Parkinson's disease, Alzheimer's disease, and macular degeneration. For example, in certain embodiments, the multi-component therapeutics, multi-component systems, and pharmaceutical compositions of the invention may be used in the treatment of age related macular degeneration. In such embodiment, the multi-component therapeutics, multi-component systems, and pharmaceutical compositions suitable for systemic administration, ocular administration or topical administration to the eye may be prepared. Therefore, the multi-component therapeutics, multi-component systems, and pharmaceutical compositions including (R)-pramipexole and the secondary agents provided above may be well suited for treatment of ALS, Parkinson's Disease, Alzheimer's disease, and macular degeneration. Any listing of disorders or diseases provided in discussion of the invention embodied herein is for exemplary purposes only and is not limiting in any way. Therefore, the compositions of the invention may be useful in the treatment of numerous unlisted disorders.

Further embodiments of the invention are directed methods of ameliorating the symptoms associated with degenerative and neurodegenerative diseases such as, for example, ALS, Parkinson's Disease, Alzheimer's disease, and macular degeneration by administering (R)-pramipexole and one or more secondary therapeutic agents such as dopamine agonists, dopaminergic agonists, COMT inhibitors, MOA inhibitors, excitatory amino acid antagonists, growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and downregulators, monoamine oxidase type B (MOAB) inhibitors, multi-target agents, kinase inhibitors, Bcl protein inducers, histone deacetylase (HDAC) mediators, glial modulators, mitochondrial energy promoting agents, myostatin inhibitors, caspase inhibitors and combinations thereof. For example, in some embodiments, the rate of cell death associated with neurodegenerative disorders such as Parkinson's disease and/or ALS may be reduced by administering the multi-component therapeutics, multi-component systems, and pharmaceutical compositions of various embodiments described above.

The pharmaceutical compositions of various embodiments may be suitable for oral administration, and in some embodiments, may be in a solid oral dosage form such as, for example, a tablet or a capsule.

In particular embodiments, the multi-component therapeutics, multi-component systems, and pharmaceutical compositions of the invention may include at least about 25 mg of (R)-pramipexole and less than about about 1.5 dopaminergic activity equivalents ("DAE"). Table 1 shows the DAE for a 25 mg dose of (R)-pramipexole as a function of a particular chiral purity of the (R)-pramipexole in the dose and the comparative binding affinity ratio. The embodiments for the amount of (R)-pramipexole in the multi-component therapeutics, multi-component systems, and pharmaceutical compositions, the DAE, chiral purity, and dosage form, which are described herein separately for the sake of brevity, can be joined in any suitable combination.

The chiral purity of the (R)-pramipexole in the multi-component therapeutics, multi-component systems, and pharmaceutical compositions of various embodiments of the invention may be at least 99.5%, at least 99.6%, at least 99.7%, at least 99.8%, at least 99.9%, at least 99.95%, or in particular embodiments, at least 99.99%. In certain embodiments, the chiral purity for (R)-pramipexole may be 100% or as close to 100% as can be measured. In some embodiments, the composition has a chiral purity for (R)-pramipexole of 99.9% or greater. In other embodiments, the composition has a chiral purity for (R)-pramipexole of 99.95% or greater. In still other embodiments, the composition has a chiral purity for (R)-pramipexole of 99.99% or greater.

In some embodiments, the multi-component therapeutics, multi-component systems, and pharmaceutical compositions of the invention may include less than about about 0.5 dopaminergic activity equivalents (DAE). In other embodiments, the multi-component therapeutics, multi-component systems, and the multi-component therapeutics, multi-component systems, and pharmaceutical compositions of the invention of the invention may include less than about 0.05 DAE. These DAE values are derived from the no observable adverse effect levels of (R)-pramipexole as discussed above. In some embodiments, the multi-component therapeutics, multi-component systems, and pharmaceutical compositions of the invention has a DAE which is less than the DAE as calculated from the maximum tolerated dose (MTD) amount or non-effective dose amounts of (S)-pramipexole. With reference to non-effective dose amounts of (S)-pramipexole, in some embodiments, the DAE does not exceed about 1.0, does not exceed about 0.75, does not exceed about 0.5, does not exceed about 0.25, or does not exceed about 0.125. With reference to MTD amount, the composition may have a DAE of below 1.5, below 0.3, or below 0.2.

In some embodiments, the multi-component therapeutics, multi-component systems, and pharmaceutical compositions may include at least about 50 mg of (R)-pramipexole. In other embodiments, the multi-component therapeutics, multi-component systems, and pharmaceutical compositions may include at least about 75 mg of (R)-pramipexole. In still other embodiments, multi-component therapeutics, multi-component systems, and pharmaceutical compositions may include at least about 125 mg of (R)-pramipexole. In yet other embodiments, the multi-component therapeutics, multi-component systems, and pharmaceutical compositions may include at least about 150 mg of (R)-pramipexole. In further embodiments, the multi-component therapeutics, multi-component systems, and pharmaceutical compositions may include at least about 200 mg of (R)-pramipexole. In yet further embodiments, the multi-component therapeutics, multi-component systems, and pharmaceutical compositions may include at least about 250 mg of (R)-pramipexole. In still further embodiments, the multi-component therapeutics, multi-component systems, and pharmaceutical compositions may include at least about 300 mg of (R)-pramipexole. In some embodiments, the multi-component therapeutics, multi-component systems, and pharmaceutical compositions may include at least about 400 mg of (R)-pramipexole. In other embodiments, the multi-component therapeutics, multi-component systems, and pharmaceutical compositions may include at least about 500 mg of (R)-pramipexole. In still other embodiments, the multi-component therapeutics, multi-component systems, and pharmaceutical compositions may include at least about 600 mg of (R)-pramipexole. In yet other embodiments, the multi-component therapeutics, multi-component systems, and pharmaceutical compositions may include at least about 750 mg of (R)-pramipexole. In some embodiments, the multi-component therapeutics, multi-component systems, and pharmaceutical compositions may include at least about 1000 mg of (R)-pramipexole.

In certain embodiments, the amount of (R)-pramipexole (mg) administered per kg body weight of the patient per day through the course of treatment using the multi-component therapeutics, multi-component systems, and pharmaceutical compositions of the invention may be from about 0.01 mg/kg/day to about 10,000 mg/kg/day, from about 1 mg/kg/day to about 1,000 mg/kg/day, from about 0.1 mg/kg/day to about 1,000 mg/kg/day, from about 1 mg/kg/day to about 1,000 mg/kg/day, from about 1,000 mg/kg/day to about 10,000 mg/kg/day, or from about 1 mg/kg/day to about 100 mg/kg/day. In some embodiments, the amount of (R)-pramipexole may be from about 3 mg/kg/day to about 70 mg/kg/day. In some embodiments, the amount of (R)-pramipexole may be from about 7 mg/kg/day to about 40 mg/kg/day. In some embodiment, the amount of (R)-pramipexole may be from about 3 mg/kg/day to about 50 mg/kg/day. In some embodiments, the dosage may be 10 mg/day to 1,500 mg/day, more preferably 100 mg/day to 600 mg/day. The amount of (R)-pramipexole in the compositions may be about 50 mg to about 5,000 mg, from about 100 mg to about 3,000 mg, from about 300 mg to about 1,500 mg, from about 500 mg to about 1,000 mg. In some embodiments, the amount of (R)-pramipexole in the compositions may be about from about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 200 mg, to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the amount of (R)-pramipexole is from about 600 mg to about 900 mg. In some embodiments, the amount of (R)-pramipexole is from about 50 mg to about 5000 mg. In some embodiments, the amount of (R)-pramipexole is from about 100 mg to about 3000 mg. In some embodiments, the amount of (R)-pramipexole is from about 300 mg to about 1500 mg. In some embodiments, the amount of (R)-pramipexole is from about 500 mg to about 1000 mg.

In some embodiments, a starting daily dose of (R)-pramipexole may be equal to the daily dose of (R)-pramipexole administered throughout the course of treatment. For example, in embodiments in which the daily dose of (R)-pramipexole is 5000 mg/day, the starting daily dose may be 5000 mg per day, and this daily dose may be maintained throughout treatment. In other embodiments, (R)-pramipexole may be titrated such that the starting daily dose may of (R)-pramipexole may be less than 5000 mg, for example, 500 mg or 100 mg, and the daily dose may be increased every day, every other day, or per week until the required daily dose of, for example, 5000 mg is reached. In such embodiments, the starting daily dose may vary. For example, in some embodiments, the starting daily dose may be at least about 25 mg of (R)-pramipexole. In some embodiments, the starting daily dose may be at least about 50 mg of (R)-pramipexole. In some embodiments, the starting daily dose may be at least about 75 mg of (R)-pramipexole. In some embodiments, the starting daily dose may be at least about 125 mg of (R)-pramipexole. In some embodiments, the starting daily dose may be at least about 150 mg of (R)-pramipexole. In some embodiments, the starting daily dose may be at least about 200 mg of (R)-pramipexole. In some embodiments, the starting daily dose may be at least about 300 mg of (R)-pramipexole. In some embodiments, the starting daily dose may be at least about 400 mg of (R)-pramipexole. In some embodiments, the starting daily dose may be at least about 500 mg of (R)-pramipexole. In some embodiments, the starting daily dose may be at least about 600 mg of (R)-pramipexole. In some embodiments, the starting daily dose may be at least about 750 mg of (R)-pramipexole. In some embodiments, the starting daily dose may be at least about 1000 mg of (R)-pramipexole. In some embodiments, the starting daily dose may be from about 600 mg to about 900 mg of (R)-pramipexole. In still other embodiments, the a starting daily dose of (R)-pramipexole may be greater than the daily dose of (R)-pramipexole administered throughout the course of treatment. For example, in some embodiments the starting daily dose may be about 5000 mg and the daily dose may be decreased every day, every other day, or per week until the required daily dose of, for example, 500 or 100 mg is reached.

The starting daily dose amount of (R)-pramipexole in the compositions may preferably be about 50 mg to about 5,000 mg, from about 100 mg to about 3,000 mg, from about 300 mg to about 1,500 mg, from about 500 mg to about 1,000 mg. In some embodiments, the starting daily dose amount of (R)-pramipexole in the compositions may be about from about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 200 mg, to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the starting daily dose amount of (R)-pramipexole is from about 600 mg to about 900 mg. This dose may be administered as a single daily dose, or may be divided into several doses administered throughout the day, for example, 1 to 5 doses per day, preferably two to three doses per day. In some embodiments, the starting daily dose amount of (R)-pramipexole is from about 50 mg to about 5000 mg. In some embodiments, the starting daily dose amount of (R)-pramipexole is from about 100 mg to about 3000 mg. In some embodiments, the starting daily dose amount of (R)-pramipexole is from about 300 mg to about 1500 mg. In some embodiments, the starting daily dose amount of (R)-pramipexole is from about 500 mg to about 1000 mg.

In such embodiments, the starting daily dose amount of (R)-pramipexole may be from about 0.01 mg/kg/day to about 10,000 mg/kg/day, from about 1 mg/kg/day to about 1,000 mg/kg/day, from about 0.1 mg/kg/day to about 1,000 mg/kg/day, from about 1 mg/kg/day to about 1,000 mg/kg/day, from about 1,000 mg/kg/day to about 10,000 mg/kg/day, or from about 1 mg/kg/day to about 100 mg/kg/day. In some embodiments, the starting daily dose amount of (R)-pramipexole may be from about 3 mg/kg/day to about 70 mg/kg/day. In some embodiments, the starting daily dose amount of (R)-pramipexole may be from about 7 mg/kg/day to about 40 mg/kg/day. In some embodiment, the starting daily dose amount of (R)-pramipexole may be from about 3 mg/kg/day to about 50 mg/kg/day. In some embodiments, the starting daily dose amount may be 10 mg/day to 1,500 mg/day, more preferably 100 mg/day to 600 mg/day.

The amount of each, individual secondary agent of the one or more secondary agents in the pharmaceutical compositions of the invention may vary depending on, for example, the secondary agent utilized. In some embodiments, the amount of the one or more secondary agent in the pharmaceutical composition may be the amount suggested by the manufacture as a daily dose, starting daily dose, or dose per kg patient weight, per day. For example, the amount of each, individual secondary agent of the one or more secondary agents in the compositions of various embodiments of the invention may be from about 2 mg to about 5,000 mg, from about 10 mg to about 3,000 mg, from about 30 mg to about 1,500 mg, from about 50 mg to about 1,000 mg. In some embodiments, the amount of each, individual secondary agent of the one or more secondary agents in such compositions may be about from about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 200 mg, to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the amount of each, individual secondary agent of the one or more secondary agents may be from about 600 mg to about 900 mg. In some embodiments, the amount of each, individual secondary agent of the one or more secondary agents may be from about 50 mg to about 5000 mg. In some embodiments, the amount of each, individual secondary agent of the one or more secondary agents may be from about 100 mg to about 3000 mg. In some embodiments, the amount of each, individual secondary agent of the one or more secondary agents may be from about 300 mg to about 1500 mg. In some embodiments, the amount of each, individual secondary agent of the one or more secondary agents may be from about 500 mg to about 1000 mg.

In some embodiments, the multi-component therapeutics, multi-component systems, and pharmaceutical compositions of various embodiments of the invention may include, for example, microcrystalline cellulose, mannitol, croscarmellose sodium, magnesium stearate, or combination thereof. For example, certain embodiments of the invention include a pharmaceutical formulation including (R)-pramipexole and, in some embodiments, one or more secondary agents, about 20% to about 50% by weight of the formulation of one or more microcrystalline cellulose; about 10% to about 30% by weight mannitol; about 2% to about 6% crospovidone; and about 0.01% to about 2% magnesium stearate. In some embodiments, the pharmaceutical composition may include a diluent in an amount from about 20% to about 50% by weight of the formulation, and in certain embodiments, the formulation may include about 10% to about 30% by weight of a second diluent. In still other embodiments, the formulation may include about 2% to about 6% of a disintegrant and in yet other embodiments, about 0.01% to about 2% of a lubricant. In some embodiments, the multi-component therapeutics, multi-component systems, and pharmaceutical compositions such as those described above may be suitable for oral administration, and in particular embodiments, the multi-component therapeutics, multi-component systems, and pharmaceutical compositions may be a solid oral dosage form.

In such formulations, the (R)-pramipexole may have a chiral purity of at least 99.5%, at least 99.6%, at least 99.7%, at least 99.8%, at least 99.9%, preferably at least 99.95%, or at least 99.99%. In some embodiments, the chiral purity for (R)-pramipexole may be about 100%. In some embodiments, of such formulations (R)-pramipexole may have a chiral purity of 99.9% or greater, 99.95% or greater, or 99.99% or greater.

The amount of (R)-pramipexole in such formulations may be about 50 mg to about 5,000 mg, from about 100 mg to about 3,000 mg, from about 300 mg to about 1,500 mg, from about 500 mg to about 1,000 mg. In some embodiments, the starting daily dose amount of (R)-pramipexole in the formulation may be about from about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 200 mg, to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments of the formulation, (R)-pramipexole may be from about 600 mg to about 900 mg. In some embodiments the multi-component therapeutics, multi-component systems, and pharmaceutical compositions of the invention may include (R)-pramipexole having about 25 neuroprotective activity equivalents and less than about 1.5 dopaminergic activity equivalents. In other embodiments, the multi-component therapeutics, multi-component systems, and pharmaceutical compositions of the invention may have less than about 0.5 dopaminergic activity equivalents or less than about 0.05 dopaminergic activity equivalents.

In some embodiments, the multi-component therapeutics, multi-component systems, and pharmaceutical compositions may have at least about 50, at least about 75, at least about 125, at least about 150, at least about 200, at least about 300, at least about 400, at least about 500, at least about 750, at least about 750, or at least about 100 neuroprotective activity equivalents. In some embodiments, the multi-component therapeutics, multi-component systems, and pharmaceutical compositions may have from about 50 to about 5,000, from about 100 to about 3,000, from about 300 to about 1,500, from about 500 to about 1,000, from about 25 to about 5,000, from about 100 to about 5,000, from about 200 to about 5,000, from about 250 to about 5,000, from about 300 to about 5,000, from about 400 to about 5,000, from 450 to about 5,000, from about 200, to about 3,000, from about 250 to about 3,000, from about 300 to about 3,000, from about 400 to about 3,000, from 450 to about 3,000, from about 100 to about 1,000, from about 200 to about 1,000, from about 250 to about 1,000, from about 300 to about 1,000, from about 400 to about 1,000, from about 600 to about 1,000, from 450 to about 1,000, or from about 600 to about 900 neuroprotective activity equivalents.

The embodiments for the neuroprotective activity equivalents, dopaminergic activity equivalents, and dosage forms in the multi-component therapeutics, multi-component systems, and pharmaceutical compositions of the invention, which are described herein separately for the sake of brevity, can be joined in any suitable combination.

Methods of Treatment, Uses, and Compositions and Compounds for Use

Embodiments of the invention further provide methods for treating a neurodegenerative disease by administering a therapeutically effective amount of (R)-pramipexole and a therapeutically effective amount of one or more secondary agents. As such in some embodiments, (R)-pramipexole and, in some embodiments, one or more secondary agents may be formulated as a pharmaceutical or therapeutic composition by combining with one or more pharmaceutically acceptable carriers. Embodiments include pharmaceutical or therapeutic compositions that may be administered orally, preferably as a solid oral dose, and more preferably as a solid oral dose that may be a capsule or tablet. In a preferred embodiment, the pharmaceutical or therapeutic composition may be formulated in tablet or capsule form for use in oral administration routes. The compositions and amounts of non-active ingredients in such a formulation may depend on the amount of the active ingredient, and on the size and shape of the tablet or capsule. Such parameters may be readily appreciated and understood by one of skill in the art. The therapeutically effective amount of (R)-pramipexole may be effective as an inhibitor of oxidative stress, an inhibitor of lipid peroxidation or in detoxification of oxygen radicals. Exemplary neurodegenerative disorders which may be treated using the methods of various embodiments, include, for example, Parkinson' disease or symptoms thereof and ALS or symptoms thereof. In one embodiment, Parkinson's disease and/or symptoms thereof are treated with the combination of (R)-pramipexole and one or more secondary agents wherein the (R)-pramipexole and one or more secondary agents may be administered in a single or multiple formulations.

For example, in various embodiments, a daily (R)-pramipexole may be administered in combination with one or more secondary agents. For example, (R)-pramipexole may be administered to a patient in need of treatment simultaneously with one or more secondary agents. In such embodiments, the (R)-pramipexole and the one or more secondary agents may be combined in a single unit dosage form, or separate unit dosages of (R)-pramipexole and the one or more secondary agents may be administered simultaneously or within a relatively short amount of time. In other embodiments, (R)-primipexole may be administered alone in a unit dosage and one or more secondary agents may be administered in a separate unit dosage at different times. For example, (R)-pramipexole may be administered to a patient in need of treatment and a separate unit dose of one or more secondary agent may be administered one or more hour later than administration or (R)-prepexole. In some embodiments, (R)-pramipexole may be administered in combination with one or more secondary agents and alone during the same course of treatment. For example, in particular embodiments, a unit dose of (R)-pramipexole combined with one or more secondary agents may be administered, and at various other times throughout a 24 hour period, individual unit doses of (R)-pramipexole or the one or more secondary agents may be administered separately. Such embodiments may accommodate any treatment schedule required to administer an effective daily dose of (R)-pramipexole and/or the one or more secondary agents in multiple or divided doses.

The methods of various embodiments of the invention may constitute a course of treatment and may be carried out for any length of time. For example, in some embodiments, a course of treatment may include a schedule of administrations wherein (R)-pramipexole and/or one or more secondary therapeutic agents are administered one or more times in a 24-hour period for, for example, 5 days or more. In other embodiments, a course of treatment may include repeating administering (R)-pramipexole and/or administering one or more secondary therapeutic agents one or more times in a 24-hour period for, for example, 5 days to one or more years. In still other embodiments, a course of treatment include repeated administration of (R)-pramipexole and/or one or more secondary therapeutic agents may be carried out indefinitely, or for the lifetime of the patient who is undergoing the course of treatment.

In certain embodiments, one course of treatment may be followed by another course of treatment. For example, in some embodiments, a first course of treatment in which (R)-pramipexole is administered in a first therapeutically effective amount and one or more secondary therapeutic agents administered at a therapeutically effective amount may be carried out for a period of time such as, for example, 5 days to one or more months or one or more year. A second course of treatment may carried out a the conclusion of the first course of treatment, and the second course of treatment may include, for example, a second therapeutically effective amount of (R)-pramipexole that is different than the first therapeutically effective amount, a therapeutically effective amount of one or more secondary therapeutic agents that is different than the therapeutically effective amount administered in the first course of treatment, one or more secondary therapeutic agents that are different than the one or more secondary therapeutic agents administered in the first course of treatment, or a combination thereof. Differences in the first and second courses of treatment may vary depending on the subject to whom the courses of treatment is administered and may depend, for example, on the subject's reaction to the treatment or changes in the symptoms or severity of symptoms exhibit by the subject as a result of the treatment. The skilled artisan may observe such variations and alter the course of treatment appropriately for each individual subject.

Further embodiments of the invention include methods of treating neurodegenerative disorders or the symptoms associated with neurodegenerative disorders such as, for example, Parkinson's disease and/or ALS and methods of ameliorating the symptoms associated therewith using the multi-component therapeutics, multi-component systems, and pharmaceutical compositions of the invention by administering (R)-pramipexole and one or more secondary therapeutic agents such as, for example, dopamine agonists, dopaminergic agonists, COMT inhibitors, MOA inhibitors, excitatory amino acid antagonists, growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and downregulators, monoamine oxidase type B (MOAB) inhibitors, multi-target agents, kinase inhibitors, Bcl inducers, histone deacetylase (HDAC) mediators, glial modulators, mitochondrial energy promoting agents, myostatin inhibitors, caspase inhibitors and combinations thereof.

Further embodiments of the invention are directed to methods of decreasing the rate of cell death associated with neurodegenerative disorders such as, for example, Parkinson's disease and/or ALS using the multi-component therapeutics, multi-component systems, and pharmaceutical compositions of the invention by administering (R)-pramipexole and one or more secondary therapeutic agents such as, for example, dopamine agonists, dopaminergic agonists, COMT inhibitors, MOA inhibitors, excitatory amino acid antagonists, growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and downregulators, monoamine oxidase type B (MOAB) inhibitors, multi-target agents, kinase inhibitors, Bcl inducers, histone deacetylase (HDAC) mediators, glial modulators, mitochondrial energy promoting agents, myostatin inhibitors, caspase inhibitors and combinations thereof.

The (R)-pramipexole of such embodiments may have a chiral purity of at least 99.5%, at least 99.6%, at least 99.7%, at least 99.8%, at least 99.9%, at least 99.95% and at least 99.99%, and in certain embodiments, the R-pramipexole may have a chiral purity of about 100%.

In some embodiments, a therapeutically effective amount of (R)-pramipexole may be administered to effectuate treatment and such a therapeutically effective amount may be from about 0.01 mg/kg/day to about 10,000 mg/kg/day, from about 1 mg/kg/day to about 1,000 mg/kg/day, from about 0.1 mg/kg/day to about 1,000 mg/kg/day, from about 1 mg/kg/day to about 1,000 mg/kg/day, from about 1,000 mg/kg/day to about 10,000 mg/kg/day, or from about 1 mg/kg/day to about 100 mg/kg/day. In some embodiments, the therapeutically effective amount of (R)-pramipexole may be from about 3 mg/kg/day to about 70 mg/kg/day. In some embodiments, the therapeutically effective amount of (R)-pramipexole may be from about 7 mg/kg/day to about 40 mg/kg/day. In some embodiment, the therapeutically effective amount of (R)-pramipexole may be from about 3 mg/kg/day to about 50 mg/kg/day. In some embodiments, the dosage may be 10 mg/day to 1,500 mg/day, more preferably 100 mg/day to 600 mg/day. In some embodiments, the therapeutically effective amount of (R)-pramipexole may be from about 50 mg to about 5,000 mg, from about 100 mg to about 3,000 mg, preferably from about 300 mg to about 1,500 mg, or more preferably from about 500 mg to about 1,000 mg. In some embodiments, the therapeutically effective amount of (R)-pramipexole may be from about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 200 mg to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the therapeutically effective amount of (R)-pramipexole is from about 600 mg to about 900 mg. This dose may be administered as a single daily dose, or may be divided into several doses administered throughout the day, for example, 1 to 5 doses per day, preferably two to three doses per day.

In some embodiments, the daily dose amount of (R)-pramipexole in such methods may be from about 0.01 mg/kg/day to about 10,000 mg/kg/day, from about 1 mg/kg/day to about 1,000 mg/kg/day, from about 0.1 mg/kg/day to about 1,000 mg/kg/day, from about 1 mg/kg/day to about 1,000 mg/kg/day, from about 1,000 mg/kg/day to about 10,000 mg/kg/day, or from about 1 mg/kg/day to about 100 mg/kg/day. In some embodiments, the daily dose amount of (R)-pramipexole may be from about 3 mg/kg/day to about 70 mg/kg/day. In some embodiments, the daily dose amount of (R)-pramipexole may be from about 7 mg/kg/day to about 40 mg/kg/day. In some embodiment, the daily dose amount of (R)-pramipexole may be from about 3 mg/kg/day to about 50 mg/kg/day. In some embodiments, the daily dose amount may be 10 mg/day to 1,500 mg/day, more preferably 100 mg/day to 600 mg/day. In some embodiments, the daily dose amount of (R)-pramipexole is from about 50 mg to about 5,000 mg, from about 100 mg to about 3,000 mg, from about 300 mg to about 1,500 mg, or from about 500 mg to about 1,000 mg. In some embodiments, the daily dose amount of (R)-pramipexole is from about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 200 mg to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the daily dose amount of (R)-pramipexole may be from about 600 mg to about 900 mg. In some embodiments, the daily dose amount may be from about 500 mg to about 1,000 mg of (R)-pramipexole. In some embodiments, daily dose amount may be from about 50 mg to about 5,000 mg of (R)-pramipexole. In some embodiments, the daily dose amount may be from about 100 mg to about 3,000 mg of (R)-pramipexole. In some embodiments, daily dose amount may be from about 200 mg to about 3,000 mg of (R)-pramipexole. In some embodiments, daily dose amount may be from about 300 mg to about 1,500 mg of (R)-pramipexole. In some embodiments, daily dose amount may be from about 500 mg to about 1,000 mg of (R)-pramipexole. This dose may be administered as a single daily dose, or may be divided into several doses administered throughout the day, for example, 1 to 5 doses per day, preferably two to three doses per day.

In some embodiments, the daily dose amount may further include an amount of (S)-pramipexole that produces no observable adverse effect. In such embodiments, a no observable effective dose amount of (S)-pramipexole may be below 1.5 mg, below 0.5 mg, or below 0.05 mg per day. In other embodiments, the daily dose amount may further include a non-effective dose amount of (S)-pramipexole. In such embodiments, a non-effective dose amount of (S)-pramipexole may be an amount not exceeding 1.0 mg per day. In other embodiments, the non-effective dose amount of (S)-pramipexole may be an amount that does not exceed 0.75 mg/day, 0.5 mg/day, 0.25 mg/day, or 0.125 mg/day.

In some embodiments of the methods of the invention, the daily dose amount of (R)-pramipexole may be about 100 mg to about 3,000 mg and the chiral purity of the (R)-pramipexole may be 99.95% or greater. In other embodiments, the daily dose amount of (R)-pramipexole may be about 200 to about 3,000 mg and the chiral purity of the (R)-pramipexole may be 99.95% or greater. In still other embodiments, the daily dose amount of (R)-pramipexole may be about 300 to about 1,500 mg and the chiral purity of the (R)-pramipexole may be 99.95% or greater. In yet other embodiments of the methods, the daily dose amount of (R)-pramipexole may be from about 500 mg to about 1,000 mg and the chiral purity of the (R)-pramipexole may be 99.95% or greater.

In further embodiments of the methods, the daily dose amount of (R)-pramipexole may be from about 100 mg to about 3,000 mg and the daily dose amount may include less than about 0.05 mg of (S)-pramipexole. In some embodiments, the daily dose amount of (R)-pramipexole may be from about 200 mg to about 3,000 mg and the daily dose amount may include less than about 0.05 mg of (S)-pramipexole. In other embodiments, the daily dose amount of (R)-pramipexole may be from about 300 to about 1,500 mg, and the daily dose amount may include less than about 0.05 mg of (S)-pramipexole. In yet other embodiments, the daily dose amount of (R)-pramipexole may be from about 500 mg to about 1,000 mg and the daily dose amount may include less than about 0.05 mg of (S)-pramipexole.

The embodiments for disease states, patient type (naïve vs. not naïve), daily dose amounts, no observable adverse effect level dose amounts, non-effective dose amounts, and chiral purities for the methods of the invention, which are described herein separately for the sake of brevity, can be joined in any suitable combination.

Kits

Some embodiments of the invention include kits that may include the multi-component therapeutics, multi-component systems, and pharmaceutical compositions of the invention including (R)-pramipexole and one or more secondary therapeutic agents such as, for example, dopamine agonists, dopaminergic agonists, COMT inhibitors, MOA inhibitors, excitatory amino acid antagonists, growth factors, neurotrophic factors, antioxidants, anti-inflammatory agents, immunomodulators, anti-glutamatergics, ion channel blockers, α-amino-3-hydroxy-5-methyl-4-isoxazolepropionic acid (AMPA) receptor antagonists, heat shock protein inducers/protein disaggregators and downregulators, monoamine oxidase type B (MOAB) inhibitors, multi-target agents, kinase inhibitors, Bcl inducers, histone deacetylase (HDAC) mediators, glial modulators, mitochondrial energy promoting agents, myostatin inhibitors, caspase inhibitors and combinations thereof, and instructions for administering or prescribing the one or more pharmaceutical compositions. In such embodiments, a direction may be included to administer or prescribe to a patient the multi-component therapeutics, multi-component systems, and pharmaceutical compositions of the invention at a starting daily dose of at least about 50 mg to about 5,000 mg of (R)-pramipexole and a therapeutically effective amount of one or more second therapeutic agents. In addition, in some embodiments, kits may include one or more pharmaceutical compositions such as those described in any of the embodiments of the compositions described herein, or any combination thereof, and instructions for administering or prescribing to a patient the one or more pharmaceutical compositions such as, for example, a direction to administer or prescribe the one or more pharmaceutical compositions or any combination thereof.

The (R)-pramipexole for use in the kits of the invention may have a chiral purity of at least 99.5%, preferably at least 99.6%, preferably at least 99.7%, preferably at least 99.8%, preferably at least 99.9%, preferably at least 99.95% and more preferably at least 99.99%. In particular embodiments, the chiral purity for the R-pramipexole may be 100%. In other embodiments, (R)-pramipexole may have a chiral purity of 99.9% or greater, 99.95% or greater, or 99.99% or greater.

In some embodiments, the instructions may include an instruction to administer or prescribe to a patient in need of treatment the multi-component therapeutics, multi-component systems, and pharmaceutical compositions of the invention in accordance with the embodiments described above at a starting daily dose of (R)-pramipexole of from about 0.1 mg/kg/day to about 1,000 mg/kg/day or from about 1 mg/kg/day to about 100 mg/kg/day. In some embodiments, the instructions may include an instruction to administer or prescribe to a patient the multi-component therapeutics, multi-component systems, and pharmaceutical compositions of the invention at a starting daily dose of (R)-pramipexole of from about 3 mg/kg/day to about 70 mg/kg/day or from about 7 mg/kg/day to about 40 mg/kg/day. In other embodiments, the instructions may include an instruction to administer or prescribe to a patient the multi-component therapeutics, multi-component systems, and pharmaceutical compositions of the invention at a starting daily dose of (R)-pramipexole of from about 50 mg to about 5,000 mg, from about 100 mg to about 3,000 mg, from about 300 mg to about 1,500 mg, or from about 500 mg to about 1,000 mg. In some embodiments, the instructions may include a direction to administer or prescribe to a patient the multi-component therapeutics, multi-component systems, and pharmaceutical compositions of the invention at a starting daily dose of (R)-pramipexole of from about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 200 mg to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the starting daily dose amount of (R)-pramipexole may be from about 600 mg to about 900 mg. The doses described above may be administered as a single daily dose, or may be divided into several doses administered throughout the day, for example, 1 to 5 doses per day, preferably two to three doses per day, and the instructions of various embodiments may describe such divided administrations.

In some embodiments, the instructions comprise a direction to administer or prescribe the multi-component therapeutics, multi-component systems, and pharmaceutical compositions of the invention in an amount sufficient to result in administration of a starting daily dose of from about 100 mg to about 3,000 mg of (R)-pramipexole to a patient. In some embodiments, instructions may include a direction to administer or prescribe the multi-component therapeutics, multi-component systems, and pharmaceutical compositions of the invention in an amount sufficient to result in administration of a starting daily dose of from about 200 mg to about 3,000 mg of (R)-pramipexole to a patient. In some embodiments, the instructions comprise a direction to administer or prescribe the multi-component therapeutics, multi-component systems, and pharmaceutical compositions of the invention in an amount sufficient to result in administration of from about 300 to about 1,500 mg of (R)-pramipexole to a patient. In some embodiments, the instructions comprise a direction to administer or prescribe the multi-component therapeutics, multi-component systems, and pharmaceutical compositions of the invention in an amount sufficient to result in administration of a starting daily dose of from about 500 to about 1,000 mg of (R)-pramipexole to a patient.

The multi-component therapeutics, multi-component systems, and pharmaceutical compositions of the invention of the invention may be prepared, packaged, sold in bulk, as a single unit dose, or as multiple unit doses. The various compositions associated with the multi-component therapeutics, multi-component systems, and pharmaceutical compositions of the invention may be formulated to be administered orally, ophthalmically, intravenously, intramuscularly, intra-arterially, intramedularry, intrathecally, intraventricularly, transdermally, subcutaneously, intraperitoneally, intravesicularly, intranasally, enterally, topically, sublingually, or rectally. The various compositions of the invention may be administered orally, preferably as a solid oral dose, and more preferably as a solid oral dose that may be a capsule or tablet. In some embodiments, the compositions of the invention may be formulated as tablets for oral administration.

The multi-component therapeutics, multi-component systems, and pharmaceutical compositions of the invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, intravesicularly, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

The doses of the (R)-pramipexole and one or more second therapeutic agents which may be administered to a patient in need thereof in the multi-component therapeutics, multi-component systems, and pharmaceutical compositions of the invention may range between about 0.1 mg/kg per day and about 1,000 mg/kg per day. This dose may be administered as a single daily dose, or may be divided into several doses which are administered throughout the day, such as 1 to 5 doses, or two to three doses per day. The route of administration may include oral, sublingual, transdermal, rectal, or any accessible parenteral route. One of ordinary skill in the art will understand and appreciate the dosages and timing of the dosages to be administered to a patient in need thereof. The doses and duration of treatment may vary, and may be based on assessment by one of ordinary skill in the art based on monitoring and measuring improvements in neuronal and non-neuronal tissues. This assessment may be made based on outward physical signs of improvement, such as increased muscle control, or on internal physiological signs or markers. The doses may also depend on the condition or disease being treated, the degree of the condition or disease being treated and further on the age and weight of the patient.

Specific modes of administration will depend on the indication. The selection of the specific route of administration and the dose regimen or course of treatment may be adjusted or titrated by the clinician according to methods known to the clinician in order to obtain the optimal clinical response. The amount of compound to be administered may be that amount which is therapeutically effective. The dosage to be administered may depend on the characteristics of the subject being treated, e.g., the particular animal or human subject treated, age, weight, health, types of concurrent treatment, if any, and frequency of treatments, and can be easily determined by one of skill in the art (e.g., by the clinician).

Pharmaceutical formulations containing the various compounds of the invention and a suitable carrier may also be any number of solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics,* 6th Edition, MacMillan Publishing Co., New York (1980) can be consulted.

In particular embodiments, the route of administration of the compositions of the invention may be oral, with a more preferable route being in the form of tablets, capsules, lozenges and the like. In such embodiments, the compositions of the present invention may be formulated as tablets for oral administration. A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent.

The tablets may be uncoated or they may be coated by known techniques, optionally to delay disintegration and absorption in the gastrointestinal tract and thereby providing a sustained action over a longer period. The coating may be adapted to release the active compound in a predetermined pattern (e.g., in order to achieve a controlled release formulation) or it may be adapted not to release the active compound until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed. The solid tablet compositions may include a coating adapted to protect the composition from unwanted chemical changes, (e.g., chemical degradation prior to the release of the active drug substance).

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal or sublingual administration, the compositions can take the form of tablets, flash melts or lozenges formulated in any conventional manner.

The compounds of the present invention can be formulated for parenteral administration by injection, e.g., by bolus injection or continuous infusion. The compounds can be administered by continuous infusion over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical and therapeutic compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

Preparation of (R)- and (S)-Pramipexole

Processes for the preparation of pramipexole are described in U.S. Pat. No. 4,843,086 and U.S. Pat. No. 4,886,812 to Griss et al., each of which is incorporated by reference in its entirety. The (R)-pramipexole of the present invention may be synthesized and/or purified by methods disclosed in the U.S. Provisional Application No. 60/894,829 entitled "Methods of Synthesizing and Purifying R(+) and (S)-pramipexole", filed on Mar. 14, 2007, and U.S. Provisional Application No. 60/894,814 entitled "Methods of Enantiomerically Purifying Chiral Compounds", filed on Mar. 14, 2007, which are incorporated herein by reference in their entireties. Specifically, preparations of pramipexole which are chirally pure for the R(+) enantiomer may be produced using a bi-molecular nucleophilic substitution ($S_N2$) reaction. A diamine, 2,6 diamino-4,5,6,7-tetrahydrobenzothiazole, is reacted with a propyl sulfonate or a propyl halide in polar solvents to generate an insoluble pramipexole salt in a one pot synthesis scheme. The pramipexole salt reaction product displays a high chemical purity and an increased optical purity over the reactants, which may be due to limited solubility of the pramipexole salt in the polar solvents of the reaction mixture. Purification of the final pramipexole synthesis product from the reaction mixture thus involves simple trituration and washing of the precipitated pramipexole salt in a volatile solvent such as an alcohol or heptane, followed by vacuum drying.

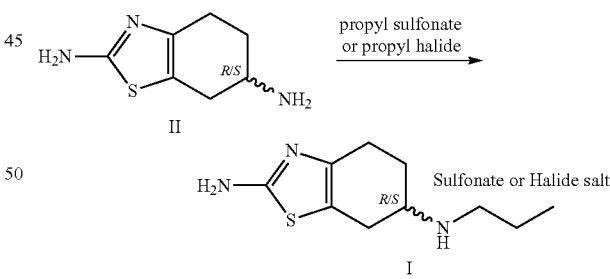

In some embodiments, the (R)-pramipexole is prepared by dissolving a diamine of formula 2,6 diamino-4,5,6,7-tetrahydro-benzothiazole in an organic solvent, reacting the diamine with a propyl sulfonate or a propyl halide under conditions sufficient to generate and precipitate the pramipexole salt, and recovering the pramipexole salt. In a preferred embodiment, the propyl sulfonate may be propyl tosylate. In a further embodiment, the propyl halide may be propyl bromide. The pramipexole salt reaction product of this process displays a high chemical purity and an increased optical purity over the reactants. Without wishing to be bound by theory, the increased optical purity may be due to limited solubility of the pramipexole salt reaction product in the polar solvents of the reaction mixture. Purification of the final pramipexole reaction product from the reaction mixture thus involves simple trituration and washing of the precipitated pramipexole salt in a volatile solvent such as an alcohol or heptane, followed by vacuum drying.

In embodiments of the process, the diamine may be an R(+) diamine, or a mixture of the R(+) and an S diamine. The chemical purity of the final pramipexole salt may be at least about 97% or greater, preferably 98% or greater, more preferably 99% or greater. The R(+) enantiomers of the pramipexole salt generated using this process are generated from starting diamines which may be at least 55% optically pure, preferably 70% optically pure, and more preferably greater than 90% optically pure. The final pramipexole product may be enriched to 99.6% optical purity or greater, 99.7% optical purity or greater, preferably 99.8% optically purity or greater, and more preferably 99.9% optical purity or greater, 99.95% optical purity or greater, 99.99% optical purity or greater. In some embodiments, the optical purity may be 100%.

In embodiments of the process, the organic solvent may be a polar aprotic solvent such as tetrahydofuran, dimethylformamide, dimethyl sulfoxide, dimethylacetamide, or hexamethylphosphoric triamide. The organic solvent may also be a low molecular weight alcohol such as ethanol, 1-propanol, or n-butanol. Further, the organic solvent may be any combination of the polar aprotic solvents and low molecular weight alcohols. The organic solvent may have a water content of from about 0 to about 10 volume percent. Preferably, the solvents used in the practice of this invention are standard ACS grade solvents. Further, the propyl sulfonate or a propyl halide may be added at about 1.0 to about 2.0 molar equivalents of the diamine.

In further embodiments of the process, the conditions sufficient to generate and precipitate the pramipexole salt may comprise heating the dissolved diamine at an elevated temperature, adding the propyl sulfonate or propyl halide which may be dissolved in di-isoprolyethylamine and an organic solvent to form a mixture, and stirring the mixture for about 4 hours. Alternatively, the di-isoprolyethylamine may be added to the reaction with the diamine, and the propyl sulfonate or propyl halide may be dissolved in an organic solvent to form a mixture, which may be added to the reaction with stirring over about 4 hours.

In this embodiment, the elevated temperature of the reaction may be below the boiling temperature of the reaction, specifically, below the boiling temperature of the organic solvent(s) of the reaction mixture. The elevated temperature may be lower than about 125° C., preferably lower than about 100° C., and more preferably about 95° C. or lower. The times necessary for the reaction may vary with the identities of the reactants, the solvent system and with the chosen temperature.

In an alternative embodiment, the conditions sufficient to generate and precipitate the pramipexole salt may comprise using dimethylformamide as the organic solvent, heating the dissolved diamine at an elevated temperature, adding the propyl sulfonate or propyl halide which is dissolved in dimethylformamide to form a mixture, and stirring the mixture for about 4 hours. The elevated temperature of the reaction may be below the boiling temperature of the reaction, specifically, below the boiling temperature of the organic solvent(s) of the reaction mixture. The elevated temperature may be lower than about 125° C., preferably lower than about 100° C., and more preferably about 75° C. or lower. The times necessary for the reaction may vary with the identities of the reactants, the solvent system and with the chosen temperature.

In a preferred alternative embodiment, the conditions sufficient to generate and precipitate the pramipexole salt comprise using dimethylformamide as the organic solvent and heating the dissolved diamine at an elevated temperature. A mixture of propyl sulfonate or propyl halide, at preferably 1.25 molar equivalents, dissolved in dimethylformamide, preferably 10 volumes, and di-isoprolyethylamine, preferably 1.25 molar equivalents, is added slowly to the heated diamine with stirring over a period of about 4 hours. Alternatively, the di-isoprolyethylamine may be added to the reaction with the diamine, and the propyl sulfonate or propyl halide may be dissolved in dimethylformamide to form a mixture, which may be added to the reaction with stirring for about 4 hours. The elevated temperature of the reaction may be below the boiling temperature of the reaction, specifically, below the boiling temperature of the organic solvent(s) of the reaction mixture. The elevated temperature may be lower than about 125° C., preferably lower than about 100° C., and more preferably about 65° C. or lower. The times necessary for the reaction may vary with the identities of the reactants, the solvent system and with the chosen temperature.

Embodiments of the process further comprise cooling the reaction to a temperature of about room temperature, about 25° C., and stirring the reaction for about 2 hours. The process may further involve filtering the reaction to isolate a solid precipitate, washing the precipitate with an alcohol, and drying the precipitate under vacuum. The pramipexole salt reaction product of this process may display an increased optical purity over the reactants.

Alternatively, the pramipexole sulfonate or halide salt can be reacted with concentrated HCl in an organic solvent, such as an alcohol, at a temperature of from about 0 to about 5° C. An organic solvent, such as methyl tert-butyl ether (MTBE), may be added, and the reaction may be stirred for an additional hour. The (R)-pramipexole dihydrochloride product may be recovered from the reaction mixture by filtering, washing with an alcohol and vacuum drying.

In an embodiment of the process, referred to as condition A in Table 7 and in the examples, the reaction condition which may be sufficient to generate the pramipexole product may include heating the dissolved diamine of formula II to an elevated temperature with continuous stirring. The elevated temperature is preferably less than the melting point of the chosen organic solvent, lower than about 125° C., preferably lower than about 100° C., and more preferably about 95° C. A solution of propyl sulfonate or propyl halide, which is dissolved in di-isoprolyethylamine and an organic solvent to form a mixture, is added slowly over a period of several hours. This reaction mixture may then be stirred at temperature for an additional period of time such as, for example, about 4 hours. The times necessary for the reaction may vary with the identities of the reactants and solvent system, and with the chosen temperature, and would be understood by one of skill in the art.

In an alternate embodiment, the di-isoprolyethylamine may be added to the reaction with the diamine, and the propyl sulfonate or propyl halide may be dissolved in an organic solvent to form a mixture, which may be added to the reaction with stirring over a period of several hours. This reaction mixture may then be stirred at temperature for an additional period of time such as, for example, at least 4 hours. The time necessary for the reaction to run to completion may vary with the identities of the reactants and solvent system, and with the chosen temperature, and would be understood by one of skill in the art.

In an alternative embodiment of the process, referred to as condition B in Table 7, the reaction conditions which are sufficient to generate the pramipexole product may include using dimethylformamide as the organic solvent, and heating the dissolved diamine of formula II to an elevated temperature with continuous stirring. The elevated temperature is preferably less than the melting point of the chosen organic solvent, lower than about 125° C., preferably lower than about 100° C., and more preferably about 75° C. A solution of propyl sulfonate or propyl halide, which is dissolved in dimethylformamide, may be added slowly over a period of several hours. This reaction mixture may then be stirred at temperature for an additional period of time such as, for example, about 4 hours. The time necessary for the reaction to run to completion may vary with the identities of the reactants and solvent system, and with the chosen temperature, and would be understood by one of skill in the art.

In a preferred alternative embodiment of the process, referred to as condition C in Table 7, the reaction includes using dimethylformamide as the organic solvent for dissolution of the diamine. The diamine of formula II may then be heated to an elevated temperature with continuous stirring. The elevated temperature is preferably less than the melting point of the chosen organic solvent, lower than about 125° C., preferably lower than about 100° C., and more preferably about 65° C. A solution of propyl sulfonate or propyl halide, preferably about 1.25 molar equivalents, may be dissolved in dimethylformamide, preferably about 10 volumes, and di-isoproplyethylamine, preferably about 1.25 molar equivalents, to form a mixture. This mixture may be added slowly over a period of several hours to the heated diamine. This reaction mixture may then be stirred at temperature for an additional period of time such as, for example, about 4 hours. Alternatively, the di-isoproplyethylamine may be added to the reaction with the diamine, and the propyl sulfonate or propyl halide may be dissolved in dimethylformamide to form a mixture, which may be added to the reaction with stirring over a period of several hours. This reaction mixture may then be stirred at temperature for an additional period of time such as, for example, about 4 hours. The time necessary for the reaction to run to completion may vary with the identities of the reactants and solvent system, and with the chosen temperature, and would be understood by one of skill in the art.

Purification of the final pramipexole product may include cooling the reactions disclosed above to a temperature of about 25° C., and stirring the reactions for a period of time such as, for example, about 2 hours. The purification may further include filtering the reaction to isolate a solid precipitate, washing the precipitate with an alcohol, and drying the precipitate under vacuum. The final products of the reaction may be analyzed by high pressure liquid chromatography (HPLC) for chemical and chiral purity.

Further, $^1$H NMR and $^{13}$C NMR may be used to confirm the structure of the product pramipexole. Results of example syntheses using each of the several conditions which are embodiments of the present disclosure are listed in Table 7. Several example syntheses of pramipexole using conditions A and C of the present disclosure are detailed in Examples 5-7.

The sulfonate or halide salts of pramipexole may be converted to an HCl salt using a concentrated solution of HCl in ethanol. A p-TSA pramipexole salt may be re-dissolved in an alcohol, such as ethanol, and the mixture may be cooled to between about 0 and about 5° C. with continuous stirring. A concentrated HCl may then be added, followed by a solvent such as methyl tert-butyl ether (MTBE), and the mixture may be stirred for an hour at between about 0 and about 5° C. The reaction mixture may then be filtered, washed with an MTBE/alcohol solution, and dried under vacuum. The final product is pramipexole dihydrochloride. A detailed example of this synthesis may be found in Example 8.

An alternate method for conversion of the sulfonate or halide salts of pramipexole to an HCl salt involves the use of a concentrated solution of HCl and isopropyl acetate (IPAC). A sulfonate or halide salt of pramipexole may be taken up in IPAC and cooled to 15° C. HCl (gas) may be bubbled into the slurry for about 1 hour, after which the mixture may be filtered, washed with IPAC and dried under vacuum at room temperature to afford a pramipexole dihydrochloride salt. A detailed example of this synthesis may be found in Example 9.

The sulfonate or halide salts of pramipexole may alternatively be converted to the free base form of pramipexole. A p-TSA pramipexole salt may be dissolved in dichloromethane (DCM) and water. The resulting solution may then by brought to a pH of about 11-12 using NaOH. Two phases may be generated, and the aqueous phase may be extracted with DCM, dried over magnesium sulfate (MgSO$_4$), filtered over Celite® and concentrated. The concentrated residue may be re-dissolved in MTBE and stirred as a slurry for several hours. The solids may then be filtered, washed with MTBE, and dried under vacuum at a temperature of about 35° C. The final product is pramipexole free base. A detailed example of this synthesis may be found in Example 10.

Alternatively, the sulfonate or halide salts of pramipexole may alternatively be converted to the free base form of pramipexole by a second process. In this second process, the p-TSA salt of pramipexole is dissolved in water and cooled to a temperature of about 10° C. This slurry is basified by addition of NaOH, diluted with brine, and extracted several times in DCM. The combined organic phases are then washed with brine, dried over MgSO$_4$, filtered and concentrated to dryness. A detailed example of this synthesis may be found in Example 11.

The free base form of pramipexole may be converted to pramipexole dihydrochloride by bubbling HCl gas into a cooled solution of the pramipexole free base in IPAC. Alternatively, the free base form of pramipexole may be converted to pramipexole dihydrochloride by mixing with concentrated HCl at room temperature overnight. Detailed examples of the aforementioned synthesis schemes may be found in Examples 12 and 13, respectively.

Alternatively, the free base form of pramipexole may be converted to pramipexole fumarate by the addition of 2 molar equivalents of fumaric acid.

TABLE 7

Experiments for S$_N$2 preparation of pramipexole pTSA salt

| Condition | Isomer | Batch Size | Results |
|---|---|---|---|
| A | R(+) | 45 grams | Yield = 53.2 grams (52%) Chemical Purity = 98.2% AUC by HPLC Chiral Purity = >99.5% AUC by HPLC |
| A | S(−) | 5 grams | Yield = 4.99 grams (44.2%) Chemical Purity = 98.0% AUC by HPLC Chiral Purity = >99.6% AUC by HPLC |
| A | Racemic | 5 gram | Yield = 5.12 grams (45%) Chemical Purity = 97.1% AUC by HPLC Chiral Purity = 1:1 R(+):S(−) by HPLC |

TABLE 7-continued

Experiments for S_N2 preparation of pramipexole pTSA salt

| Condition | Isomer | Batch Size | Results |
|---|---|---|---|
| B | R(+) | 5 gram | Yield = 4.6 grams (40%)<br>Chemical Purity = 94.9%<br>AUC by HPLC<br>Chiral Purity = 99.6%<br>AUC by HPLC |
| B | S(−) | 10 gram | Yield = 9.81 grams (43.3%)<br>Chemical Purity = 94.9%<br>AUC by HPLC<br>Chiral Purity = 99.7%<br>AUC by HPLC |
| B | Racemic | 5 gram | Yield = 2.9 grams (25.6%)<br>Chemical Purity = 98.3%<br>AUC by HPLC<br>Chiral Purity = 1:1<br>R(+):S(−) by HPLC |
| C | R(+) | 250 gram | Yield = 317.6 grams (56%)<br>Chemical Purity = 99.4%<br>AUC by HPLC<br>Chiral Purity = 99.8%<br>AUC by HPLC |
| C | S(−) | 20 gram | Yield = 25.41 grams (56%)<br>Chemical Purity = 99.4%<br>AUC by HPLC<br>Chiral Purity = 99.7%<br>AUC by HPLC |
| C | Racemic | 5 gram | Yield = 6.02 grams (53.1%)<br>Chemical Purity = 99.2%<br>AUC by HPLC<br>Chiral Purity = 1:1<br>R(+):S(−) by HPLC |
| E* | R(+) | 25 gram | Yield = 47%<br>Chiral Purity = 99.8%<br>AUC by HPLC |
| E* | S(−) | 25 gram | Yield = 47%<br>Chiral Purity = 99.8%<br>AUC by HPLC |

*Condition E is the same as Condition C, except that the recovery step does not incorporate dilution in MTBE. The MTBE increases the recovery (yield) from the synthesis reaction, but may reduce the overall chiral purity. Condition E is explained in more detail in Table 9.

The alternative process for preparing an enantiomerically pure pramipexole from a mixture of (R)-pramipexole and (S)-pramipexole involves using acid addition and trituration (precipitation) of an enantiomerically pure pramipexole based on insolubility of the enantiomers (R(+) and S(−)) in the resulting achiral salt solution. In embodiments of this process, enantiomerically pure pramipexole is triturated from an acid addition solution based on the insolubility of the enantiomers in the resulting achiral salt reagents. This embodiment, a process for preparing an enantiomerically pure pramipexole, comprises dissolving an enantiomerically enriched pramipexole in an organic solvent at an elevated temperature, adding a selected acid, cooling the reaction to room temperature, stirring the cooled reaction at room temperature for an extended time and recovering enantiomerically pure (R)-pramipexole. In a preferred embodiment, the selected acid may be added at from about 1 molar equivalent to about 2 molar equivalents of the enantiomerically enriched pramipexole.

In an embodiment of the process, the selected acid is p-toluenesulfonic acid (p-TSA) and the organic solvent is ethanol. In another embodiment of the process, the elevated temperature may be from about 65° C. to about 85° C. and the cooling occurs at a rate of about 25° C. per hour. The elevated temperature may also be a temperature lower than 125° C., preferably lower than 100° C., and more preferably about 75° C. The times necessary for the reaction may vary with the identities of the reactants, the solvent system and with the chosen temperature, and may be easily appreciated by one of skill in the art. In yet another embodiment of the process, recovering enantiomerically pure pramipexole comprises cooling the reaction to a temperature of about 25° C. and stirring the reaction for at least about 2 hours. The recovery may further comprise filtering the reaction to isolate a solid precipitate, washing the precipitate with an alcohol and drying the precipitate under vacuum.

In various embodiments of the process, the organic solvent may include, but is not limited to, acetonitrile, acetone, ethanol, ethyl acetate, methyl tert-butyl ether, methyl ethyl ketone, isopropyl acetate and isopropyl alcohol. In a preferred embodiment, the organic solvent is ethanol. The acid may include, but is not limited to, halogenic acids such as, for example, hydrobromic, hydrochloric, hydrofluoric and hydroiodic acid; inorganic acids such as, for example, nitric, perchloric, sulfuric and phosphoric acid; organic acids such as, for example, sulfonic acids (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid; and aminoacids such as aspartic or glutamic acid. The acid may be a mono- or di-acid, such as a di-hydrohalogenic, di-sulfuric, di-phosphoric or di-organic acid. In all cases, the acid is used as an achiral reagent which is not selected on the basis of any expected or known preference for interaction with or precipitation of a specific optical isomer of the products of this disclosure. In a preferred embodiment, the selected acid is p-toluenesulfonic acid.

In embodiments of the process, the final chiral purity for an R(+) enantiomer of the pramipexole salt may be greater than 99% when the starting mixture contains pramipexole which is at least 55% optically pure for the R(+) enantiomer, preferably 80% optically pure for the R(+) enantiomer, preferably 85% optically pure for the R(+) enantiomer, more preferably 90% optically pure for the R(+) enantiomer and most preferably 95% optically pure for the R(+) enantiomer. The final chiral purity for an S(−) enantiomer of the pramipexole salt may be greater than 99% when the starting mixture contains pramipexole which is at least 55% optically pure for the S(−) enantiomer, preferably 80% optically pure for the S(−) enantiomer, preferably 85% optically pure for the S(−) enantiomer, more preferably 90% optically pure for the S(−) enantiomer and most preferably 95% optically pure for the S(−) enantiomer. The chiral purity of the final pramipexole salt may preferably be 99.6% or greater, 99.7% or greater, preferably 99.8% or greater, and more preferably 99.9% or greater. In some embodiments, the chiral purity of the final pramipexole salt may be 100%.

In embodiments, after the enantiomerically enriched pramipexole is dissolved in an organic solvent at an elevated temperature and the acid is added, the reaction may be cooled to room temperature at a rate of about 25° C./hour. The enantiomerically pure pramipexole may then be recovered from the reaction solution by stirring the reaction for at least about 2 hours, filtering the reaction to isolate a solid precipitate, washing the precipitate with an alcohol and drying the precipitate under vacuum. The rates of cooling and the time required for the additional stirring may vary with the chosen organic solvent and acid, and may be easily appreciated by one skilled in the art. Additionally, the reaction volumes may dictate the degree of optical purification and the overall yield of the final pramipexole product. These volumes would be understood and appreciated by one of skill in the art. Examples of specific times, temperatures and volumes which enable the practice of this invention are given in the Examples.

In embodiments, the chiral purity of the pramipexole salt product for the R(+) enantiomer may be greater than 99% when the chiral purity of the starting pramipexole mixture for the R(+) enantiomer is greater than 55%, preferably greater than 70%, or more preferably greater than 90%. The chiral purity of the final pramipexole salt may be 99.6% or greater, 99.7% or greater, preferably 99.8% or greater, and more preferably 99.9% or greater, more preferably 99.95% or greater, even more preferably 99.99% or greater. In some embodiments, the chiral purity of the final pramipexole salt may be 100%.

Chirally pure pramipexole also may be prepared by the process of trituration of a single enantiomer of pramipexole from a mixture of R(+) and (S)-pramipexole by acid addition, based on insolubility of the enantiomers in the resulting achiral salt solution. The process comprises dissolving an enantiomerically enriched pramipexole in an organic solvent at an elevated temperature, adding from about 1.05 molar equivalents to about 2.05 molar equivalents of a selected acid, cooling the reaction to room temperature, stirring the cooled reaction at room temperature for an extended time and recovering enantiomerically pure pramipexole.

In embodiments, the elevated temperature of the reaction may be below the boiling temperature of the reaction, specifically, below the boiling temperature of the organic solvent(s) of the reaction mixture. The elevated temperature may be lower than about 125° C., more preferably lower than about 100° C., and more preferably about 75° C. The times necessary for the reaction may vary with the identities of the reactants, the solvent system and with the chosen temperature, and would be appreciated by one of skill in the art.

In embodiments, the organic solvent may include, but is not limited to, acetonitrile, acetone, ethanol, ethyl acetate, methyl tert-butyl ether, methyl ethyl ketone, isopropyl acetate and isopropyl alcohol. In a preferred embodiment, the organic solvent is ethanol. In this embodiment, the acid may include, but is not limited to, halogenic acids such as, for example, hydrobromic, hydrochloric, hydrofluoric and hydroiodic acid; inorganic acids such as, for example, nitric, perchloric, sulfuric and phosphoric acid; organic acids such as, for example, sulfonic acids (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid; and aminoacids such as aspartic or glutamic acid. The acid may be a mono- or di-acid, such as a di-hydrohalogenic, di-sulfuric, di-phosphoric or di-organic acid. In all cases, the acid is used as an achiral reagent which is not selected on the basis of any expected or known preference for interaction with or precipitation of a specific optical isomer of the products of this disclosure. In a preferred embodiment, the selected acid is p-toluenesulfonic acid.

In additional embodiments, after the enantiomerically enriched pramipexole is dissolved in an organic solvent at an elevated temperature and the acid is added, the reaction may be cooled to room temperature at a rate of about 25° C./hour. The chirally pure pramipexole may then be recovered from the reaction solution by stirring the reaction for at least about 2 hours, filtering the reaction to isolate a solid precipitate, washing the precipitate with an alcohol and drying the precipitate under vacuum. The rates of cooling and the time required for the additional stirring may vary with the chosen organic solvent and acid, and would be appreciated by one skilled in the art. Additionally, the reaction volumes may dictate the degree of optical purification and the overall yield of the final pramipexole product. These volumes would be understood and appreciated by one of skill in the art. Examples of specific times, temperatures and volumes which enable the practice of this invention are given in the Examples.

In embodiments, the chiral purity for the R(+) enantiomer of the recovered pramipexole salt may be greater than 99% when the starting pramipexole material has a chiral purity for the R(+) enantiomer of greater than 55%, preferably greater than 70%, or more preferably greater than 90%. The chiral purity of the final pramipexole salt for the R(+) enantiomer may be 99.6% or greater, 99.7% or greater, preferably 99.8% or greater, and more preferably 99.9% or greater, more preferably 99.95% or greater, even more preferably 99.99% or greater. In a most preferred embodiment, the chiral purity of the final pramipexole salt for the R(+) enantiomer may be 100%.

The process may include dissolving an enantiomerically enriched pramipexole in an organic solvent at an elevated temperature, adding from about 1.05 equivalents to about 2.05 equivalents of a selected acid, cooling the reaction to room temperature, stirring the cooled reaction at room temperature for an extended period of time and recovering enantiomerically pure pramipexole of formula I.

In an embodiment of the process, the selected acid is p-toluenesulfonic acid (p-TSA) and the organic solvent is ethanol. In another embodiment of the process, the elevated temperature may be from about 65° C. to about 85° C. and the cooling occurs at a rate of about 25° C. per hour. The elevated temperature may also be a temperature lower than 125° C., preferably lower than 100° C., and more preferably about 75° C. The times necessary for the reaction may vary with the identities of the reactants, the solvent system and with the chosen temperature, and may be easily appreciated by one of skill in the art. In yet another embodiment of the process, recovering enantiomerically pure pramipexole comprises cooling the reaction to a temperature of about 25° C. and stirring the reaction for at least about 2 hours. The recovery may further comprise filtering the reaction to isolate a solid precipitate, washing the precipitate with an alcohol and drying the precipitate under vacuum.

In various embodiments of the process, the organic solvent may include, but is not limited to, acetonitrile, acetone, ethanol, ethyl acetate, methyl tert-butyl ether, methyl ethyl ketone, isopropyl acetate and isopropyl alcohol. In a preferred embodiment, the organic solvent is ethanol. The acid may include, but is not limited to, halogenic acids such as, for example, hydrobromic, hydrochloric, hydrofluoric and hydroiodic acid; inorganic acids such as, for example, nitric, perchloric, sulfuric and phosphoric acid; organic acids such as, for example, sulfonic acids (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid; and aminoacids such as aspartic or glutamic acid. The acid may be a mono- or di-acid, such as a di-hydrohalogenic, di-sulfuric, di-phosphoric or di-organic acid. In all cases, the acid is used as an achiral reagent which is not selected on the basis of any expected or known preference for interaction with or precipitation of a specific optical isomer of the products of this disclosure. In a preferred embodiment, the selected acid is p-toluenesulfonic acid.

In embodiments of the process, the final chiral purity for an R(+) enantiomer of the pramipexole salt may be greater than 99% when the starting mixture contains pramipexole which is at least 55% optically pure for the R(+) enantiomer, preferably 80% optically pure for the R(+) enantiomer, preferably 85% optically pure for the R(+) enantiomer, more preferably 90% optically pure for the R(+) enantiomer and most preferably 95% optically pure for the R(+) enantiomer. The final chiral purity for an S(−) enantiomer of the pramipexole salt may be greater than 99% when the starting mixture contains pramipexole which is at least 55% optically pure for the S(−) enantiomer, preferably 80% optically pure for the S(−) enantiomer, preferably 85% optically pure for the S(−) enantiomer, more preferably 90% optically pure for the S(−) enantiomer and most preferably 95% optically pure for the S(−) enantiomer. The chiral purity of the final pramipexole salt may preferably be 99.6% or greater, 99.7% or greater, preferably 99.8% or greater, and more preferably 99.9% or greater. In a more preferred embodiment, the chiral purity of the final pramipexole salt may be 100%.

Results of example purifications using each of the several conditions which are embodiments of the present disclosure are listed in Table 8.

TABLE 8

Experiments for preparation of the R(+) enantiomer of pramipexole

| Acid | Solvent | Batch Size | Results |
|---|---|---|---|
| p-TSA | ethanol | 298.7 mg | Yield = 489.5 mg (90.3%)<br>Start Chiral Purity =<br>91% AUC R(+) by HPLC<br>Final Chiral Purity =<br>100% AUC by HPLC |
| MSA | acetonitrile | 300.0 mg | Yield = 431.8 mg (98.9%)<br>Start Chiral Purity =<br>91% AUC R(+) by HPLC<br>Final Chiral Purity =<br>99.23% AUC by HPLC |
| fumaric (hot ethanol) | acetonitrile | 301.0 mg | Yield = 532 mg (84.2%)<br>Start Chiral Purity =<br>91% AUC R(+) by HPLC<br>Final Chiral Purity =<br>99.26% AUC by HPLC |
| phosphoric | acetonitrile | 299.4 mg | Yield = 592 mg (~100%)<br>Start Chiral Purity =<br>91% AUC R(+) by HPLC<br>Final Chiral Purity =<br>100% AUC by HPLC |

The chemical and chiral purity of the preparations of (R)-pramipexole may be verified with at least HPLC, $^{13}$C-NMR, $^1$H-NMR and FTIR. In preferred embodiments, the (R)-pramipexole may be synthesized by the method described above, which yields enantiomerically pure material. Alternatively, the (R)-pramipexole may be purified from mixtures of R(+) and (S)-pramipexole using a purification scheme which is disclosed in U.S. Provisional Application No. 60/894,829 entitled "Methods of Synthesizing and Purifying R(+) and (S)-pramipexole", filed on Mar. 14, 2007, and U.S. Provisional Application No. 60/894,814 entitled "Methods of Enantiomerically Purifying Chiral Compounds", filed on Mar. 14, 2007, which are incorporated herein by reference in their entireties.

By way of explanation, and not wishing to be bound by theory, the solubility of (R)-pramipexole and (S)-pramipexole may be the same in the trituration step of the synthesis and purification processes. As example, if a synthesis process is carried out with 90 grams of the R(+) diamine and 10 grams of the S(−)diamine, and the solubility of the final pramipexole product is 10 grams for either enantiomer, then 80 grams of the (R)-pramipexole product and 0 grams of the (S)-pramipexole product would precipitate (assuming a 100% chemical conversion from the diamine and no change in molecular weight in going to the pramipexole product). That is, 10 grams of each enantiomer of pramipexole may be expected to go into solution. This would lead to a pramipexole product with a 100% chiral purity for the R(+) enantiomer. The opposite ratio of starting materials for the synthesis process (90 grams of the S(−) diamine and 10 grams of the R(+) diamine) may generate a reaction product of 90 grams of the (S)-pramipexole and 10 grams of the (R)-pramipexole. From this reaction product mixture, 80 grams of the S(−) enantiomer and 0 grams of the R(+) enantiomer of pramipexole would be expected to precipitate, leading to a pramipexole product with a 100% chiral purity for the S(−) enantiomer. In this thought experiment, one can imagine that the volumes which are used for a reaction may have a large potential effect on the final yield and chiral purity. That is, too large a volume will reduce the yield as more of the pramipexole enantiomer products will go into solution (but increase the chiral purity) and too small a volume will increase the yield as less of the pramipexole products will go into solution (but reduce the chiral purity).

To better define the actual limits of the reaction volumes and optical purities attainable using methods of the disclosure, various ratios of chiral purity for the starting diamine material were tested. As shown in Table 9, the synthesis and purification process was tested using the following ratios of the starting R(+) and S(−) diamine: 80:20, 20:80, 85:15, 15:85, 90:10, 10:90, 95:5 and 5:95. Additionally, three specific reaction conditions were tested which varied either the reaction volume or a post reaction recovery step. These trials demonstrated that the enantiomers of pramipexole are equally insoluble (or soluble) in the organic solvents utilized in the various embodiments of the synthesis processes disclosed herein.

TABLE 9

Experiments for S$_N$2 preparation of pure enantiomers of pramipexole

| Ratio of starting diamines R(+):S(−) | Condition C (yield/chiral purity) | Condition D (yield/chiral purity) | Condition E (yield/chiral purity) |
|---|---|---|---|
| 80:20 | — | 29%/99% | 34%/98.2% |
| 20:80 | — | 30%/99.4% | 35%/95.7% |
| 85:15 | 43%/86.8% | 36%/99.8% | 39%/99.9% |
| 15:85 | 52%/88.9% | 27%/99.6% | 37%/99.9% |
| 90:10 | 47%/95.9% | — | — |
| 10:90 | 58%/93.6% | — | — |
| 95:5 | 50%/99.6% | — | — |
| 5:95 | 47%/99.6% | — | — |

Condition C: The reaction is performed in 10 volumes of DMF and 1.25 equivalents of propyl tosylate at 65-67° C. The reaction is then cooled to room temperature and diluted with 8 volumes of MTBE.
Condition D: The reaction is performed in 18 volumes of DMF and 1.25 equivalents of propyl tosylate at 65-67° C. The reaction is then cooled to room temperature and diluted with 8 volumes of MTBE.
Condition E: The reaction is performed in 10 volumes of DMF and 1.25 equivalents of propyl tosylate at 65-67° C. The reaction is then cooled to room temperature with no dilution in MTBE.

The data in Table 9 demonstrate that both enantiomers of pramipexole have similar, if not the same, solubility. Further, the data show that the synthesis is equally efficient for either enantiomer of pramipexole. These data also demonstrate that the enantiomers behave independently of one another, in that the solubility of one enantiomer appears to be unaffected by the concentration in solution of the other. For example, the various synthesis reactions carried out using condition C all have chemical yields of about 50%, independent of the percentage of predominant diamine enantiomer of the starting material. When the volume of the organic solvent used in the synthesis reaction is increased, the chemical yield is reduced, but the chiral yield is increased. This is apparent by comparison of the reaction carried out in conditions C and D, where an 85:15 ratio of R(+):S(−) diamine produced a pramipexole product having an 86.8% chiral purity for the R(+) enantiomer when the reaction used 10 volumes of the organic solvent and a 99.8% chiral purity for the R(+) enantiomer when the reaction used 18 volumes of the organic solvent. Note also that the chemical yield was reduced in the reaction using a larger volume of organic solvent (43% yield in condition C and 36% yield in condition D).

In Table 9, condition E is the same as condition C, except that the recovery step does not incorporate dilution in MTBE. The MTBE is observed to increase pramipexole recovery (yield) from the synthesis reaction, but may reduce the overall chiral purity. This is born out by a comparison of the results for trials carried out in an 85:15 ratio of R(+):S(−) diamine, which produced a pramipexole product having a 86.8% chiral purity for the R(+) enantiomer when the reaction included the MTBE organic solvent and a 99.9% chiral purity for the R(+) enantiomer when the reaction did not include the MTBE organic solvent. The chemical yield was reduced by exclusion of the MTBE dilution in the recovery step; a 43% yield in condition C as opposed to a 39% yield in condition E.

The chirally pure (R)-pramipexole prepared by any of the above methods may be converted to a pharmaceutically acceptable salt of (R)-pramipexole. For example, (R)-pramipexole dihydrochloride is a preferred pharmaceutical salt due its high water solubility. (R)-pramipexole dihydrochloride may be prepared from other salts of (R)-pramipexole in a one step method comprising reacting the (R)-pramipexole, or (R)-pramipexole salt, with concentrated HCl in an organic solvent, such as an alcohol, at a reduced temperature. In some embodiments, the reduced temperature is a temperature of from about 0° C. to about 5° C. An organic solvent, such as methyl tert-butyl ether, may be added, and the reaction may be stirred for an additional hour. The (R)-pramipexole dihydrochloride product may be recovered from the reaction mixture by filtering, washing with an alcohol and vacuum drying.

Each of the methods disclosed herein for the manufacture and purification of (R)-pramipexole or a pharmaceutically acceptable salt thereof may be scalable to provide industrial scale quantities and yields, supplying products with both high chemical and chiral purity. In some embodiments, the enantiomerically pure (R)-pramipexole may be manufactured in large batch quantities as may be required to meet the needs of a large scale pharmaceutical use.

Various aspects of the present invention will be illustrated with reference to the following non-limiting examples.

EXAMPLES

Example 1

Measurement of the dopamine receptor affinities for the R(+) and S(−) enantiomers of pramipexole.

The S(−) enantiomer of pramipexole has historically been characterized as a high affinity dopamine receptor ligand at the $D_2$ (both the S and L isoforms), $D_3$ and $D_4$ receptors, although the highest affinity is seen for the $D_3$ receptor subtype. The dopamine receptor ligand affinity of (S)-pramipexole and of (R)-pramipexole from journal publications has been tabulated (data are reproduced in Table 10). Although the conditions under which each study or experiment was carried out are slightly different, and different radio-ligands were used, the data show comparable affinities for the various dopamine receptors. Studies we conducted on the dopamine receptor affinities of the S(−) and the R(+) enantiomers of pramipexole are also shown in Table 10. These data demonstrate an unexpectedly large difference in the affinities of the two enantiomers of pramipexole for all dopamine receptors. Table 10 shows that; instead of the expected 10-20 fold difference in binding affinity for D2 receptor affinity, and 50-fold difference in binding affinity for D3 receptor affinity as derived from the literature, the values we found were typically 10-fold higher (290- and 649-fold, respectively) (Table 10).

TABLE 10

Comparative binding affinity data for pramipexole enantiomers

| Receptor | Source | S(−) | R(+) | Ratio S:R |
|---|---|---|---|---|
| $D_2$ binding, $IC_{50}$ (nM) | Lit.* | 4,700 | 43,000 | 9 |
| $D_2$ binding, $IC_{50}$ (nM) | Lit.** | 402 | 8,330 | 21 |
| $D_2$ binding, $IC_{50}$ (nM) | Actual*** | 6.2 | 1,800 | 290 |
| $D_3$ binding, $IC_{50}$ (nM) | Lit.** | 4.2 | 211 | 50 |
| $D_3$ binding, $IC_{50}$ (nM) | Actual*** | 0.94 | 610 | 649 |

*Schneider, C. S.; Mierau, J., "Dopamine Autoreceptor Agonists: Resolution and Pharmacological Activity of 2,6-Diaminotetrahydrobenzothiazole and an Aminothiazole Analogue of Apomorphine", (1987). *J. Med. Chem.* 30: 494-498
**Wong, S. K.-F.; Shrikhande, A. V., S. K.-F. Wong, "Activation of Extracellular Signal-Regulated Kinase by Dopamine D2 and D3 Receptors",. (2003) *Society for Neuroscience Abstracts*
***Data from current study The (R)-pramipexole and (S)-pramipexole were supplied as dry powder to our contract research partner Cerep by the manufacturer AMRI. Solutions of (R)-pramipexole and (S)-pramipexole were prepared from stock solutions in DMSO. Eight concentrations of (R)-pramipexole or (S)-pramipexole (0.01 nM, 0.1 nM, 1 nM, 10 nM, 100 nM, 1 mM, 10 mM and 100 mM) were used to displace standard reference radiolabeled dopamine agonists. These concentrations were tested in cell lines expressing select human cloned dopamine receptors ($D_{2S}$, $D_3$). Previous work in the literature and our data demonstrated no significant interaction with D1 and D5 dopamine receptors. Group results for the interaction of (R)-pramipexole or (S)-pramipexole with each receptor are expressed as the IC50 in Table 10.

These data indicate that $IC_{50}$ values of (R)-pramipexole at these receptors are approximately 290 to 649 times that of the $IC_{50}$ values for (S)-pramipexole. Further, these data suggest that the ratio of the $IC_{50}$ values for (R)-pramipexole to (S)-pramipexole at the $D_2$ receptor are approximately 14 to 32 times larger than the ratios suggested by the literature, at least when the chiral purities were beyond the limits of detection (LOD 0.05%) (chiral purity greater than 99.95%). Similarly, the data suggest that the ratio of the $IC_{50}$ values for (R)-pramipexole to (S)-pramipexole at the $D_3$ receptor are approximately 13 times larger than the ratios suggested by the literature, at least when the chiral purities were beyond the limits of detection (chiral purity greater than 99.95%). These data also suggest that if dopamine receptor affinity is the major contributing factor to limiting dose tolerance of the S(−) enantiomer, then pure preparations of the R(+) enantiomer should have a maximum tolerated dose (MTD) and/or a no observable adverse effect level dose (NOAEL) of at least 290 times greater than the S(−) enantiomer's MTD and/or NOAEL. Thus, even a small contamination of the (R)-pramipexole compositions of the present invention by the S(−) enantiomer, at levels as low as 0.5% or less, may effect the observed MTD and NOEL.

Example 2

In vivo studies to determine the MTD and NOAEL in dogs for 100% pure preparations of the R(+) and S(−) enantiomers of pramipexole, and a mixture (R 99.5%/S 0.5%). The form of (R)-pramipexole was (R)-pramipexole dihydrochloride monohydrate.

The following in vivo study in beagle dogs was undertaken to test the hypothesis that the large observed difference in receptor binding affinities for the R(+) and S(−) enantiomers of pramipexole will translate to a large observed difference in the observed maximum tolerated dose (MTD) and/or no observable adverse effect level (NOAEL) of the two enantiomers. Dogs were administered preparations of each enantiomer prepared as a highly purified compound (100% pure preparations (within the limits of analytical detectability)), or a preparation of the R(+) enantiomer contaminated by 0.5% of the S(−) enantiomer of pramipexole.

Three groups of four non-naïve male beagle dogs were used in the study. Each group was administered various doses of either the R(+) or S(−) enantiomer prepared as a highly purified compound, or a preparation of the R(+) enantiomer contaminated by 0.5% of the S(−) enantiomer of pramipexole. Doses were administered orally by gavage and clinical observations were taken continuously following dosing: hourly for the first four hours, and then twice daily cage-side observations for the duration of the inter-dose or post-dose interval. Observations were made of clinical signs, mortality, injury and availability of food and water. Animals were fasted for 24 hr prior to dosing. Dogs in each group were exposed to only one drug, or the combination; each dose was administered only once, with a subsequent dose administered after a recovery period of 4 days. The data are summarized in Table 11.

A NOAEL was established at a dose level of 25 mg/kg for the R(+) enantiomer when administered to non-naïve dogs, while a dose level of 75 mg/kg may be considered an MTD in non-naïve dogs. For the S(−) enantiomer, a NOAEL of 0.00125 mg/kg and an MTD of 0.0075 mg/kg was found in non-naïve dogs. For the composition containing a mixture of the two enantiomers (99.5% (R)-pramipexole and 0.5% (S)-pramipexole), the NOAEL was found to be 0.25 mg/kg, which corresponds to a dose of 00125 mg/kg of the S(−) enantiomer, while the MTD is 1.5 mg/kg, which corresponds to a dose of 0.0075 mg/kg of the S(−) enantiomer. These data indicate that the NOAEL for the R(+) enantiomer of pramipexole is approximately 20,000-fold greater than for the S(−) enantiomer in non-naïve dogs, while the MTD is about 10,000-fold greater.

TABLE 11

Clinical observations in male beagle dogs for administration of pramipexole compositions
SUMMARY OF CLINICAL FINDINGS*

| | Dose Amount (mg/kg) | | | | | | | | |
|---|---|---|---|---|---|---|---|---|---|
| | 7.5 R(+) (Day 1) | 25 R(+) (Day 4) | 75 R(+) (Day 8) | 0.0075 S(−) (Day 1) | 0.025 S(−) (Day 4) | 0.00125 S(−) Day 8) | 1.5 mixture** (Day 1) | 5 mixture (Day 4) | 0.25 mixture (Day 8) |
| Behavior/Activity | | | | | | | | | |
| Activity decreased | 0/4 | 0/4 | 2/4 | 3/4 | 4/4 | 0/4 | 4/4 | 4/4 | 0/4 |
| Convulsions - clonic | 0/4 | 0/4 | 1/4 | 0/4 | 0/4 | 0/4 | 0/4 | 0/4 | 0/4 |
| Salivation | 0/4 | 0/4 | 3/4 | 0/4 | 0/4 | 0/4 | 0/4 | 0/4 | 0/4 |
| Tremors | 0/4 | 0/4 | 4/4 | 1/4 | 3/4 | 0/4 | 1/4 | 2/4 | 0/4 |
| Excretion | | | | | | | | | |
| Emesis | 0/4 | 0/4 | 2/4 | 3/4 | 4/4 | 0/4 | 1/4 | 3/4 | 1/4 |
| Feces hard | 1/4 | 0/4 | 0/4 | 1/4 | 0/4 | 0/4 | 0/4 | 0/4 | 0/4 |
| Feces mucoid | 0/4 | 0/4 | 0/4 | 0/4 | 0/4 | 0/4 | 1/4 | 1/4 | 0/4 |
| Feces soft | 0/4 | 0/4 | 1/4 | 0/4 | 0/4 | 0/4 | 2/4 | 1/4 | 1/4 |
| Feces watery | 0/4 | 0/4 | 0/4 | 0/4 | 0/4 | 0/4 | 1/4 | 1/4 | 0/4 |
| External Appearance | | | | | | | | | |
| Lacrimation | 0/4 | 0/4 | 0/4 | 0/4 | 0/4 | 0/4 | 0/4 | 0/4 | 0/4 |
| Eye/Ocular | | | | | | | | | |
| Pupils dilated | 0/4 | 0/4 | 2/4 | 0/4 | 0/4 | 0/4 | 0/4 | 0/4 | 0/4 |
| Pelage/Skin | | | | | | | | | |
| Skin warm to touch | 1/4 | 0/4 | 1/4 | 0/4 | 0/4 | 0/4 | 0/4 | 0/4 | 0/4 |

*Number of animals affected/Total number of animals
**Mixture of 99.5% (R)-pramipexole and 0.5% (S)-pramipexole.

The data shown in Table 11 indicate that the receptor affinities identified (see Table 10) contribute in a straightforward fashion to the observed differences in the MTD and NOAEL doses for the R(+) and S(−) enantiomers of pramipexole. These data also indicate that the chiral purity for the R(+) enantiomer of pramipexole in embodiments of the compositions of the present invention (refer to Tables 5 and 6) may need to be in excess of 99.9%, depending on the final total dose, to avoid the adverse side effects of (S)-pramipexole.

Further, the data in Table 11 demonstrate that the NOAEL and MTD for the combination composition (99.5% (R)-pramipexole and 0.5% (S)-pramipexole) may be determined directly by the dose of the S(−) enantiomer in the composition. Thus, a small (fractional percentage) contamination of a composition of (R)-pramipexole by the S(−) enantiomer may reduce the MTD and NOEL of the composition. For example, in these experiments, the MTD of pramipexole was reduced from 75 mg/kg for the R(+) enantiomer to a total dose of 1.5 mg/kg of the mixed composition (a factor of 50), and the NOAEL was reduced from 25 mg/kg to 0.25 mg/kg, respectively (a factor of 100). Since the shift in MTD and NOAEL may be predicted by the dose of the S(−) enantiomer of pramipexole in the mixture, the shift for any unknown mixture may be calculated based on the percentage contamination of the (R)-pramipexole by the S(−) enantiomer, relative to the MTD and NOAEL for (S)-pramipexole. This indicates that any contamination of an (R)-pramipexole dosing solution with (S)-pramipexole will have a measurable effect on these indicators of dose tolerability.

Example 3.1—Toxicology Studies in Rats and Minipigs and Phase I Studies in Healthy Adult Volunteers Two-week and three-month toxicology studies of (R)-pramipexole in rats and minipigs were completed. NOAEL dose levels of 150 mg/kg at two-weeks and 100 mg/kg at three-months for rats and 75 mg/kg at two-weeks and 50 mg/kg at three-months for minipigs were established. Phase I studies of healthy adult volunteers have demonstrated that (R)-pramipexole in ascending single doses up to 300 mg and multiple doses up to 200 mg per day for 4½ days is safe and well-tolerated. The Mirapex® label specifies a starting dose of 0.125 mg and a maximum total daily dose of 4.5 mg. The Phase I data demonstrate, therefore, that (R)-pramipexole may be safely administered (1) at starting doses that are at least 2400-fold higher than the Mirapex® starting dose and (2) at steady state doses that are at least 44-fold higher than the highest recommended dose of Mirapex®. The form of (R)-pramipexole was (R)-pramipexole dihydrochloride monohydrate.

The preliminary results of the clinical studies and the toxicology studies are discussed. Exposure at steady state in rats, minipigs, and humans is linear across all doses studied. After 3 months of dosing, the current No Observed Adverse Effect Level (NOAEL) in rats has been determined to be 100 mg/kg; and the current NOAEL in minipigs has been determined to be 50 mg/kg. The mean steady state AUC in rats at the NOAEL dose of 100 mg/kg was 61,299 and 61,484 h*ng/mL for males and females, respectively, and for minipigs at the NOAEL dose of 50 mg/kg was 91,812 and 131,731 h*ng/mL for males and females, respectively. The mean steady state AUC in humans at a dose of 100 mg Q12H (200 mg total daily dose) was 2,574 h*ng/mL. The drug has been safe, well-tolerated, and free of clinically significant adverse events in healthy adult subjects at single doses up to 300 mg and at multiple doses up to 100 mg Q12H, and the projected human exposure associated with a daily dose of 250 mg Q12H is expected to be greater than 13-fold lower than exposures seen at the NOAEL in male minipigs and approximately 9-fold lower than exposures seen at the NOAEL in male and female rats after 13 weeks of dosing.

3.2—Clinical Studies (R)-pramipexole has been studied at single daily doses of 50, 150 and 300 mg and twice daily doses of 50 and 100 mg for 4½ days in healthy adult volunteers. The drug has been safe and well-tolerated in both studies and there were no serious adverse events, discontinuations due to adverse events, or dose-related or clinically significant adverse events in either study. The most frequent adverse events have been dizziness and headache, all of which have been mild to moderate in severity and resolved without intervention.

3.2.1—Summary of (Blinded) Safety and Pharmacokinetic Results of (R)-Pramipexole (Ascending Single-Dose Study)

Three sequential panels of 8 subjects each received single doses of (R)-pramipexole (6 subjects) or placebo (2 subjects) at ascending dose levels of 50, 150, and 300 mg. Safety observations included vital signs, physical examination, clinical laboratory tests, ECGs, and adverse event reporting. Blood and urine samples were collected pre-dose and for 72 hours post-dose to assess the pharmacokinetics. All 24 subjects completed the study as planned. There were no serious adverse events; 46% of all subjects reported at least one non-serious adverse event (AE). Most AEs were mild; the most frequent AE was mild dizziness in 21% of subjects. There were no clinically significant safety observations at any dose level.

Figure 2:
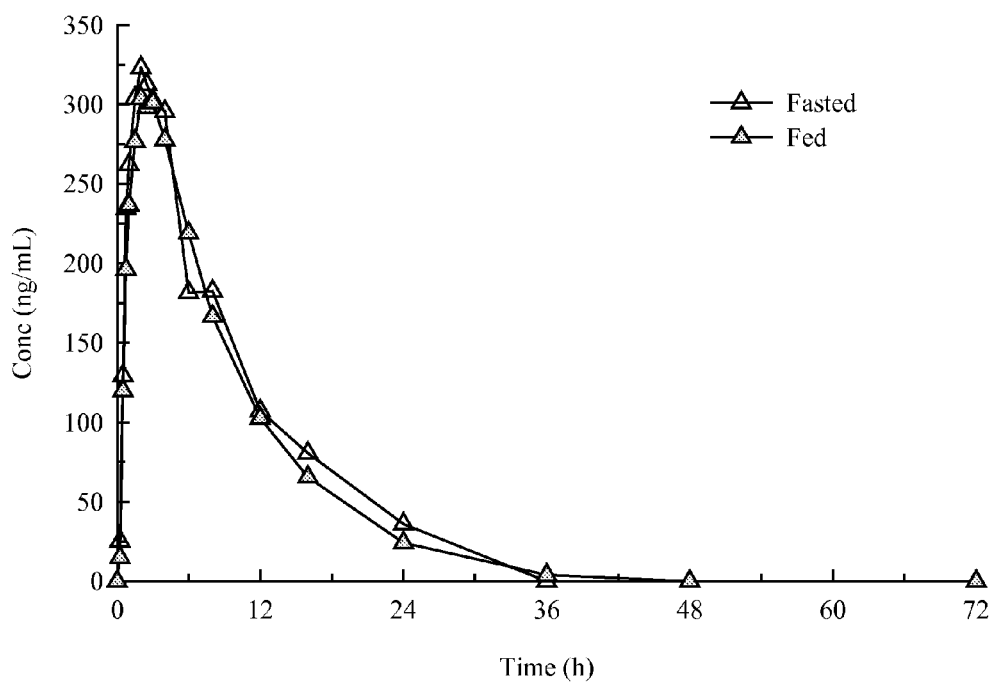
FIG. 2 depicts mean plasma (R)-pramipexole concentrations after oral administration of single 150 mg doses to healthy volunteers under fasted and fed conditions.

Pharmacokinetic data indicated that (R)-pramipexole is rapidly absorbed with mean maximum concentrations of 125, 360, and 781 ng/mL reached at approximately 2 hours post-dose for the 50, 150, and 300 mg dose groups, respectively (see FIG. 1 and Table 12, below). Mean exposures ($AUC_{0-\infty}$) were 1254, 3815, and 8623 h*ng/mL for the 50, 150, and 300 mg dose groups, respectively. Both $C_{max}$ and AUC increased in proportion to dose across the dose levels tested. Urinary excretion of unchanged drug accounted for approximately 70% of drug elimination across dose levels. The mean $T_{1/2}$ was 6-7 hours and was independent of dose. Comparison of the mean plasma concentrations (FIG. 2) and mean pharmacokinetic parameters (Table 12) after administration of a single 150 mg following a high fat/high calorie breakfast with those after administration of 150 mg under fasted conditions demonstrates essentially no effect of a meal on the absorption and elimination of (R)-pramipexole.

Results of this study demonstrate that single oral doses of 50, 150, and 300 mg (R)-pramipexole are safe and well-tolerated. The drug is orally bioavailable and the pharmacokinetics are linear. Absorption and elimination are not affected by a high fat/high calorie meal.

TABLE 12

Summary of pharmacokinetic parameters for (R)-pramipexole after oral administration of single 50 mg, 150 mg, and 300 mg doses to healthy volunteers under fasted conditions and 150 mg under fed conditions.

| Parameter[1] | Fasted | | | Fed |
|---|---|---|---|---|
| | 50 mg | 150 mg | 300 mg | 150 mg |
| Cmax (ng/mL) | 125 ± 22.0 (6) | 360 ± 60.4 (6) | 781 ± 158 (6) | 315 ± 062 (6) |
| Tmax (h) | 2.04 (6) | 2.04 (6) | 1.96 (6) | 2.58 (6) |

TABLE 12-continued

Summary of pharmacokinetic parameters for (R)-pramipexole after oral administration of single 50 mg, 150 mg, and 300 mg doses to healthy volunteers under fasted conditions and 150 mg under fed conditions.

| Parameter[1] | Fasted | | | Fed |
|---|---|---|---|---|
| | 50 mg | 150 mg | 300 mg | 150 mg |
| AUC(0-t) (h · ng/mL) | 989 ± 295 (6) | 3,387 ± 746 (6) | 8,339 ± 3,202 (6) | 3,099 ± 920 (6) |
| AUC(inf) (h · ng/mL) | 1,254 ± 347 (6) | 3,815 ± 972 (5) | 8,623 ± 3,262 (6) | 3,397 ± 944 (6) |
| $\lambda z$ ($h^{-1}$) | 0.1064 ± 0.0171 (6) | 0.1001 ± 0.0087 (5) | 0.1151 ± 0.0309 (6) | 0.1152 ± 0.0256 (6) |
| $t_{1/2}$ (h) | 6.65 ± 1.07 (6) | 6.96 ± 0.56 (5) | 6.40 ± 1.73 (6) | 6.28 ± 1.48 (6) |
| CL/F (mL/min) | 706 ± 182 (6) | 692 ± 183 (5) | 659 ± 260 (6) | 774 ± 165 (6) |
| Vz/F (L) | 395 ± 61.9 (6) | 411 ± 081 (5) | 346 ± 98.5 (6) | 406 ± 62.8 (6) |
| Ue (mg) | 35.3 ± 5.19 (6) | 60.5 ± 7.04 (6) | 198 ± 28.0 (6) | . ± . (0) |
| Fe (% Dose) | 70.7 ± 10.4 (6) | 40.3 ± 4.69 (6) | 65.8 ± 9.33 (6) | . ± . (0) |
| CLr (mL/min) | 628 ± 149 (6) | 310 ± 74.3 (6) | 441 ± 159 (6) | . ± . (0) |

[1]Mean ± standard deviation (N) except for Tmax for which the median (N) is reported.

3.2.2—Summary of (Blinded) Safety and Pharmacokinetic Results of (R)-pramipexole (Ascending Multiple-Dose Study)

This study is ongoing and has not yet been unblinded with respect to treatment assignments, and only clinical observations and pharmacokinetic data are available for the first 2 panels. To date, 2 sequential panels of 8 subjects each were enrolled to receive multiple doses of (R)-pramipexole (6 subjects) or placebo (2 subjects). The first panel was administered a singe dose of 50 mg, followed 48 hours later by 4½ days of multiple dosing (twice daily) at 50 mg Q12 hours. The second panel was administered a singe dose of 100 mg, followed 48 hours later by 4½ days of multiple dosing (twice daily) at 100 mg Q12 hours. Safety observations included vital signs, physical examination, clinical laboratory tests, ECGs, and adverse event reporting. Blood samples were collected pre-dose on Day 1 and serially for 48 hours post-dose to assess the single-dose pharmacokinetics. Blood samples were collected pre-dose on Days 5, 6, and 7 to confirm steady-state was achieved, and serially through 72 hours post-dose on Day 7 to assess the steady-state pharmacokinetics of (R)-pramipexole. Urine samples were collected for 12 hours after dosing on Day 7 to assess urinary excretion.

All 16 subjects enrolled to date have completed the study as planned. There were no deaths, reports of serious adverse events, or discontinuations because of adverse events during the study. Both dose levels were well tolerated. In cohort 1, all adverse events were mild in intensity, with the exception of moderate headaches reported by 2 subjects. In cohort 2, all adverse events were mild in intensity, with the exception of moderate "stiffness in back" and a moderate vasovagal response reported in 1 subject. An asymptomatic mild increase in heart rate upon standing (without change in blood pressure) was reported by the principal investigator for 1 of the 8 subjects dosed in cohort 1 (50 mg cohort) and for 2 of the 8 subjects dosed in cohort 2 (100 mg cohort). There were no clinically significant safety observations at any dose level.

Figure 3:
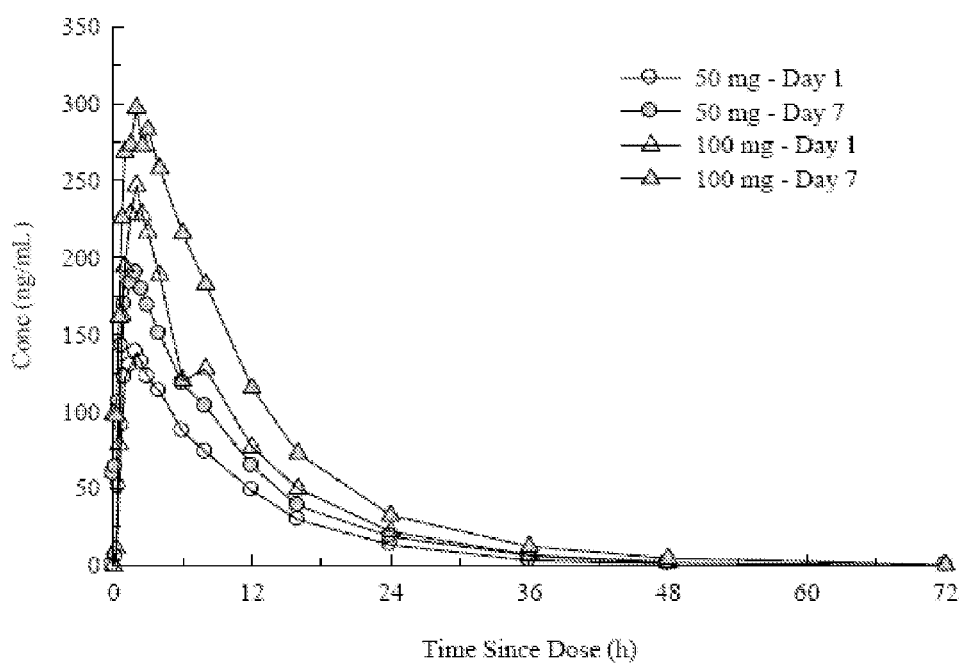
FIG. 3 depicts mean plasma (R)-pramipexole concentrations on Days 1 and 7 during oral administration of 50 mg and 100 mg doses on Day 1, Q12H on Days 3 through 6, and a single dose on Day 7 to healthy volunteers under fasted conditions.

Pharmacokinetic data are shown in Table 13 and FIG. 3. $C_{max}$ and $AUC_{(0-12)}$ increased 37% and 40%, respectively from Day 1 to Day 7 for subjects receiving 50 mg Q12H, with essentially no change in $T_{max}$. Mean exposure $AUC_{(0-12)}$ at Day 7 was 1449 h*ng/mL for the 50 mg Q12H dose group. $C_{max}$ and $AUC_{(0-12)}$ increased 24% and 38%, respectively from Day 1 to Day 7 for subjects receiving 100 mg Q12H, with essentially no change in $T_{max}$. Mean exposure $AUC_{(0-12)}$ at Day 7 was 2465 h*ng/mL for the 100 mg Q12H dose group. Results of this study demonstrate that multiple oral doses of 50 and 100 mg (R)-pramipexole administered twice daily are safe and well-tolerated. The drug is orally bioavailable and the pharmacokinetics are linear at steady state, with no significant accumulation.

TABLE 13

Summary of pharmacokinetic parameters for (R)-pramipexole during oral administration of 50 mg and 100 mg doses on Day 1, Q12H on Days 3 through 6, and a single dose on Day 7 to healthy volunteers under fasted conditions.

| Parameter[1] | Dose | |
|---|---|---|
| | 50 mg | 100 mg |
| Day 1 | | |
| Cmax (ng/mL) | 139 ± 15.3 (6) | 248 ± 30.4 (6) |
| Tmax (h) | 1.83 (6) | 1.92 (6) |
| AUC(0-12) (h · ng/mL) | 1,035 ± 121 (6) | 1,776 ± 260 (6) |
| AUC(0-t) (h · ng/mL) | 1,463 ± 280 (6) | 2,545 ± 497 (6) |
| AUC(inf) (h · ng/mL) | 1,502 ± 280 (6) | 2,574 ± 505 (6) |
| $\lambda z$ ($h^{-1}$) | 0.1132 ± 0.0230 (6) | 0.1073 ± 0.0161 (6) |
| $t_{1/2}$ (h) | 6.34 ± 1.31 (6) | 6.57 ± 0.88 (6) |
| CL/F (mL/min) | 571 ± 107 (6) | 665 ± 107 (6) |
| Vz/F (L) | 306 ± 45.8 (6) | 373 ± 51.0 (6) |

TABLE 13-continued

Summary of pharmacokinetic parameters for (R)-pramipexole during oral administration of 50 mg and 100 mg doses on Day 1, Q12H on Days 3 through 6, and a single dose on Day 7 to healthy volunteers under fasted conditions.

| Parameter[1] | Dose | |
|---|---|---|
| | 50 mg | 100 mg |
| Day 7 | | |
| Cmax (ng/mL) | 191 ± 20.9 (6) | 306 ± 055 (6) |
| Tmax (h) | 1.75 (6) | 2.00 (6) |
| AUC(0-12) (h · ng/mL) | 1,449 ± 221 (6) | 2,465 ± 299 (6) |
| $\lambda z$ ($h^{-1}$) | 0.1025 ± 0.0186 (6) | 0.0894 ± 0.0117 (6) |
| $t^{1/2}$ (h) | 6.96 ± 1.30 (6) | 7.88 ± 1.19 (6) |
| CL/F (mL/min) | 585 ± 81.6 (6) | 684 ± 76.1 (6) |
| Vz/F (L) | 346 ± 30.1 (6) | 466 ± 82.2 (6) |
| Ue (mg) | . ± . (0) | . ± . (0) |
| Fe (% Dose) | . ± . (0) | . ± . (0) |
| CLr (mL/min) | . ± . (0) | . ± . (0) |

[1]Mean ± standard deviation (N) except for Tmax for which the median (N) is reported.

3.3—Toxicology Studies

In a 2-week repeat-dose toxicology studies in rats, animals received 50, 150, and 500 mg/kg doses of (R)-pramipexole for 14 days. (R)-pramipexole caused mortality at the high dose of 500 mg/kg and statistically significant changes in body weight gain and food consumption for both sexes were observed in the animals surviving to terminal sacrifice. No target organ toxicity by histopathology examination was identified at any dose. The NOAEL for this 2-week study in rats was determined to be 150 mg/kg. Following this study, 3- and 6-month repeat dose toxicology studies were completed at doses of 30, 100, and 300 mg/kg. The results of the 3-month study contain some target organ toxicity by histopathology examination at the highest dose (300 mg/kg) with no test article related deaths and no significant clinical observations outside of several incidences of convulsions in high dose rats lasting approximately 2 minutes. The animals' health did not appear to be otherwise adversely affected by these convulsions. Test article-related microscopic changes were observed in the liver (minimal grade cholestasis correlating with increased total bilirubin), ileal small intestine (minimal grade mineralization), and thymus (minimal grade lymphoid depletion correlating with lower group thymus weights compared to controls). The NOAEL for the 3-month study in rats is considered to be 100 mg/kg. Systemic exposure ($AUC_{0-last}$) at week 13 at the NOAEL dose of 100 mg/kg was 61,299 h*ng/mL in males and 61,484 h*ng/mL in females. The in-life phase of the 6-month toxicology study in rats was recently completed and histopathologic examinations are pending. There were no mortalities at any dose level between the 13-week and 26-week sacrifices.

In a 2-week repeat-dose toxicology study in minipigs, animals received 7.5, 25 and 75 mg/kg doses of (R)-pramipexole for 14 days. No target organ toxicity by histopathology examination was identified at any dose. Clinical observations included salivation, decreased activity, emesis and inappetance, with higher incidences of emesis in females than males, and mostly in the 75 mg/kg group. The incidence of emesis at 75 mg/kg (at least one episode in 5 of 8 animals dosed at 75 mg/kg) suggested this dose is close to the limit of tolerability for (R)-pramipexole for chronic dosing in minipigs. Since no test article related toxicological changes were observed at the high dose, the NOAEL for the 2-week study was considered to be greater than or equal to 75 mg/kg. Based on this study, 3-, and 6-, and 9-month repeat dose studies of (R)-pramipexole in minipigs were initiated at dose levels of 7.5, 25 and 75 mg/kg. At month 2, dose levels were reduced to 7.5, 25 and 50 mg/kg due to mortalities at the 75 mg/kg level. The 3- and 6-month repeat dose studies have now been completed at the 7.5, 25 and 50 mg/kg dose levels and the 9-month repeat dose study is ongoing. No target organ toxicity by histopathology examination was identified at any dose level following animal sacrifice after 3 months of exposure. The NOAEL for the 3-month study in minipigs is considered to be 50 mg/kg. Systemic exposure ($AUC0-24$) at week 13 at the NOAEL dose of 50 mg/kg/day was 91,812 h*ng/mL in males and 131,731 h*ng/mL in females. The in-life phase of the 6-month toxicology study in minipigs was recently completed and histopatholgic examinations are pending. There were no mortalities attributed to test article or significant clinical observations at any dose level between the 13-week and 26-week sacrifices. The ongoing 9-month toxicology studies in minipigs have now passed month 7 and no deaths attributed to test article or significant clinical observations have occurred at any dose level.

3.4. Human Dosages

The development of (R)-pramipexole as a treatment of ALS is based on a maximally tolerated dose strategy, derived either from tolerability or safety data from studies in humans or from the results of animal toxicology studies. To date there have been no dose-limiting tolerability observations in humans. Therefore, in order to progress dosing in humans, it is necessary to closely examine the exposure at which toxicity has been observed in rats and minipigs. Pharmacokinetic data obtained to date suggest that pharmacokinetics in humans will continue to be dose-proportional at higher doses, and that the accumulation factor will be constant. Safety and toxicokinetic results from the 3 month toxicology studies in rats and minipigs show no adverse effects of chronic dosing up to 100 mg/kg in rats and 50 mg/kg in minipigs. Analysis of safety margins in (R)-pramipexole exposure between the NOAEL for minipigs and the projections of human exposure, therefore, support progression of total daily doses up to 500 mg in humans. The projected steady-state exposure of (R)-pramipexole at a total daily dose of 500 mg administered as 250 mg Q12H is approximately 7,000 h*ng/mL, which is greater than 13-fold lower than exposures seen at the NOAEL in male minipigs and approximately 9-fold lower than exposures seen at the NOAEL in male and female rats after 13 weeks of dosing.

Figure 4:
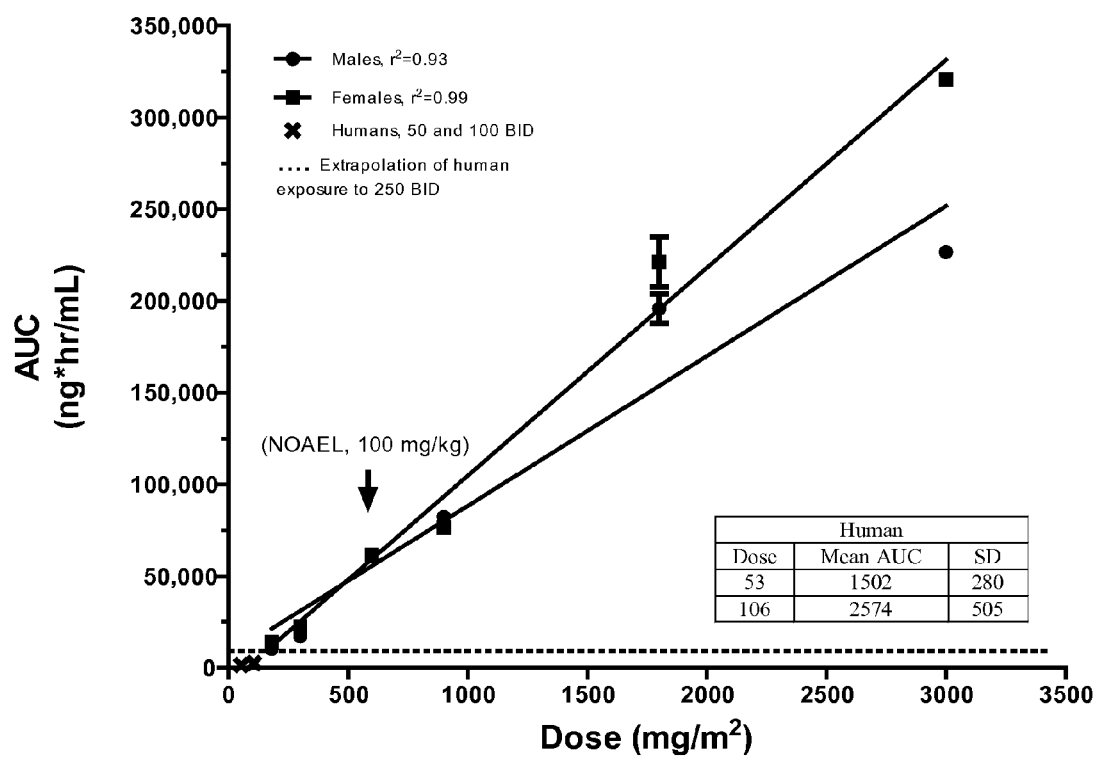
FIG. 4 depicts an exposure (AUC) vs. dose ($mg/m^2$) for male and female rats and humans (both genders).
Figure 5:
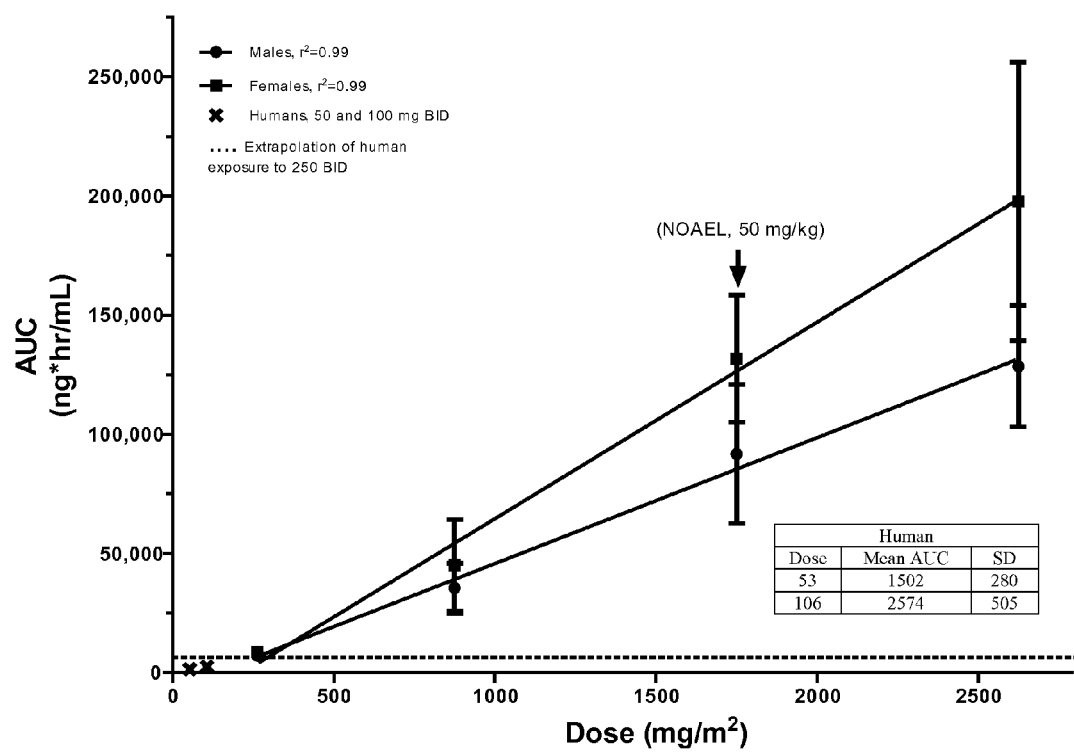
FIG. 5 depicts mean exposure (AUC) vs. dose ($mg/m^2$) for male and female minipigs and humans (both genders).

FIGS. 4 and 5 are plots of exposure vs. dose for rats and minipigs, respectively, compared with humans. Each graph displays the relationship between exposure as expressed by AUC (h*ng/mL) and dose as expressed by body surface area (mg/m2) at every dose level administered to each species in both the 2-week and 13-week assessments. Individual data points with error bars are the mean±SD. The dashed horizontal line at the bottom of both charts illustrates the extrapolated steady state AUC (7,000 h*ng/mL) in humans at 250 mg Q12H. Table 17A and Table 17B are an integrated summary of all human pharmacokinetic estimates obtained in the two Phase I studies.

TABLE 17A

Summary of the human pharmacokinetic estimates obtained in the two Phase I studies with healthy volunteers

| Study | Dose (mg) | Dosing Regimen | Food | Cmax (ng/mL) | Tmax (h) | AUC(0-t) (h*ng/mL) | AUC (inf) (h*ng/mL) | AUC(0-12) (h*ng/mL) |
|---|---|---|---|---|---|---|---|---|
| CL001 | 50 | SD | Fasted | 125 ± 22.0 (6) | 2.04 (6) | 989 ± 295 (6) | 1,245 ± 347 (6) | — |
|  | 150 | SD | Fasted | 360 ± 60.4 (6) | 2.04 (6) | 3,387 ± 746 (6) | 3,815 ± 972 (5) | — |
|  | 300 | SD | Fasted | 781 ± 158 (6) | 1.96 (6) | 8,339 ± 3,202 (6) | 8,623 ± 3,262 (6) | — |
|  | 150 | SD | Fasted | 315 ± 062 (6) | 2.58 (6) | 3,099 ± 920 (6) | 3,397 ± 944 (6) | — |
| CL002 | 50 | Q12H (Day 1) | Fasted | 139 ± 15.3 (6) | 1.83 (6) | 1,463 ± 280 (6) | 1,502 ± 280 (6) | 1,035 ± 121 (6) |
|  |  | (Day 7) | Fasted | 191 ± 20.9 (6) | 1.75 (6) | — | — | 1,449 ± 221 (6) |
|  | 100 | Q12H (Day 1) | Fasted | 248 ± 30.4 (6) | 1.92 (6) | 2,545 ± 497 (6) | 2,574 ± 505 (6) | 1,776 ± 260 (6) |
|  |  | (Day 7) | Fasted | 306 ± 055 (6) | 2.00 (6) | — | — | 2,465 ± 299 (6) |
|  | 250 | Q12H (Day 1) | Fasted | — | — | — | — | — |
|  |  | (Day 7) | Fasted | — | — | — | — | — |

Mean ± standard deviation (N) except for $T_{max}$ for which the median (N) is reported.
SD = single dose

TABLE 17B

Summary of the human pharmacokinetic estimates obtained in the two Phase I studies with healthy volunteers (continued)

| Study | Dose (mg) | Dosing Regimen | Food | t ½ (h) | CL/F (mL/h) | Vz/F (L) | Ue (mg) | Ue (% Dose) | CLx (mL/min) |
|---|---|---|---|---|---|---|---|---|---|
| L001 | 50 | SD | Fasted | 6.65 ± 1.07 (6) | 706 ± 182 (6) | 395 ± 61.9 (6) | 35.3 ± 5.19 (6) | 70.7 = 10.4 (6) | 628 = 149 (6) |
|  | 150 | SD | Fasted | 6.96 ± 0.56 (5) | 692 ± 183 (5) | 411 ± 081 (5) | 60.5 ± 7.04 (6) | 40.3 ± 4.69 (6) | 310 = 74.3 (6) |
|  | 300 | SD | Fasted | 6.40 ± 1.73 (6) | 659 ± 260 (6) | 346 ± 98.5 (6) | 198 ± 28.0 (6) | 65.8 = 9.33 (6) | 441 = 159 (6) |
|  | 150 | SD | Fasted | 6.28 ± 1.48 (6) | 774 ± 165 (6) | 406 ± 62.8 (6) | . ± (0) | . ± (0) | . ± (0) |
| L002 | 50 | Q12H (Day 1) | Fasted | 6.34 ± 1.31 (6) | 571 ± 107 (6) | 306 ± 45.8 (6) | — | — | — |
|  |  | (Day 7) | Fasted | 6.96 ± 1.30 (6) | 585 ± 81.6 (6) | 346 ± 30.1 (6) | . ± (0) | . ± (0) | . ± (0) |
|  | 100 | Q12H (Day 1) | Fasted | 6.57 ± 0.88 (6) | 665 ± 107 (6) | 373 ± 51.0 (6) | — | — | — |
|  |  | (Day 7) | Fasted | 7.88 ± 1.19 (6) | 684 ± 76.1 (6) | 466 ± 82.2 (6) | . ± (0) | . ± (0) | . ± (0) |
|  | 250 | Q12H (Day 1) | Fasted | — | — | — |  |  |  |
|  |  | (Day 7) | Fasted | — | — | — |  |  |  |

Mean ± standard deviation (N) except for $T_{max}$ for which the median (N) is reported.
SD = single dose Exposure at steady state in rats, minipigs, and humans is linear across all doses studied. After 3 months of dosing, the NOAEL in rats has been determined to be 100 mg/kg; and the NOAEL in minipigs has been determined to be 50 mg/kg. The mean AUC in rats at the NOAEL was 61,299 and 61,484 h*ng/mL for males and females, respectively, and for minipigs was 91,812 and 131,731 h*ng/mL for males and females, respectively. The mean AUC in humans at steady state at a dose of 100 mg Q12H (200 mg total daily dose) was 2,574 h*ng/mL.

Example 4—Preparation of Capsules with (R)-Pramipexole (R)-(+)-pramipexole dihydrochloride monohydrate is filled in hard gelatin capsules with no excipients. The capsules used for the drug product are #00 blue opaque gelatin capsules from Hawkins Chemical Group. Dose strengths of 50 and 500 mg are produced. Matching placebo capsules are filled with microcrystalline cellulose. Capsules are prepared by weighing individual empty capsules and recording the weight ($W_e$). Specified amount of active drug substance are individually weighed and hand-filled into a capsule bottom using a Torpac® filling funnel. A purity adjustment factor of 1.0638 is used to adjust for the water weight (monohydrate) in the salt form, i.e., a 50 mg dose should have a target fill of 50×1.0638=53.16 mg. Capsule tops are joined with the filled capsule bottom. The filled capsules are then weighed, and the weight is recorded ($W_f$). The calculated weight of the drug substance in the capsule ($W_f$—$W_e$) is recorded. If this calculated weight is within +/−5% of the nominal weight, then the capsule is cleaned, polished, and placed into and appropriately labeled container. If the calculated weight is outside of the specified range, the capsule is discarded. The free-base weight per capsule (free-base weight per mg of capsule contents multiplied by fill weight) is 90% to 100% of the calculated label claim. Total impuritie are ≤2%. The appearance is a blue capsule containing white to off-white powder.

Example 4B—Preparation of Tablets with (R)-pramipexole

Capsules with 125 mg dose strength are prepared with the composition shown in Table 17. Capsules are generally prepared under conditions of 60 to 74° F. and a relative humity of 30 to 60%. Microcrystalline cellulose, mannitol, crospovidone, magnesium stearate, and (R)-pramipexole (milled) are weighed out in the amounts shown in the column "Quantity/batch" in Table 14. The microcrystalline cellulose, mannitol, crospovidone, and (R)-pramipexole are then hand screened through a #20 mesh stainless steel screen and transferred to a Maxiblend V-blender with a 4 quart shell. The materials are then mixed using the Maxiblend V-blender for 10 minutes. The magnesium stearate is then screened using a 30 mesh stainless steel hand screen and transferred to the blender. The powders are then mixed for five minutes. The final blend is then emptied into a labeled, double PE-lined drum and the gross, tare, and net weights are recorded.

Tablets are prepared using a Minipress II B with 5 stations of ⅜" round, standard, concave tooling and gravity feed frame. The final blend is placed in the hopper and the tablet press set up is run according to the specifications in Table 15.

TABLE 14

Tablet and Batch Compositions

| Ingredient | Percent | Quantity/ unit (mg) | Quantity/ batch (g) |
| --- | --- | --- | --- |
| (R)-Pramipexole (milled) | 40.00 | 125.00 | 400.000 |
| Microcrystalline cellulose (Avicel PH102) (Diluent) | 35.25 | 110.16 | 352.512 |
| Mannitol (Pearlitol SD100) (Diluent) | 20.00 | 62.50 | 200.000 |
| Crospovidone (Polyplasdone XL) (Disintegrant) | 4.00 | 12.50 | 40.000 |
| Magnesium stearate (vegetable source, grade 905-G) (Lubricant) | 0.75 | 2.34 | 7.488 |
| Total | 100.00 | 312.50 | 1000.000 |

TABLE 15

Tablet Press Settings

| Parameter | Target (range) |
| --- | --- |
| Average tablet weight (10 tablets) | 3.125 g (3.031 g to 3.219 g) (+/−3%) |
| Target weight (individual tablet) | 312.5 mg (296.9 mg to 328.1 mg) (+/−5%) |
| Target hardness | 12 Kp (6 Kp to 18 Kp) |
| Press speed | 20 rpm (10 to 30 rpm) |

Example 5—Preparation of (R)-pramipexole p-TSA Salt: Condition A

All reagents were purchased from CNH technologies, Fisher, Aldrich, G.J. Chemicals, Puritan, TCI and Spectrum and were used as provided. Proton nuclear magnetic resonance spectra were obtained on a Bruker AC 300 spectrometer at 300 MHz. HPLC analysis for chiral purity was performed on a Chiralpak® IA column (5 µM, 250×4.6 mm) at 30° C. using a mobile phase of heptane/ethanol/diethylamine (80:20:2 v/v/v). HPLC analysis for chemical purity was performed on a Sunfire® column (3.5 µM, 150×4.6 mm) at 30° C. using two mobile phases: A—0.5% TFA in water; and B—0.5% TFA in methanol. A gradient of 5% B to 80% B was used to separate the diamine and pramipexole peaks. A detection wavelength of 265 nm was used for both HPLC analyses.

Each of the processes detailed in examples 5-14 may also be scaled for industrial manufacturing processes, as shown in examples 15-17. Certain examples have been detailed at both the laboratory scale and the industrial manufacturing scale to demonstrate that the chemical and chiral yields are independent of the scale of the synthesis.

A 2.0 liter, three-necked flask was equipped with an overhead stirrer, a temperature probe, a heating mantle, a claisen joint, a reflux condenser, and a 500 ml addition funnel. The flask was charged with 45 grams of R(+)-2,6 diamino-4,5,6,7-tetrahydro-benzothiazole, followed by 750 ml of n-propanol. Under continuous stirring, the mixture was heated to a temperature of 95° C. over 15 minutes generating a clear solution. The addition funnel was charged with a solution of 74 grams propyl tosylate and 60 ml diisopropylethyleamine in 250 ml n-propanol. This solution was added dropwise to the 2.0 liter flask with continuous stirring over a period of 4 hours. The reaction was continued with stirring for an additional 8 hours at 95° C., after which the solution was brought to room temperature, and stirring was continued for an additional 4 hours.

The precipitated material was collected by filtration and washed three times using 100 ml reagent grade alcohol each time. The alcohol washed precipitated cake was then washed with 100 ml heptane and dried under high vacuum for 2 hours. The final weight of the dried product was 53.2 grams, representing a 52.2% yield. HPLC was used to determine the chemical purity of the R(+)-2,6-diamino-4,5,6,7-tetrahydro-benzothiazole ((R)-pramipexole) as 98.2% and the chiral purity as greater than 99.5%. $^1$H NMR and $^{13}$C NMR were used to confirm the structure.

Example 6—Preparation of Racemic Pramipexole p-TSA Salt: Condition A

A 250 ml, three necked flask was equipped with a magnetic stirrer, a temperature probe, a heating mantle, a claisen joint, a reflux condenser, and a 100 ml addition funnel. The flask was charged with 5 grams of racemic 2,6 diamino-4,5,6,7-tetrahydro-benzothiazole, followed by 80 ml of n-propanol. Under continuous stirring, the mixture was heated to a temperature of 95° C. over 15 minutes generating a clear solution. The addition funnel was charged with a solution of 10.12 grams propyl tosylate and 8.2 ml diisopropylethyleamine in 28 ml n-propanol. This solution was added dropwise to the 250 ml flask with continuous stirring over a period of 2 hours. The reaction was continued with stirring for an additional 6 hours at 95° C., after which the solution was brought to room temperature, and stirring was continued for an additional 6 hours.

The precipitated material was collected by filtration and washed two times using 25 ml reagent grade alcohol each time. The alcohol washed precipitated cake was then washed with 25 ml heptane and dried under high vacuum for 1 hours. The final weight of the dried product was 5.12 grams, representing a 45% yield. HPLC was used to determine the chemical purity of the racemic 2,6-diamino-4,5,6,7-tetrahydro-benzothiazole (racemic pramipexole) as 97.12%, and the chiral purity showed a 1:1 mixture of the R(+) and (S)-pramipexole. $^1$H NMR was used to confirm the structure.

Example 7—Preparation of (R)-Pramipexole p-TSA Salt: Condition C

A 12 L, three necked flask was equipped with an overhead stirrer, a temperature probe, a heating mantle, a claisen joint, a condenser, and a 500 ml addition funnel. The flask was charged with 250 grams of R(+)-2,6 diamino-4,5,6,7-tetrahydro-benzothiazole (R(+) diamine), followed by 2 L of dimethyl formamide (DMF). Under continuous stirring, the mixture was heated to a temperature of 65° C. The addition funnel was charged with a solution of 386.6 grams propyl tosylate (1.25 molar equivalents) and 322 ml diisopropylethyleamine (1.25 molar equivalents) in 500 ml DMF. This solution was added to the 12 L flask dropwise over a period of 2.0 hours. The reaction was monitored by analysis on HPLC.

The reaction was continued at 65° C. for an additional 5 hours, after which the solution was gradually cooled to room temperature and stirred overnight. The solution was diluted with 2 L MTBE and stirred for an additional 0.5 hours. The precipitated material was collected by filtration and washed with 500 ml MTBE, followed by 3 washes of 500 ml each reagent alcohol. The washed precipitated cake was dried under high vacuum.

The final weight of the dried product was 317.6 grams, representing a 56% yield. HPLC was used to determine the chemical purity of the R(+)-2,6-diamino-4,5,6,7-tetrahydrobenzothiazole ((S)-pramipexole) as 98.4% and the chiral purity as greater than 99.8%. $^1$H NMR and $^{13}$C NMR was used to confirm the structure: $^1$H NMR (300 MHz, DMSO-d6) δ 8.5 (br.s, 2H), 7.5 (d, 2H), 71.2 (d, 1H), 6.8 (s, 2H), 3.4 (m, 1H), 2.95 (m, 3H), 2.6 (m, 2H, merged with DMSO peak), 2.3 (s, 3H), 2.15 (m, 1H), 1.8 (m, 1H), 1.55 (m, 2H), 0.9 (t, 3H); $^{13}$C NMR (300 MHz, DMSO-d6) δ 167.0, 145.5, 144.6, 138.4, 128.6, 125.8, 110.7, 53.9, 46.5, 25.8, 25.6, 24.5, 21.2, 19.6, 11.3.

Example 8—Conversion of (R)-pramipexole p-TSA Salt to (R)-pramipexole dihydrochloride (R)-pramipexole p-TSA salt (50 grams; 0.13 mol) was taken into 150 ml absolute ethanol and cooled to between 0 and 5° C. with continuous stirring. Concentrated HCl (33 ml) was slowly added to the reaction while maintaining the temperature at between 0 and 5° C., and the mixture was stirred for an additional 15 minutes. MTBE (200 ml) was added to the mixture, and stirring was continued for an additional 1.5 hours at temperature. The reaction mixture was then filtered, washed twice with an MTBE/ethanol solution (2:1, 2×50 ml wash volumes), and dried under vacuum at 30° C. overnight. The final product was 34 grams of (R)-pramipexole dihydrochloride, indicative a of 92% yield, and a 97.3% chemical purity as determined by HPLC.

Example 9—Conversion of (R)-pramipexole p-TSA Salt to (R)-pramipexole dihydrochloride (R)-pramipexole p-TSA salt (10 grams; 0.026 mol) was dissolved in 200 ml IPAC and cooled to 15° C. with continuous stirring. HCl gas was bubbled into the slurry for 1 hour. The mixture was then filtered, washed with IPAC, and dried overnight under vacuum at room temperature. The final product was 6.8 grams of (R)-pramipexole dihydrochloride, indicative a of 92% yield, and a 97% chemical purity as determined by HPLC.

Example 10—Conversion of (R)-pramipexole p-TSA Salt to (R)-pramipexole Free Base (R)-pramipexole p-TSA salt (25 grams; 0.065 mol) was dissolved in 200 ml DCM and mixed into a slurry. 10 ml of water was added and the mixture was basified with 12 ml of 6N NaOH to a pH of 11-12. The two phases were split, and the aqueous was extracted with 200 ml of DCM. The combined organic phases were dried over MgSO$_4$, filtered over Celite® and concentrated. The residue was dissolved in 100 ml MTBE and slurried for several hours. The solids were then filtered, washed with MTBE and dried under vacuum at 35° C. The final product was 9.1 grams of (R)-pramipexole dihydrochloride, indicative a of 66% yield, and a 98% chemical purity as determined by HPLC.

Example 11—Conversion of (R)-pramipexole p-TSA Salt to (R)-pramipexole Free Base Freebase formation was performed on a 200 gram scale. A 5 L, three necked, round-bottomed flask, equipped with an over head stirrer, thermometer, and addition funnel was charged with 200 g (0.522 mol) of (R)-pramipexole p-TSA salt and 1 L of water. The mixture was stirred and cooled to 10° C. The slurry was basified to a pH of about 11-12 by the slow addition of 200 ml of 6 N NaOH over period of 15 min. The reaction mixture was diluted with 500 ml of brine (sodium chloride dissolved in water) and extracted with 3×1 L of dichloromethane. The combined organic phases were washed with 1.0 L of brine, dried over MgSO$_4$, filtered and concentrated to dryness. The residue was triturated with 1 L of 1:1 IPAC:Heptane, the resulting slurry was stirred for 1 hour, filtered and the filter cake was washed with 2×250 ml of 1:1 mixture of IPAC:Heptane. The filter cake was collected and dried at 40° C. under high vacuum for 24 hours to give 94.1 grams (R)-pramipexole (85.5%) as a white solid. The chemical purity was 100% AUC as tested by HPLC, and the chiral purity was 100% AUC as tested by HPLC. $^1$H NMR and $^{13}$C NMR was used to confirm the structure: $^1$H NMR (300 MHz, DMSO-δ6) δ 6.6 (s, 2H), 2.8 (m, 2H), 2.5 (m, 2H, merged with DMSO peak), 2.2 (m, 1H), 1.9 (m, 1H), 1.5-1.3 (m, 4H), 0.85 (t, 3H); $^{13}$C NMR (300 MHz, DMSO-d6) δ 166.2, 144.8, 113.6, 54.2, 49.1, 30.0, 29.6, 25.2, 23.5, 12.3.

Example 12—Conversion of (R)-pramipexole Free Base to (R)-pramipexole dihydrochloride The freebase of (R)-pramipexole (4.8 grams; 0.022 mol) was dissolved in 200 ml of IPAC and cooled to 15° C. HCl gas was bubbled into the slurry for 1 hour. The mixture was then filtered, washed with IPAC and dried under vacuum at room temperature overnight. The final product was 6.4 grams of (R)-pramipexole dihydrochloride, indicative a of 100% yield, and a 97% chemical purity as determined by HPLC.

Example 13—Conversion of (R)-pramipexole Free Base to (R)-pramipexole dihydrochloride The freebase of (R)-pramipexole (50 grams; 0.13 mol) was dissolved in 500 ml of IPAC. Under continuous stirring, the mixture was slowly charged with 78 ml of concentrated HCl at a temperature of 25° C. The mixture was stirred overnight at ambient conditions (~25° C.), filtered and dried under vacuum at 40° C. The final product was 68 grams of (R)-pramipexole dihydrochloride, indicative a of 95% yield.

Example 14—Optical Purification of (R)-pramipexole Using Achiral Acid Addition Pramipexole enantioenriched for the R(+) enantiomer (~300 mg) was dissolved in 10 ml of the chosen solvent at 75° C. (see examples in Table 8; ethanol or acetonitrile). Complete dissolution was observed in all samples. Acid addition was made at 1.05 molar equivalents for the p-TSA (solvent is ethanol; 2.97 ml of 0.5 M acid) and MSA (solvent is acetonitrile; 1.49 ml of 1.0 M acid), and 2.05 molar equivalents for the fumaric (solvent is acetonitrile; 5.84 ml of 0.5 M acid) and phosphoric (solvent is acetonitrile; 2.90 ml of 1.0 M acid). The reaction mixtures were cooled to room temperature at a rate of 25° C./hour and stirred at room temperature for an additional 19 hours. The solids obtained by this trituration step were isolated by filtration and dried under high vacuum at room temperature. These products were analyzed by HPLC, $^1$H NMR, thermal gravimetric analysis, differential scanning calorimetry, X-ray powder diffraction (XPRD), Fourier transform infrared spectroscopy and moister-sorption analysis. The XPRD patterns showed that the p-TSA, MSA and fumarate salt forms of the (R)-pramipexole were crystalline, while the phosphate salt form of the (R)-pramipexole was amorphous.

Example 15—Industrial Scale Resolution of Racemic Diamine

A 72 L, unjacketed reactor was charged with racemic 2,6 diamino-4,5,6,7-tetrahydro-benzothiazole (rac-diamine) (4.5 kg; 26.6 mol) and 58.5 L water, and heated as a suspension to a temperature of about 60° C. to 65° C. Resolution of the enantiomers was achieved by addition of one equivalent of (D)-(−)-Tartaric acid (3991 grams; 26.6 mol) in 4.5 L of water, after which the resulting solution was heated to a temperature of about 70° C. to 75° C. and maintained at this temperature for about 1 hour. The mixture was allowed to cool to a temperature of about 20° C. to 25° C. and stirred for an additional 15 hours, after which the mixture was filtered and the solids were washed 3× with water (6.3 L each wash).

The wet solids, which contain the R(+) enantiomer of the diamine, were charged to the reactor followed by 54 L of water, and the mixture was heated to a temperature of about 70° C. to 75° C. for 2 hours. The mixture was allowed to cool to a temperature of about 20° C. to 25° C. and stirred for 17 hours. The mixture was then filtered and the solids were washed 2× with water (4.5 L each wash). The wet solids were transferred to a jacketed reactor and the reactor was charged with 8.1 L of water. The mixture was cooled to a temperature of about 0° C. to 5° C. and cautiously charged with concentrated 1.625 L of HCl, followed by 1.155 L of 50% NaOH to achieve a pH of about 9-10. During the addition the temperature was maintained at about 0° C. to 5° C., and stirred for an additional hour at temperature. The resulting mixture was then filtered and the solids were washed 2× with cold (0° C. to 5° C.) water (1.125 L each wash). The solids were transferred to a jacketed reactor and were reslurried once more with 4.5 L of water at 0° C. to 5° C. The solids were filtered and dried under warm air (40° C. to 45° C.) to give 1940 grams of the product (R(+) diamine) as a white solid, with an 86% yield for the R(+) enantiomer.

The mother liquors of the initial resolution step, which contain the S(−) enantiomer of the diamine, were concentrated to afford diamine with a 95.5% yield for the S(−) enantiomer.

TABLE 16

Experiments for industrial scale resolution of the R(+) enantiomer of diamine

| Input (grams) | Yield (%) of R(+) enantiomer | Chemical Purity (AUC % by HPLC) | Chiral Purity (AUC % by HPLC) |
|---|---|---|---|
| 1000 | 76 | >99 | 98.3 |
| 4500 | 86 | >99 | 98.5 |
| 4100 | 54 | >99 | 98.5 |

Example 16—Industrial Scale Preparation of Propyl Tosylate

A 100 L glass, jacketed reactor was charged with 1-propanol (2.098 kg; 34.9 mol), triethylamine (4.585 kg; 45.3 mol; 1.3 equivalents) and DCM (20.1 L). The mixture was cooled to a temperature of about 5° C. to 15° C. and cautiously charged with a solution of p-toluenesulfonyl chloride (6 kg; 31.47 mol; 0.9 equivalents) in DCM (10.5 L) over 30 minutes. Once the addition was complete, the mixture was warmed to a temperature of about 18° C. to 22° C. and stirred for 12 hours. The reaction mixture was assayed by $^1$H NMR (in CDCl$_3$) and deemed complete. HCl (6 N; 2.98 L) was cautiously charged while maintaining the temperature below 25° C. The aqueous phase was removed, and the organic phase was washed 2× with water (21 L each wash), dried with MgSO$_4$, and filtered over Celite®. The filtered solids were then washed with DCM (4 L) and concentrated to a residue. The residue was dissolved in heptane and concentrated again to afford a final propyl tosylate product (6.385 kg, 95% yield).

The present invention provides evidence that the dopamine receptor affinity of (R)-pramipexole is actually much lower than previously appreciated. In a study using beagle dogs presented herein, it has been shown that the functional separation between the (S)-pramipexole and (R)-pramipexole enantiomers (10,000-20,000 fold) is much greater than previously expected. These data also show that contamination of the composition of pure (R)-pramipexole with small, known amounts of (S)-pramipexole results in a predictable shift in the MTD of the composition. These data demonstrate that (R)-pramipexole can be dosed at levels that can more fully and unexpectedly exploit the lower-potency neuroprotective potential of the compound without the theoretical MTD limitation previously assumed, and without the need for dose titration. The application presents methods for using pure compositions of (R)-pramipexole in acute and chronic neurodegenerative disorders previously inaccessible to this drug and immediately at full-strength without dose-titration and at higher theoretical MTDs. Additionally, the data showing that a pure composition of (R)-pramipexole can be mixed with a known amount of (S)-pramipexole to produce dopamine receptor agonist effects determined solely by the contribution of the (S)-enantiomer allows for the use of compositions comprising the mixture of known amounts of pure (R)- and (S)-enantiomers for use in neurodegenerative disorders amenable to both dopamine receptor agonist treatment and neuroprotection, such as PD.

Example 17—Industrial Scale Preparation of (R)-pramipexole p-TSA Salt: Condition C A 72 liter unjacketed reactor was charged with 1.84 kg (10.87 mol) of R(+)-2,6 diamino-4,5,6,7-tetrahydro-benzothiazole (R(+) diamine), followed by 14.7 L of dimethyl formamide (DMF). Under continuous stirring, the mixture was heated to a temperature of between 65° C. and 68° C. A solution of 2926 grams propyl tosylate and 1761 grams diisopropylethyleamine in 3.455 L DMF was added slowly over a period of 2 hours. The reaction was continued at 67° C. for an additional 4 hours, after which the solution was gradually cooled to room temperature (18° C. to 22° C.) and stirred for an additional 15 hours. The solution was diluted with 14.72 L of MTBE over a time period of 30 minutes, and stirred for an additional 1 hour. The precipitated material was collected by filtration and washed with 7.32 L MTBE, followed by 3 washes of 3.68 L each of ethanol, and a wash with 9.2 L heptane. The washed precipitated cake was dried under high vacuum at 30° C. to 35° C. The final weight of the dried product was 2090 grams, representing a 50% yield.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A method of treating amyotrophic lateral sclerosis (ALS) in a patient comprising:
   administering to the patient a single unit dose of at least 150 milligrams of (6R)-4,5,6,7-tetrahydro-N6-propyl-2,6-benzothiazole-diamine or a pharmaceutically acceptable salt thereof; and
   administering adjunctively to the patient a therapeutically effective amount of creatine.

2. The method of claim 1, further comprising administering a mitochondrial energy promoting agent selected from the group consisting of resveratrol; erythropoietin; cholest-4-en-3-One, oxime (TRO-19622); and any combination thereof.

3. The method of claim 1, wherein the steps of administering the single unit dose of at least 150 milligrams of (6R)-4,5,6,7-tetrahydro-N6-propyl-2,6-benzothiazole-diamine or a pharmaceutically acceptable salt thereof and administering the therapeutically effective amount of creatine occurs concurrently.

4. The method of claim 1, wherein the steps of administering the single unit dose of at least 150 milligrams of (6R)-4,5,6,7-tetrahydro-N6-propyl-2,6-benzothiazole-diamine or a pharmaceutically acceptable salt thereof and administering the therapeutically effective amount of creatine occurs separately.

5. The method of claim 1, wherein the steps of administering the single unit dose of at least 150 milligrams of (6R)-4,5,6,7-tetrahydro-N6-propyl-2,6-benzothiazole-diamine or a pharmaceutically acceptable salt thereof and administering the therapeutically effective amount of creatine each individually occur one or more times in a 24-hour period.

6. The method of claim 1, wherein the single unit dose of at least 150 milligrams of (6R)-4,5,6,7-tetrahydro-N6-propyl-2,6-benzothiazole-diamine, or pharmaceutically acceptable salt thereof, has a 99.90% or greater chiral purity.

7. The method of claim 1, wherein the single unit dose comprises at least about 200 mgs of (6R)-4,5,6,7-tetrahydro-N6-propyl-2,6-benzothiazole-diamine or a pharmaceutically acceptable salt thereof.

8. The method of claim 1, wherein the single unit dose comprises at least about 300 mgs of (6R)-4,5,6,7-tetrahydro-N6-propyl-2,6-benzothiazole-diamine or a pharmaceutically acceptable salt thereof.

9. The method of claim 1, wherein the single unit dose further comprises less than about 1.0 mg of (6S)-4,5,6,7-tetrahydro-N6-propyl-2,6-benzothiazole-diamine or a pharmaceutically acceptable salt thereof.

10. The method of claim 1, comprising a course of treatment wherein the steps of administering the single unit dose of at least 150 milligrams of (6R)-4,5,6,7-tetrahydro-N6-propyl-2,6-benzothiazole-diamine or a pharmaceutically acceptable salt thereof and administering the therapeutically effective amount of creatine is repeated one or more times in a 24-hour period for 5 days to one or more years.

11. The method of claim 1, wherein the single unit dose of at least 150 milligrams of (6R)-4,5,6,7-tetrahydro-N6-propyl-2,6-benzothiazole-diamine or a pharmaceutically acceptable salt thereof is a pharmaceutically acceptable salt of (6R)-4,5,6,7-tetrahydro-N6-propyl-2,6-benzothiazole-diamine.

12. The method of claim 1, wherein the pharmaceutically acceptable salt is (6R)-4,5,6,7-tetrahydro-N6-propyl-2,6-benzothiazole-diamine dihydrochloride monohydrate.

13. A method of treating amyotrophic lateral sclerosis (ALS) in a patient comprising:
   administering to the patient a single unit dose of about 150 milligrams to about 5,000 milligrams of (6R)-4,5,6,7-tetrahydro-N6-propyl-2,6-benzothiazole-diamine or a pharmaceutically acceptable salt thereof in a pharmaceutical composition; and
   administering adjunctively to the patient a therapeutically effective amount of creatine.

14. The method of claim 13, further comprising administering a mitochondrial energy promoting agent selected from the group consisting of resveratrol; erythropoietin; cholest-4-en-3-One, oxime (TRO-19622); and any combination thereof.

* * * * *